(12) United States Patent
Warrington et al.

(10) Patent No.: US 8,802,080 B2
(45) Date of Patent: Aug. 12, 2014

(54) RAAV EXPRESSION SYSTEMS FOR GENETIC MODIFICATION OF SPECIFIC CAPSID PROTEINS

(75) Inventors: Kenneth H. Warrington, Gainsville, FL (US); Shaun R. Opie, Phoenix, AZ (US); Nicholas Muzyczka, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1507 days.

(21) Appl. No.: 10/513,059

(22) PCT Filed: May 1, 2003

(86) PCT No.: PCT/US03/13583
§ 371 (c)(1),
(2), (4) Date: Oct. 2, 2005

(87) PCT Pub. No.: WO2004/027019
PCT Pub. Date: Apr. 1, 2004

(65) Prior Publication Data
US 2006/0088936 A1 Apr. 27, 2006

Related U.S. Application Data

(60) Provisional application No. 60/377,315, filed on May 1, 2002.

(51) Int. Cl.
*C12N 15/864* (2006.01)
*C12N 7/01* (2006.01)
*C12N 5/10* (2006.01)
*C12N 15/63* (2006.01)
*C07K 14/015* (2006.01)

(52) U.S. Cl.
USPC ...... 424/93.6; 435/456; 435/320.1; 435/69.1; 435/91.41; 424/199.1; 536/24.1; 514/44 R

(58) Field of Classification Search
CPC ............ C12N 2750/14145; C12N 15/86; C12N 2750/14143; C12N 2810/50; C07K 14/05; C07K 14/015; A61K 2139/5256
See application file for complete search history.

(56) References Cited

U.S. PATENT DOCUMENTS

| | | | |
|---|---|---|---|
| 5,741,683 A * | 4/1998 | Zhou et al. | 435/457 |
| 5,910,488 A * | 6/1999 | Nabel et al. | 514/44 |
| 6,204,059 B1 * | 3/2001 | Samulski et al. | 435/456 |
| 6,329,181 B1 | 12/2001 | Xiao et al. | 435/91.41 |
| 6,692,815 B2 * | 2/2004 | Edgman | 428/181 |
| 6,723,551 B2 * | 4/2004 | Kotin et al. | 435/235.1 |
| 6,943,153 B1 | 9/2005 | Manning, Jr. et al. | |
| 6,962,815 B2 * | 11/2005 | Bartlett | 435/455 |
| 7,220,577 B2 * | 5/2007 | Zolotukhin | 435/320.1 |
| 2001/0034054 A1 | 10/2001 | Dwarki et al. | |
| 2001/0051611 A1 | 12/2001 | Srivastava et al. | |
| 2002/0132336 A1 | 9/2002 | Dwarki et al. | |
| 2002/0194630 A1 | 12/2002 | Manning, Jr. et al. | |
| 2003/0148506 A1 * | 8/2003 | Kotin et al. | 435/320.1 |
| 2003/0166284 A1 | 9/2003 | Srivastava et al. | |
| 2006/0292117 A1 * | 12/2006 | Loiler et al. | 424/93.2 |

FOREIGN PATENT DOCUMENTS

| | | |
|---|---|---|
| AU | 2003295312 | 4/2004 |
| AU | 2004226961 | 11/2004 |
| CA | 2483624 | 4/2004 |
| CA | 2500523 | 11/2004 |
| EP | 1 618 201 | 1/2006 |
| WO | WO 00/54813 A2 | 9/2000 |
| WO | WO 02/24234 A2 | 3/2002 |
| WO | WO 2004/027019 A | 4/2004 |
| WO | WO 2004/099423 A1 | 11/2004 |

OTHER PUBLICATIONS

Chiorini et al. Cloning of Adeno-Associated Virus Type 4 (AAV4) and Generation of Recombinant AAV4 Particles. Journal of Virology. p. 6823-6833, Sep. 1997.*
Hogue et al., "Chimeric Vius-like Particle Formation of Adeno-Associated Virus," *Biochem. Biophys. Res. Comm.*, 266:371-76, 1999.
Muralidhar et al., "Site-Directed Mutagenesis of Adeno-Associated Virus Type 2 Structural Protein Initiation Codons: Effects on Regulation of Synthesis and Biological Activity," *J. Virol.*, 68:170-76, 1994.
Ruffing et al., "Assembly of Viruslike Particles by Recombinant Structural Proteins of Adeno-Associated Virus Type 2 in Insect Cells," *J. Virol.*, 66:6922-30, 1992.
Shi et al., "Insertional Mutagenesis of the Adeno-Associated Virus Type 2 (AAV2) Capsid Gene and Generation of AAV2 Vectors Targeted to Alternative Cell-Surface Receptors," *Human Gene Therapy*, 12:1697-711, 2001.
Warrington et al., "Adeno-Associated Virus Type 2 VP2 Capsid Protein is Nonessential and Can Tolerate Large Peptide Insertions at Its N Terminus," *J. Virol.*, 78:6595-609, 2004.
Wu et al., "Mutational Analysis of the Adeno-Associated Virus Type 2 (AAV2) Capsid Gene and Construction of AAV2 Vectors with Altered Tropism," *J. Virol.*, 74:8635-47, 2000.
Yang et al., "Development of Novel Cell Surface CD34-Targeted Recombinant Adenoassociated Virus Vectors for Gene Therapy," *Human Gene Therapy*, 9:1929-37, 1998.

(Continued)

*Primary Examiner* — Maria Marvich
(74) *Attorney, Agent, or Firm* — Haynes and Boone, LLP

(57) ABSTRACT

Disclosed are improved recombinant adeno-associated viral (rAAV) vectors having mutations in one or more capsid proteins. Exemplary vectors are provided that have altered affinity for heparin or heparin sulfate, as well as vectors, expression systems, and rAAV virions that lack functional VP2 protein expression, but are nevertheless, fully virulent. Also provided by the invention are rAAV vector-based compositions, virus particles, host cells, and pharmaceutical formulations that comprise them useful in the expression of selected therapeutic proteins, polypeptides, peptides, antisense oligonucleotides and/or ribozymes in selected mammals, including organs, tissues, and human host cells.

28 Claims, 14 Drawing Sheets

(56) References Cited

OTHER PUBLICATIONS

Figures 1, 1A:
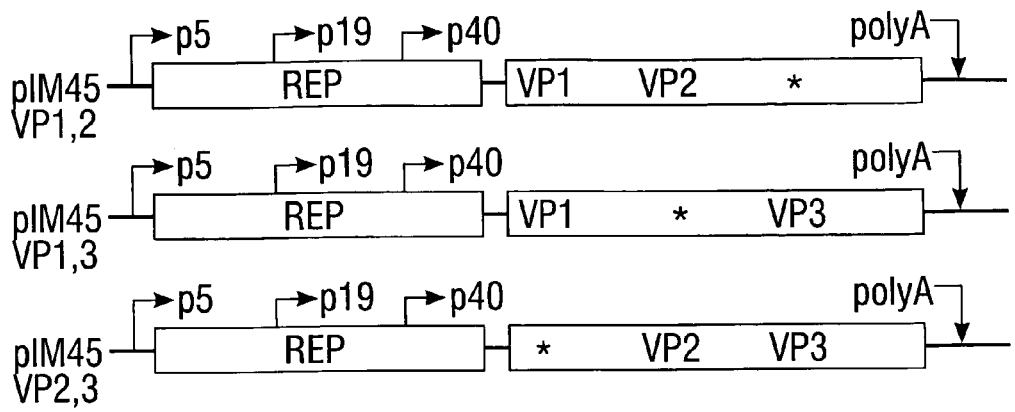
Figures 1, 1A, 2:
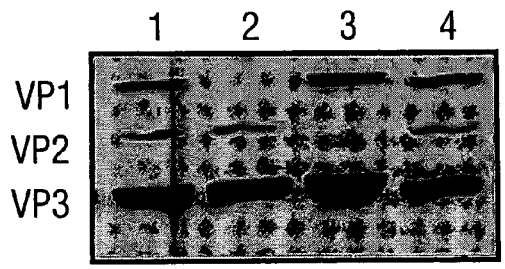

Girod et al., "Genetic Capsid Modifications Allow Efficient Re-Targeting of Adeno-Associated Virus Type 2," Nature Medicine, 5(9): 1052-1056, Sep. 1999.

Grifman et al., "Incorporation of Tumor-Targeting Peptides into Recombinant Adeno-Associated Virus Capsids," Molecular Therapy, 3(6): 946-975, Jun. 2001.

Kern et al., "Identification of a Heparin-Binding Motif on Adeno-Associated Virus Type 2 Capsid," J. Virology, 77(20): 11072-11081, Oct. 2003.

Nicklin et al., "Efficient and Selective AAV2-Mediated Gene Transfer Directed to Human Vascular Endothelial Cells," Molecular Therapy, 4(2): 174-181, Aug. 2001.

Opie et al., "Identification of Amino Acid Residues in the Capsid Proteins of Adeno-Associated Virus Type 2 that Contribute to Heparan Sulfate Proteoglycan Binding," J. Virology, The American Society for Microbiology, 77(12): 6995-7006, Jun. 20, 2003.

Rabinowitz et al., "Insertional Mutagenesis of AAV2 Capsid and the Production of Recombinant Virus," Virology, 265(2): 274-285, Dec. 20, 1999.

Steinbach et al., "Assembly of Adeno-Associated Virus Type 2 Capsid in Vitro," J. General Virology, 78(6): 1453-1462, 1997.

Xiao et al., "Production of High-Titer Recombinant Adeno-Associated Virus Vectors in the Absence of Helper Adenovirus," J. Virology, The American Society for Microbiology, 72(3): 2224-2232, Mar. 1998.

Zhang et al., "Addition of Six-His-Tagged Peptide to the C Terminus of Adeno-Associated Virus VP3 Does Not Affect Viral Tropism or Production," J. Virology, 76(23): 12023-12031, Dec. 2002.

* cited by examiner

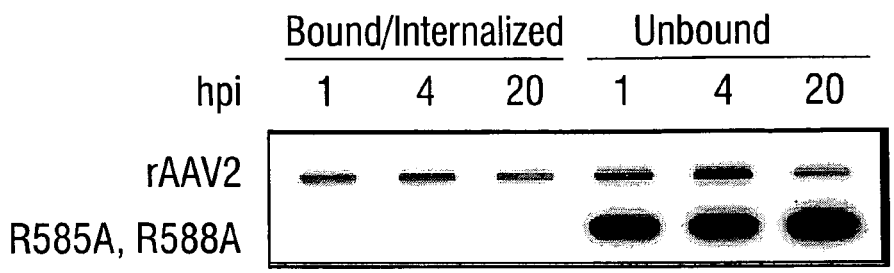
FIG. 12A
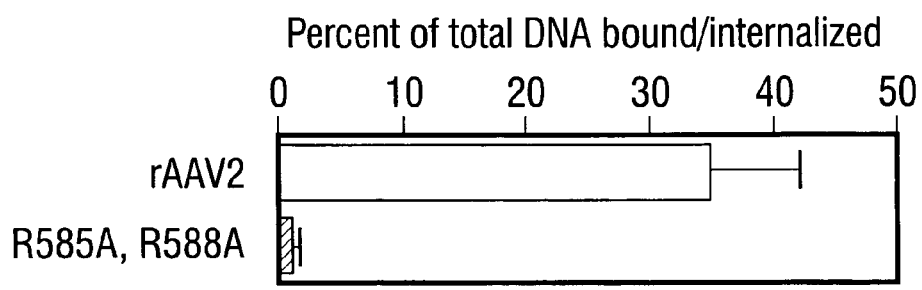
FIG. 12B
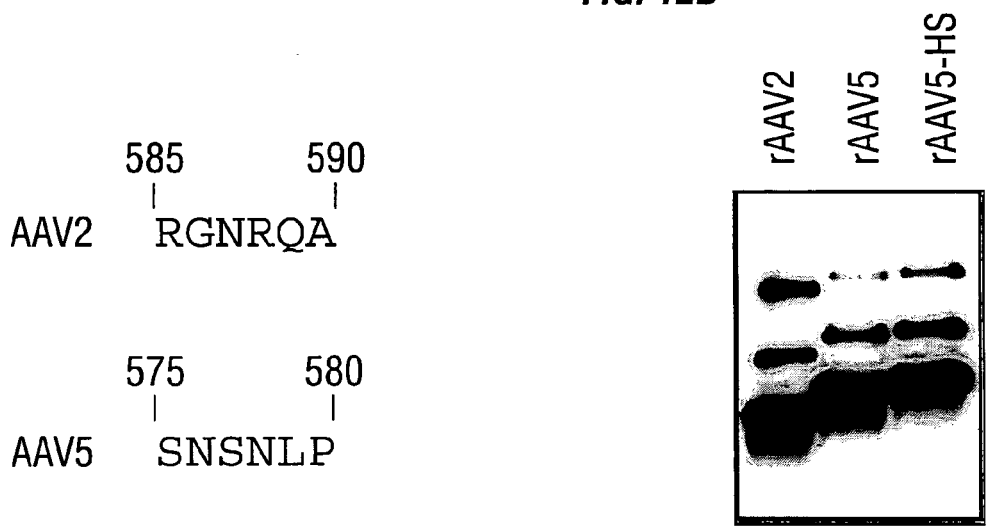
FIG. 13A
FIG. 13B
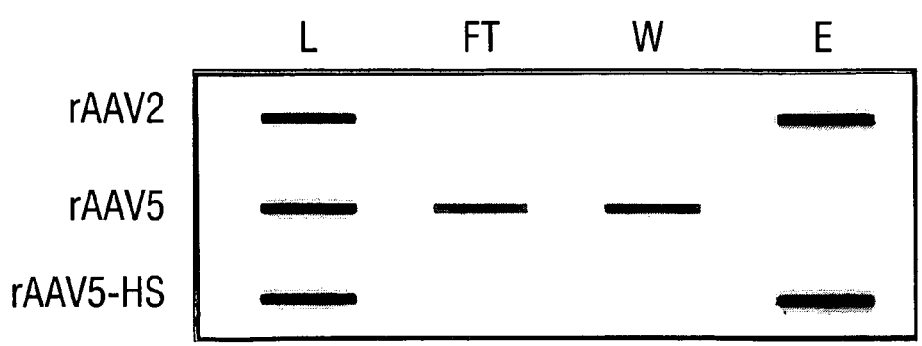
FIG. 13C pIM45/pIM45VP0 pIM45VP1/pIM45VP2,3 pIM45VP2acg/atg/pIM45VP1,3 pIM45VP3/pIM45VP1,2

UF5

1,2

1,3

2,3

HelaC12

293

HelaC12

293

SEQUENCE LISTING

<160> NUMBER OF SEQ ID NOS: 6

<210> SEQ ID NO 1
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X = ANY HYDROPATHIC AMINO ACID
<220> FEATURE:
<221> NAME/KEY: MISC_FEATURE
<222> LOCATION: (2)..(3)
<223> OTHER INFORMATION: X = His, Lys, or Arg
<220> FEATURE:
<221> NAME/KEY: MISC_FEATURE
<222> LOCATION: (4)..(4)
<223> OTHER INFORMATION: X = ANY HYDROPATHIC AMINO ACID
<220> FEATURE:
<221> NAME/KEY: MISC_FEATURE
<222> LOCATION: (5)..(5)
<223> OTHER INFORMATION: X = His, Lys, or Arg
<220> FEATURE:
<221> NAME/KEY: MISC_FEATURE
<222> LOCATION: (6)..(6)
<223> OTHER INFORMATION: X = ANY HYDROPATHIC AMINO ACID

<400> SEQUENCE: 1

Xaa Xaa Xaa Xaa Xaa Xaa
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X = ANY HYDROPATHIC AMINO ACID
<220> FEATURE:
<221> NAME/KEY: MISC_FEATURE
<222> LOCATION: (2)..(4)
<223> OTHER INFORMATION: X = His, Lys, or Arg
<220> FEATURE:
<221> NAME/KEY: MISC_FEATURE
<222> LOCATION: (5)..(6)
<223> OTHER INFORMATION: X = ANY HYDROPATHIC AMINO ACID
<220> FEATURE:
<221> NAME/KEY: MISC_FEATURE
<222> LOCATION: (7)..(7)
<223> OTHER INFORMATION: X = His, Lys, or Arg
<220> FEATURE:
<221> NAME/KEY: MISC_FEATURE
<222> LOCATION: (8)..(8)
<223> OTHER INFORMATION: X = ANY HYDROPATHIC AMINO ACID

<400> SEQUENCE: 2

Xaa Xaa Xaa Xaa Xaa Xaa Xaa Xaa
1               5

<210> SEQ ID NO 3
<211> LENGTH: 14
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(12)
<223> OTHER INFORMATION: T = A TURN

```
<220> FEATURE:
<221> NAME/KEY: MISC_FEATURE
<222> LOCATION: (2)..(3)
<223> OTHER INFORMATION: X = ANY HYDROPATHIC AMINO ACID
<220> FEATURE:
<221> NAME/KEY: MISC_FEATURE
<222> LOCATION: (4)..(4)
<223> OTHER INFORMATION: X = His, Lys, or Arg
<220> FEATURE:
<221> NAME/KEY: MISC_FEATURE
<222> LOCATION: (5)..(6)
<223> OTHER INFORMATION: X = ANY HYDROPATHIC AMINO ACID
<220> FEATURE:
<221> NAME/KEY: MISC_FEATURE
<222> LOCATION: (8)..(8)
<223> OTHER INFORMATION: X = His, Lys, or Arg
<220> FEATURE:
<221> NAME/KEY: MISC_FEATURE
<222> LOCATION: (9)..(11)
<223> OTHER INFORMATION: X = ANY HYDROPATHIC AMINO ACID
<220> FEATURE:
<221> NAME/KEY: MISC_FEATURE
<222> LOCATION: (13)..(14)
<223> OTHER INFORMATION: X = His, Lys, or Arg

<400> SEQUENCE: 3

Thr Xaa Xaa Xaa Xaa Xaa Thr Xaa Xaa Xaa Xaa Thr Xaa Xaa
1               5                   10

<210> SEQ ID NO 4
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 4
ttcaaagatg acgggaacta caa                                            23

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 5
tcaatgccct tcagctcgat                                                20

<210> SEQ ID NO 6
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 6
cccgcgctga agtcaagttc gaag                                           24
```

RAAV EXPRESSION SYSTEMS FOR GENETIC MODIFICATION OF SPECIFIC CAPSID PROTEINS

The present application claims priority to U.S. Provisional Application Ser. No. 60/377,315, filed May 1, 2002, the entire contents of which is specifically incorporated herein by reference.

The United States government has certain rights in the present invention pursuant to grant numbers HL59412 and HL51811 from the National Institutes of Health.

1. BACKGROUND OF THE INVENTION

1.1 Field of the Invention

The present invention relates generally to the fields of molecular biology and virology, and in particular, to the development of gene delivery vehicles. The invention provides improved recombinant adeno-associated virus (rAAV) vectors that while deleted for VP2, are still able to form infectious virion particles, as well as other AAV vector compositions useful in expressing a variety of nucleic acid segments, including those encoding therapeutic proteins polypeptides, peptides, antisense oligonucleotides, and ribozyme constructs, in various gene therapy regimens. Methods are also provided for preparing and using these modified rAAV-based vector constructs in a variety of viral-based gene therapies, and in particular, treatment and prevention of human diseases using conventional gene therapy approaches. The invention also provides multicomponent vector systems which may be used to assess the relative efficiency and infectivity of a variety of AAV particles having mutated, or deleted capsid proteins.

1.2 Description of Related Art

Major advances in the field of gene therapy have been achieved by using viruses to deliver therapeutic genetic material. The adeno-associated virus (AAV) has attracted considerable attention as a highly effective viral vector for gene therapy due to its low immunogenicity and ability to effectively transduce non-dividing cells. AAV has been shown to infect a variety of cell and tissue types by using heparin sulfate proteoglycan (HSPG) as its primary cellular receptor. The natural tropism of AAV for the abundantly expressed HSPG presents a challenge to specifically targeting particular cell populations. For safety and targeting considerations it is highly desirable to have a vector that cannot infect its natural host cell types.

2. SUMMARY OF THE INVENTION

The present invention overcomes these and other limitations inherent in the prior art by providing new rAAV-based genetic constructs that encode one or more mammalian therapeutic polypeptides for the prevention, treatment, and/or amelioration of various disorders resulting from a deficiency in one or more of such polypeptides. In particular, the invention provides AAV-based genetic constructs encoding one or more mammalian therapeutic proteins, polypeptides, peptides, antisense oligonucleotides, and ribozymes, as well as variants, and/or active fragments thereof, for use in the treatment and prophylaxis of a variety of conditions and mammalian diseases and disorders.

Current AAV2 targeting strategies involve inserting DNA sequences that code for specific receptor ligands within the capsid open reading frame of the pIM45 plasmid. While this approach has identified surface positions capable of tolerating peptide insertions, there are certain limitations. Because the three capsid proteins share the same open reading frame and stop codon, the amino acid sequence of the major capsid protein, VP3, and any peptide ligands inserted in this region of the open reading frame, are contained within the 2 larger and significantly less abundant capsid proteins, VP1 and VP2.

In order to target peptide ligands to a specific capsid protein, the inventors have investigated an alternative method for the production of recombinant AAV2 vectors. By mutating the capsid proteins' start codons the inventors have generated pIM45 plasmids that only express one capsid protein: pIM45-VP1, pIM45-VP2 (acg/atg), and pIM45-VP3. Such plasmids can be complemented with plasmids that express the remaining 2 capsid proteins (pIM45-VP2,3, pIM45-VP1,3, and pIM45-VP1,2, respectively) in order to produce viable recombinant AAV2 vectors. Interestingly, the plasmid, pIM45-VP1,3 is also capable of producing infectious virions in the absence of VP2 expression. Expression of the capsid proteins in this manner allows for the genetic modification of a specific capsid protein across its entire sequence. As a result, more control of the position and number of expressed peptide insertions is obtained in producing recombinant AAV2 vectors. This system allows for the production of novel targeted recombinant AAV2 vectors containing significantly larger peptide insertions in an individual capsid protein without disruption of the remaining capsid structure.

In one embodiment, the invention concerns rAAV vectors that comprise a nucleic acid segment modified to express functional VP1 and VP3 capsid proteins substantially in the absence of functional VP2 protein. Surprisingly, the inventors have shown that such a vector can produce an infectious virion in the absence of exogenous VP2 protein.

The lack or substantial absence of functional VP2 protein may be the result of at least a first mutation in the capsid gene sequence region that comprises the VP2 start codon, or alternatively in the VP2 start codon itself. An exemplary vector described herein is pIM45-VP1,3.

In another embodiment, the invention concerns rAAV vectors that comprise a nucleic acid segment modified to express functional VP1 and VP2 capsid proteins substantially in the absence of functional VP3 protein. Although such vector cannot produce an infectious virion in the absence of exogenous VP3 protein, if a second helper vector that encodes a functional VP3 protein is employed to coinfect cells with this vector, infectious virions can be obtained.

The lack or substantial absence of functional VP3 protein may be the result of at least a first mutation in the capsid gene sequence region that comprises the VP3 start codon, or alternatively in the VP3 start codon itself. An exemplary vector described herein is pIM45-VP1,2.

In a third embodiment, the invention concerns rAAV vectors that comprise a nucleic acid segment modified to express functional VP2 and VP3 capsid proteins substantially in the absence of functional VP1 protein. Although such vector cannot produce an infectious virion in the absence of exogenous VP1 protein, if a second helper vector that encodes a functional VP1 protein is employed to coinfect cells with this vector, infectious virions can be obtained.

The lack or substantial absence of functional VP1 protein may be the result of at least a first mutation in the capsid gene sequence region that comprises the VP1 start codon, or alternatively in the VP1 start codon itself. An exemplary vector described herein is pIM45-VP2,3.

A yet further embodiment of the invention is an expression vector that expresses an rAAV capsid protein selected from the group consisting of VP1, VP2, and VP3, each in the absence of substantially any other rAAV protein, such as the other capsid proteins or helper functions.

This expression vector may comprise, for example, a mutation at position 1 of the cap gene, a mutation at position 138 of the cap gene, or a mutation at position 203 of the cap gene. Exemplary such vectors provided herein are pIM45-VP1, pIM45-VP2, or pIM45-VP3, which produce substantially a single VP1, VP2, or VP3 protein, respectively.

Another embodiment of the invention is an expression vector that expresses: (a) rAAV capsid proteins VP1 and VP2 in the absence of substantial amounts of VP3 protein; (b) rAAV capsid proteins VP1 and VP3 in the absence of substantial amounts of VP2 protein; or (c) rAAV capsid proteins VP2 and VP3 in the absence of substantial amounts of VP1 protein.

Such vector typically comprises: (a) at least one mutation in the start codon of the VP1 protein and at least one mutation in the start codon of the VP2 protein; (b) at least one mutation in the start codon of the VP1 protein and at least one mutation in the start codon of the VP3 protein; or (c) at least one mutation in the start codon of the VP2 protein and at least one mutation in the start codon of the VP3 capsid protein.

For example, the vector may comprise: (a) at least one mutation at position 1 and at least one mutation at position 138 of the cap gene, (b) at least one mutation at position 1 and at least one mutation at position 203 of the cap gene; or (c) at least one mutation at position 138 and at least one mutation at position 203 of the cap gene. Vectors pIM45-VP1,2; pIM45-VP1,3; and pIM45-VP2,3 described herein, are representative examples of each of such vectors, respectively.

The invention also provides in an important embodiment, an rAAV expression system substantially lacking in expression of VP2 protein. This VP2-free system comprises: (a) at least a first rAAV vector comprising at least a first heterologous nucleic acid segment inserted into the capsid sequence region, with the segment encoding at least a first heterologous peptide; and (b) at least a second expression vector that expresses functional VP1 and VP3 capsid proteins in the absence of substantial quantities of VP2 protein, or at least a second and a third expression vector that separately express functional VP1 and VP3 capsid proteins, each of these second and third plasmids expressing a single VP1 or VP3 protein, both in the absence of substantial amounts of VP2 protein.

For example, the system will preferably comprise at least a first rAAV vector that substantially lacks VP2 expression. Such expression systems will give rise to infectious virions, so long as the helper plasmids provide sufficient exogenous VP1 and VP3 protein to permit the rAAV vector to form the capsid.

In one embodiment, when it is desirable to "target" particular cells, cell surfaces, or cell surface ligands or receptors, it may be desirable to alter the sequence of the capsid gene through the addition of one or more relatively short nucleic acid segments that encode at least 1 or more targeting peptides that, when these heterologous peptides are expressed on the surface of an rAAV virion comprising the vector, the peptide sequence contained within the altered capsid protein will permit the selective targeting of the rAAV virions comprising them to one or more specific types of cells, cell surfaces, or cell surface receptors when the particles are used to transfect a plurality or population of such host cells. The inventors contemplate that the exploitation of such targeting peptide sequences, when expressed on the surface of the rAAV virions as contained within the capsid proteins, may be critical in localizing, enhancing, improving, or increasing the specificity of the rAAV virions for a particular cell type, or may even be useful in permitting transduction of cells or cell types that previously were not appropriate host cells for AAV infection. Such methods could be particularly desirable in altering the native affinity of one or more of the various known serotypes of AAV to one or more host cells not previously capable of efficient transfection by one or more particular serotypes. For example, by appropriate insertion of one or more peptide epitopes, ligands, or recognition sequences, an rAAV serotype 1 vector may be able to efficiently transfect a cell line not readily transfected by wild-type rAAV1 vectors. Likewise, an rAAV serotype 2 vector may be sufficiently modified by addition of appropriate targeting ligands to effectively transfect one or more cell lines, cells types, tissues, or organs, not previously capable of efficient transfection using the unmodified wild-type rAAV2 vector.

As such, preferred embodiments include those VP2-free rAAV expression systems, wherein at least a first peptide inserted into one or more of the capsid protein sequences, permits the rAAV virion to transfect a specific organ tissue, or host cell, with a higher efficiency than an unmodified rAAV vector.

The VP2-free rAAV expression systems of the invention may utilize any rAAV vector, including those of serotypes 1, 2, 3, 4, 5, or 6, and may employ at least two helper plasmids such as pIM45-VP1, pIM45-VP2, or pIM45-VP3, as the second and third expression vectors required in the system to provide exogenous VP1, VP2, and/or VP3 as may be required for efficient virion formation by the rAAV vectors. When only a second helper plasmid is desired, a single vector may be employed such as, for example, pIM45-VP1,3. Alternatively, so long as at least VP1 and VP3 are provided to the system, either on a single plasmid, each on separate plasmids, or by exogenous supplementation of one or both of the purified protein(s) themselves, a fully functional, fully virulent rAAV virion may be reconstituted from the disclosed expression system, either in the presence of functional VP2 protein, or alternatively, substantially in the absence of any endogenously- or exogenously-provided VP2 protein.

When the use of such vectors is contemplated for introduction of one or more exogenous proteins, polypeptides, peptides, ribozymes, and/or antisense oligonucleotides, to a particular cell transfected with the vector, one may employ the rAAV vectors or the VP2-free rAAV expression systems disclosed herein by genetically modifying the vectors to further comprise at least a first exogenous polynucleotide operably positioned downstream and under the control of at least a first heterologous promoter that expresses the polynucleotide in a cell comprising the vector to produce the encoded peptide, protein, polypeptide, ribozyme, or antisense oligonucleotide. Such constructs may employ heterologous promoters that are constitutive, inducible, or even cell-specific promoters. Exemplary such promoters include, but are not limited to, a CMV promoter, a β-actin promoter, a hybrid CMV promoter, a hybrid β-actin promoter, an EF1 promoter, a U1a promoter, a U1b promoter, a Tet-inducible promoter and a VP16-LexA promoter.

The vectors or expression systems may also further comprise one or more enhancers, regulatory elements, transcriptional elements, to alter or effect transcription of the heterologous gene cloned in the rAAV vectors. For example, the rAAV vectors of the present invention may further comprise at least a first CMV enhancer, a synthetic enhancer, or a cell- or tissue-specific enhancer. The exogenous polynucleotide may also further comprise one or more intron sequences.

In other aspects, the invention concerns methods for altering, reducing, or eliminating, the binding of particular rAAV vectors for particular ligands. In an illustrative embodiment, the invention provides rAAV vectors that have altered affinity for heparin, heparin sulfate, and heparin sulfate proteoglycan. This vector comprises at least a first mutation in the capsid gene, wherein the mutation substantially reduces or eliminates the affinity of a viral particle comprising the vector for binding to heparin, heparin sulfate, or heparin sulfate proteoglycan. Preferably, these rAAV vectors comprise one or more Arginine to Alanine mutations, and particularly one or more Arginine to Alanine mutations at position 585 or position 588 of the capsid polypeptide sequence. In rAAV vectors comprising either a single R585A or R588A mutation, or a double mutant comprising both the R585A and the R588A mutations, affinity for heparin sulfate binding by the vector was eliminated. Such vectors are therefore important when one wishes to design improved rAAV vectors that comprise particular capsid protein mutations that either have increased or reduced affinity for one or more particular ligands.

In all aspects of the invention, the exogenous polynucleotides that are comprised within one or more of the improved rAAV vectors disclosed herein will be of mammalian origin, with human, murine, porcine, bovine, ovine, feline, canine, equine, epine, caprine, and lupine polynucleotides being particularly preferred.

As described above, the exogenous polynucleotide will preferably encode one or more proteins, polypeptides, peptides, ribozymes, or antisense oligonucleotides, or a combination of these. In fact, the exogenous polynucleotide may encode two or more such molecules, or a plurality of such molecules as may be desired. When combinational gene therapies are desired, two or more different molecules may be produced from a single rAAV expression system, or alternatively, a selected host cell may be transfected with two or more unique rAAV expression systems, each of which will provide unique heterologous polynucleotides encoding at least two different such molecules.

In other embodiment, the invention also concerns the disclosed rAAV vectors comprised within an infectious adeno-associated viral particle, comprised within one or more pharmaceutical vehicles, and may be formulated for administration to a mammal such as a human for therapeutic, and/or prophylactic gene therapy regimens. Such vectors may also be provided in pharmaceutical formulations that are acceptable for veterinary administration to selected livestock, domesticated animals, pets, and the like.

The invention also concerns host cells that comprise the disclosed rAAV vectors and expression systems, particularly mammalian host cells, with human host cells being particularly preferred.

Compositions comprising one or more of the disclosed rAAV vectors, expression systems, infectious AAV particles, host cells also form part of the present invention, and particularly those compositions that further comprise at least a first pharmaceutically-acceptable excipient for use in the manufacture of medicaments and methods involving therapeutic administration of such rAAV vectors. Such pharmaceutical compositions may optionally further comprise liposomes, a lipid, a lipid complex; or the rAAV vectors may be comprised within a microsphere or a nanoparticle. Pharmaceutical formulations suitable for intramuscular, intravenous, or direct injection into an organ or tissue of a human are particularly preferred.

Other aspects of the invention concern recombinant adeno-associated virus virion particles, compositions, and host cells that comprise one or more of the AAV vectors disclosed herein, such as for example pharmaceutical formulations of the vectors intended for administration to a mammal through suitable means, such as, by intramuscular, intravenous, or direct injection to cells, tissues, or organs of a selected mammal. Typically, such compositions may be formulated with pharmaceutically-acceptable excipients as described herein below, and may comprise one or more liposomes, lipids, lipid complexes, microspheres or nanoparticle formulations to facilitate administration to the selected organs, tissues, and cells for which therapy is desired.

Kits comprising one or more of the disclosed vectors, virions, host cells, viral particles or compositions; and (ii) instructions for using the kit in therapeutic, diagnostic, or clinical embodiments also represent preferred aspects of the present disclosure. Such kits may further comprise one or more reagents, restriction enzymes, peptides, therapeutics, pharmaceutical compounds, or means for delivery of the compositions to host cells, or to an animal, such as syringes, injectables, and the like. Such kits may be therapeutic kits for treating or ameliorating the symptoms of particular diseases, and will typically comprise one or more of the modified AAV vector constructs, expression systems, virion particles, or therapeutic compositions described herein, and instructions for using the kit.

Another important aspect of the present invention concerns methods of use of the disclosed vectors, virions, expression systems, compositions, and host cells described herein in the preparation of medicaments for treating or ameliorating the symptoms of various polypeptide deficiencies in a mammal. Such methods generally involve administration to a mammal, or human in need thereof, one or more of the disclosed vectors, virions, host cells, or compositions, in an amount and for a time sufficient to treat or ameliorate the symptoms of such a deficiency in the affected mammal. The methods may also encompass prophylactic treatment of animals suspected of having such conditions, or administration of such compositions to those animals at risk for developing such conditions either following diagnosis, or prior to the onset of symptoms.

3. BRIEF DESCRIPTION OF THE DRAWINGS

Figures 1, 1B:
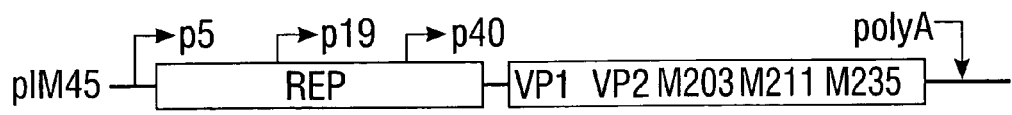
Figures 1, 1B, 2:
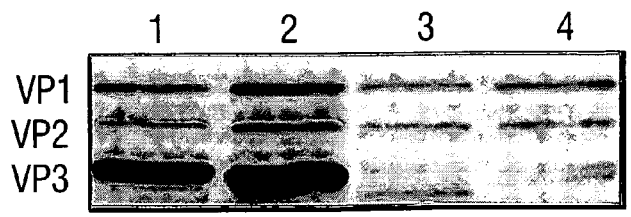
Figures 1, 1C:
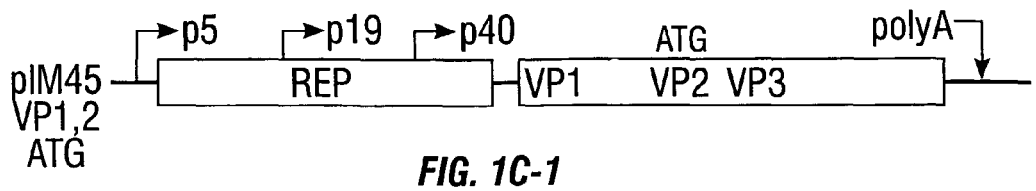
Figures 1, 1C, 2:
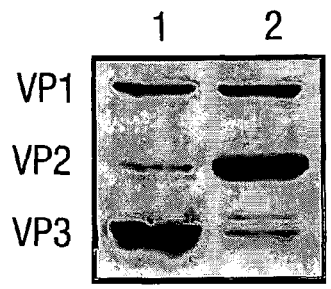

The following drawings form part of the present specification and are included to further demonstrate certain aspects of the present invention. The invention may be better understood by reference to the following description taken in conjunction with the accompanying drawings, in which like reference numerals identify like elements, and in which:

FIG. 1A-1, 1A-2, FIG. 1B-1, 1B-2, FIG. 1C-1 and FIG. 1C-2 show generation of plasmids that express two capsid proteins through missense mutation of individual capsid protein start codons. FIG. 1A shows mutations required to eliminate VP1 and VP2 expression. Immunoblot of whole cell lysates using B1 antibody that recognizes all three capsids following transfection of plasmids, pIM45(lane 1); pIM45-VP2,3 (lane 2); pIM45-VP1,3 (lane 3): and pIM45-M203L (lane 4). Note, lane 4 is the initial attempt to produce plasmid that expresses only VP1 and VP2. Further mutations are required. FIG. 1B shows mutations required to eliminate VP3 expression. Immunoblot of whole cell lysates using B1 antibody that recognizes all three capsid following transfection of pIM45 (lane 1); pIM45-M203L (lane 2); pIM45-M203,211L (lane 3): pIM45-M203,211,235L (lane 4). Note, pIM45-M203,211,235L is designated pIM45-VP1,2. FIG. 1C shows alternative mutation used to eliminate VP3 expression while maximizing<expression of VP2 protein. Immunoblot of whole cell lysates using B1 antibody that recognizes all three capsid proteins following transfection of pIM45 (lane 1) and pIM45-VP1,2A (lane 3) in which the start codon for VP2 protein is changed from ACG to ATG.

Figure 2A:
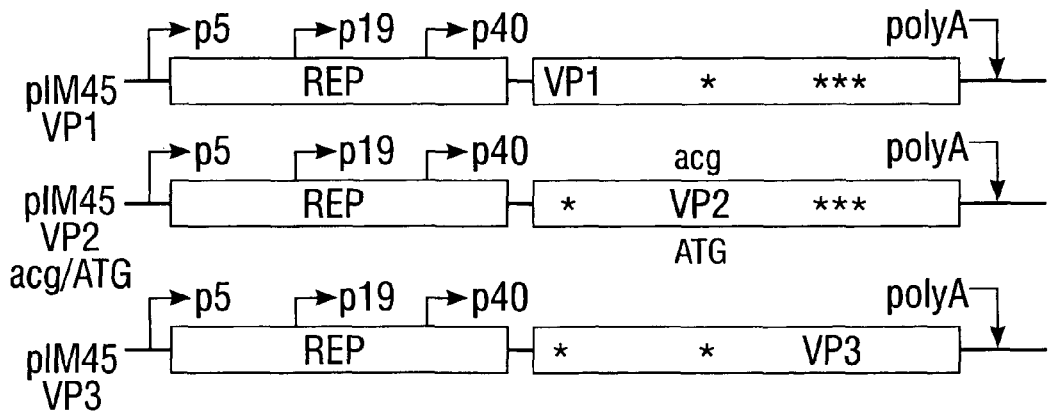
Figure 2B:
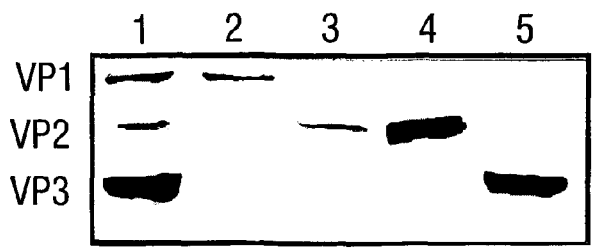

FIG. 2A and FIG. 2B show generation of plasmids that express a single capsid protein. Immunoblot of whole cell lysates using B1 antibody that recognizes all three capsid proteins following transfection of pIM45 (lane 1); pIM45-VP1 (lane 2); pIM45-VP2 (lane 3) pIM45-VP2A (lane 4); pIM45-VP3 (lane 5).

Figures 1, 3A:
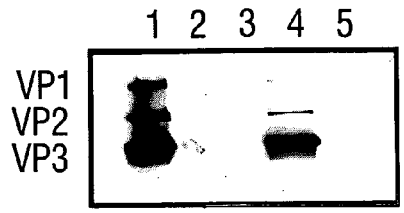
Figures 2, 3A:
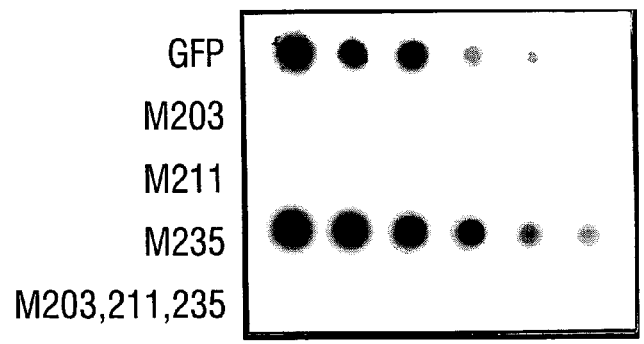
Figures 1, 3B:
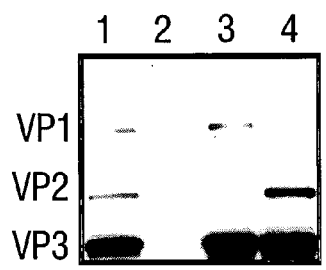
Figures 2, 3B:
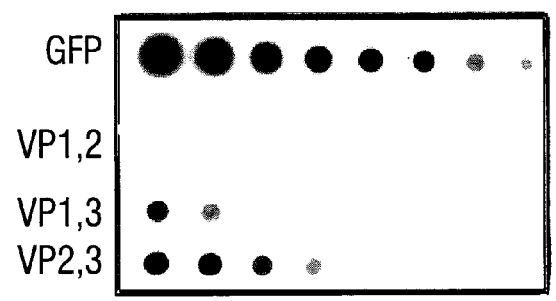

FIG. 3A-1, FIG. 3A-2, FIG. 3B-1, FIG. 3B-2, FIG. 3C-1 and FIG. 3C-2 show production and purification of rAAV2-like particles that lack expression of specific capsid proteins. FIG. 3A shows analysis of effects of missense mutations required to eliminate VP3 expression. Left panel shows immunoblot using B1 antibody that recognizes all three capsid proteins of purified particle stocks from pIM45 (lane 1); pIM45-M203L (lane 2); pIM45-M211L (lane 3); pIM45-M235L (lane 4), pIM15-M203,211,235 (lane 5). Right panel shows dot blot autoradiograph of DNA extracted from same particle stocks. Aliquots from an iodixinal step gradient were with incubated with DNAseI, inactivated with EDTA, digested with proteinase K, phenol:chloroform extracted, and precipitated with ethanol. DNA was transferred to nitrocellulose and probed with radiolabelled GFP probe. FIG. 3B shows analysis of effects of eliminating a single capsid on the production and purification of virus particles. Left panel shows immunoblot using B1 antibody that recognizes all three capsid proteins of purified, particle stocks from pIM45 (lane 1); pIM45-VP1,2 (lane 2); pIM45-VP1,3 (lane 3); and pIM4S-VP2,3 (lane 4). Right panel shows dot blot autoradiograph of DNA extracted from same particle stocks. Aliquots from an iodixinal step gradient were with incubated with DNAseI, inactivated with EDTA, digested with proteinase K, phenol:chloroform extracted, and precipitated with ethanol. DNA was transferred to nitrocellulose and probed with radiolabelled GFP probe.

Figure 4:
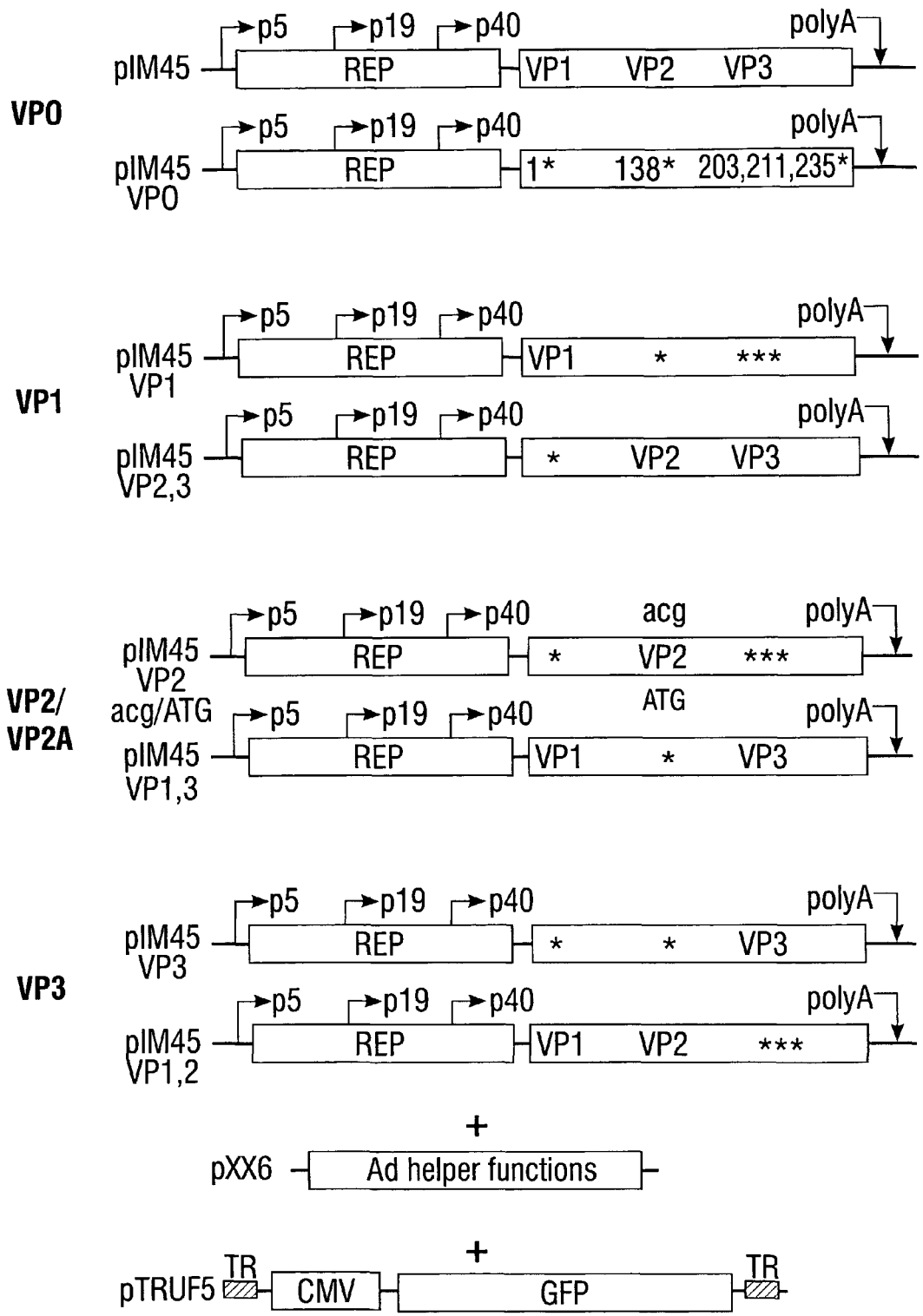

FIG. 4 shows complementation capsid plasmid groups employed to produce viable rAAV2 particle preparations. Group VP0 is a control group consisting of pIM45 and pIM45-VP0 (all capsid expression eliminated). Group VP1 is group consisting of pIM45-VP1 and pIM45-VP2,3 in which expression of VP1 is isolated. Group VP2/VP2A is group consisting of pIM45-VP2 or pIM45-VP2A and pIM45-VP1,3 in which expression of VP2 is isolated, and in case of pIM45-VP2A, VP2 expression is maximized. Group VP3 is group consisting of pIM45-VP3 and pIM45-VP1,2 in which expression of VP3 is isolated. Isolation of specific capsid proteins allows genetic modification of the isolated capsid without further modifying remaining capsids. Alternatively, genetic modification of two capsids can be accomplish without further modification of remaining capsid. These groups are cotransfected with pXX6 (Ad helper functions) and pTR-UF5 (terminal repeats flanking expression cassette with CMV promoter driving expression of GFP) to produce rAAV vectors.

Figures 1, 5A:
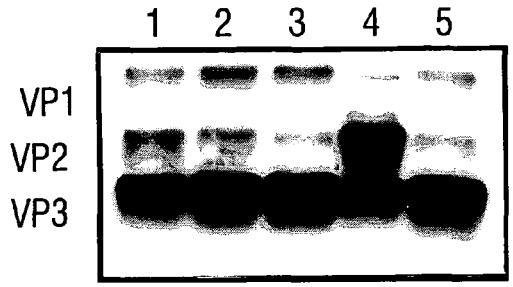
Figures 2, 5A:
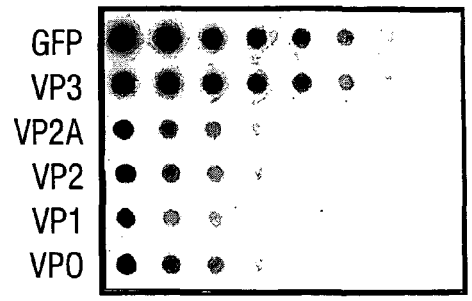
Figures 1, 5B:
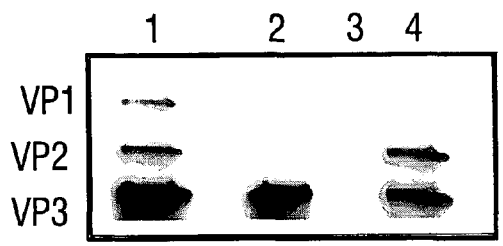
Figures 2, 5B:
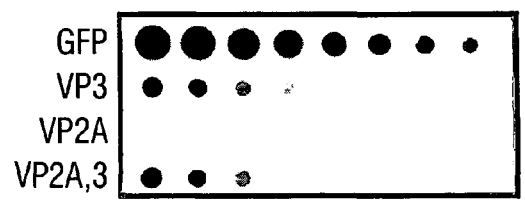

FIG. 5A-1, FIG. 5A-2, FIG. 5B-1 and FIG. 5B-2 show production and purification of rAAV2-like particles from complementation groups described in FIG. 4, FIG. 5A, right panel, shows immunoblot using B1 antibody that recognizes all three capsid proteins of purified particle stocks from Group VP0(lane 1): Group VP1 (lane 2); Group VP2 (lane 3); Group VP2A (lane 4); and Group VP3 (lanes). Note, lane 4 shows production of particle stock with increased level of VP2 protein in resultant particles composed of all three capsid proteins. FIG. 5A, Right panel shows dot blot autoradiograph of DNA extracted from same particle stocks. Aliquots from an iodixinal step gradient were with incubated with DNAseI, inactivated with EDTA, digested with proteinase K, phenol:chloroform extracted, and precipitated with ethanol. DNA was transferred to nitrocellulose and probed with radiolabelled GFP probe. FIG. 5B, left panel, shows immunoblot using B1 antibody that recognizes all three capsid proteins of purified particle stocks from transfection of pIM45-VP2A and pIM45-VP3 showing production of rAAV2-like particles composed of VP2 and VP3 with increased VP2 levels relative to VP3. FIG. 5B, right panel, shows dot blot autoradiograph of DNA extracted from same particle stocks. Aliquots from an iodixinal step gradient were with incubated with DNAseI, inactivated with EDTA, digested with proteinase K, phenol:chloroform extracted, and precipitated with ethanol. DNA was transferred to nitrocellulose and probed with radiolabelled GFP probe.

Figure 6A:
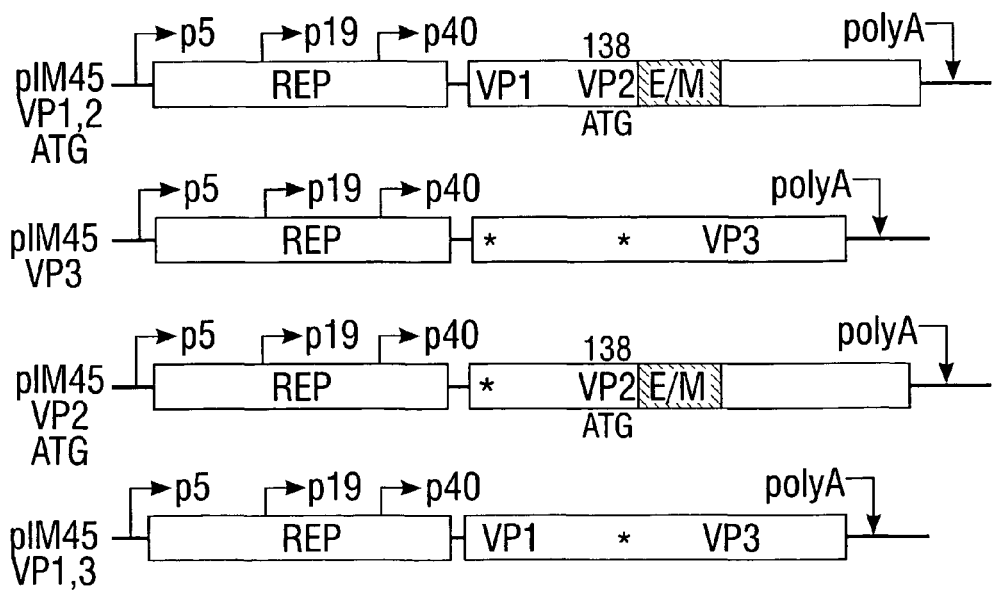
Figures 1, 6B:
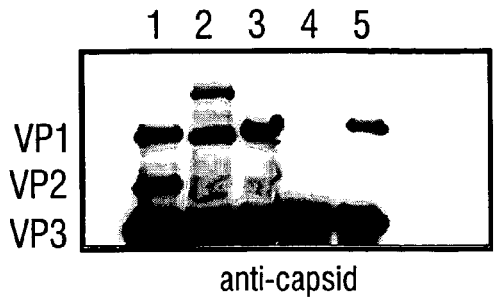
Figures 2, 6B:
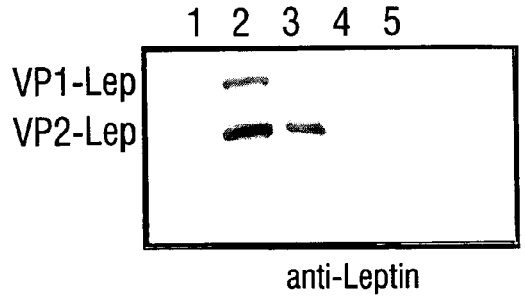
Figures 1, 6C:
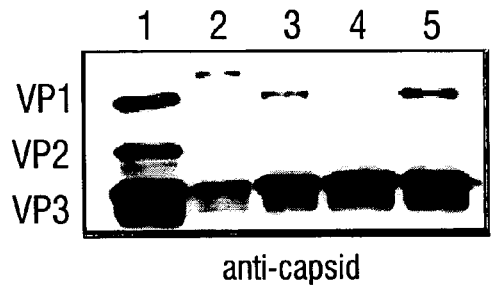
Figures 2, 6C:
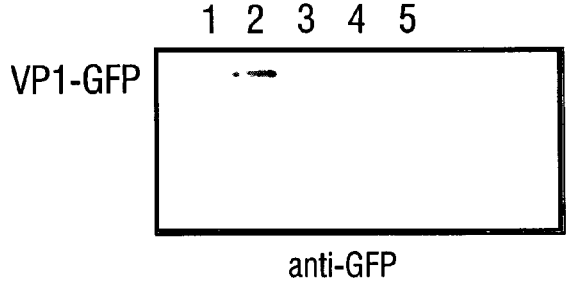

FIG. 6A, FIG. 6B-1, FIG. 6B-2, FIG. 6C-1 and FIG. 6C-2 depict production of rAAV2-like particles with large peptide insertions in VP1 and VP2 capsid proteins. FIG. 6A shows production scheme for insertion of large peptides in VP1 and VP2 (top) involves insertion of peptide immediately after amino acid 138 in a plasmid that expresses only VP1 and VP2 (pIM45-VP1,2A) and complementing this plasmid with plasmid, pIM45-VP3, to produce particles. Production scheme for insertion of large peptides only in VP2 (bottom) involves insertion of peptide immediately after amino acid 138 in a plasmid that expresses only VP2 (pIM45-VP2A) and complementing this plasmid with plasmid, pIM45-VP1,3 to produce particles. FIG. 6B shows immunoblot of purified rAAV2-like particles produced by above production schemes with protein, leptin, inserted in VP1 and VP2 or only in VP2. FIG. 6B, left panel, shows immunoblot probed with antibody recognizing all three capsids proteins. FIG. 6B, right panel, shows immunoblot probed with antibody recognizing inserted peptide, leptin. Both panels: Lane 1: pIM45; Lane 2: pIM45-VP1,2A-Leptin/pIM45-VP3; Lane 3: pIM45-VP2A-Leptin/pIM45-VP1,3; Lane 4: pIM45-VP3 only; pIM45-VP1,3 only. FIG. 6C shows immunoblot of purified rAAV2-like particles produced by above production schemes with protein, GFP, inserted in VP1 and VP2 or only in VP2. FIG. 6C, left panel, shows immunoblot probed with antibody recognizing all three capsids proteins. FIG. 6C, right panel, shows immunoblot probed with antibody recognizing inserted peptide, GFP. Both panels: Lane 1: pIM45; Lane 2: pIM45-VP1,2A-GFP/pIM45-VP3; Lane 3: pIM45-VP2A-GFP/pIM45-VP1,3; Lane 4: pIM45-VP3 only; pIM45-VP1,3 only.

Figure 7:
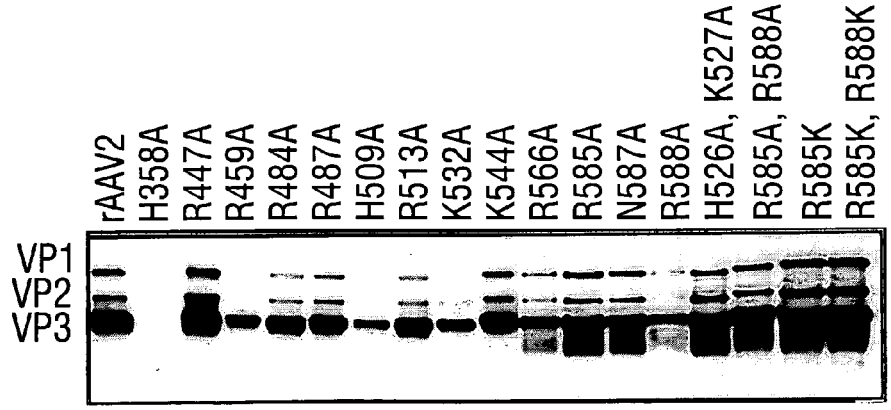

FIG. 7 shows Western blot of iodixanol virus stocks. Equal volumes of virus stock were separated by 10% SDS-PAGE and analyzed by Western blot using the B1 antibody.

Figure 8:
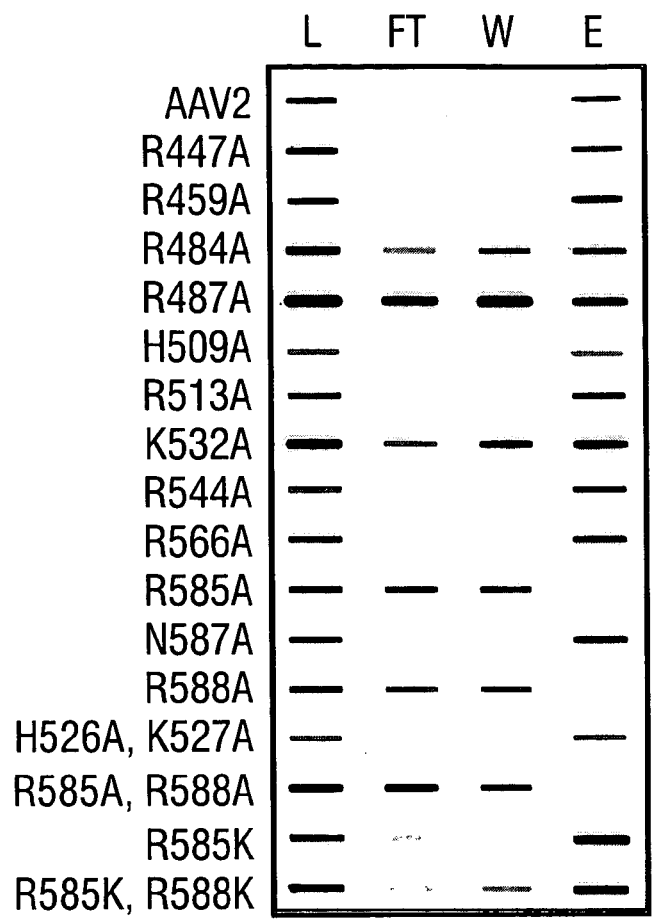

FIG. 8 shows heparin-agarose binding profiles of mutant capsids. Approximately $5 \times 10^{10}$ particles were applied to 500 µl of heparin-agarose affinity matrix at a 100 mM NaCl concentration, washed extensively with the loading buffer, and bound capsids were eluted with 2 M NaCl. Pooled fractions were denatured and slot blotted onto nitrocellulose for immunodetection with mAb B1. For each mutant, L is the total amount of iodixanol purified virus that was loaded onto the heparin agarose column; FT is the total virus that flowed through the column, W is the wash; E, eluate.

Figure 9A:
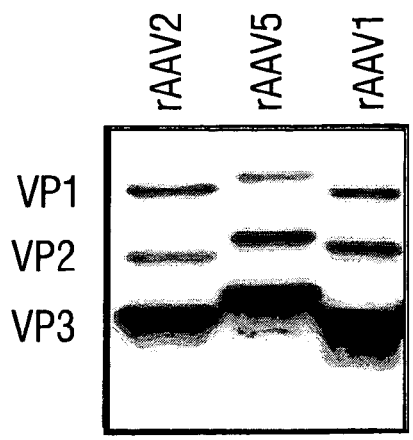
Figure 9B:
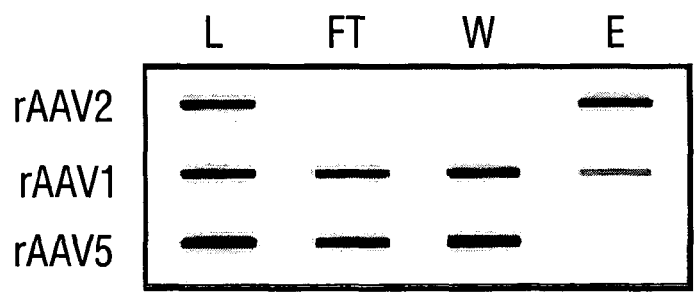

FIG. 9A and FIG. 9B show production and purification of AAV serotypes. FIG. 9A shows equivalent amounts of iodixanol purified AAV1, AAV2 and AAV5 were separated by 10% PAGE and analyzed by Western blot using the B1 antibody. FIG. 9B shows heparin-agarose binding properties of AAV2, AAV1 and AAV5. Abbreviations are the same as FIG. 8.

Figure 10:
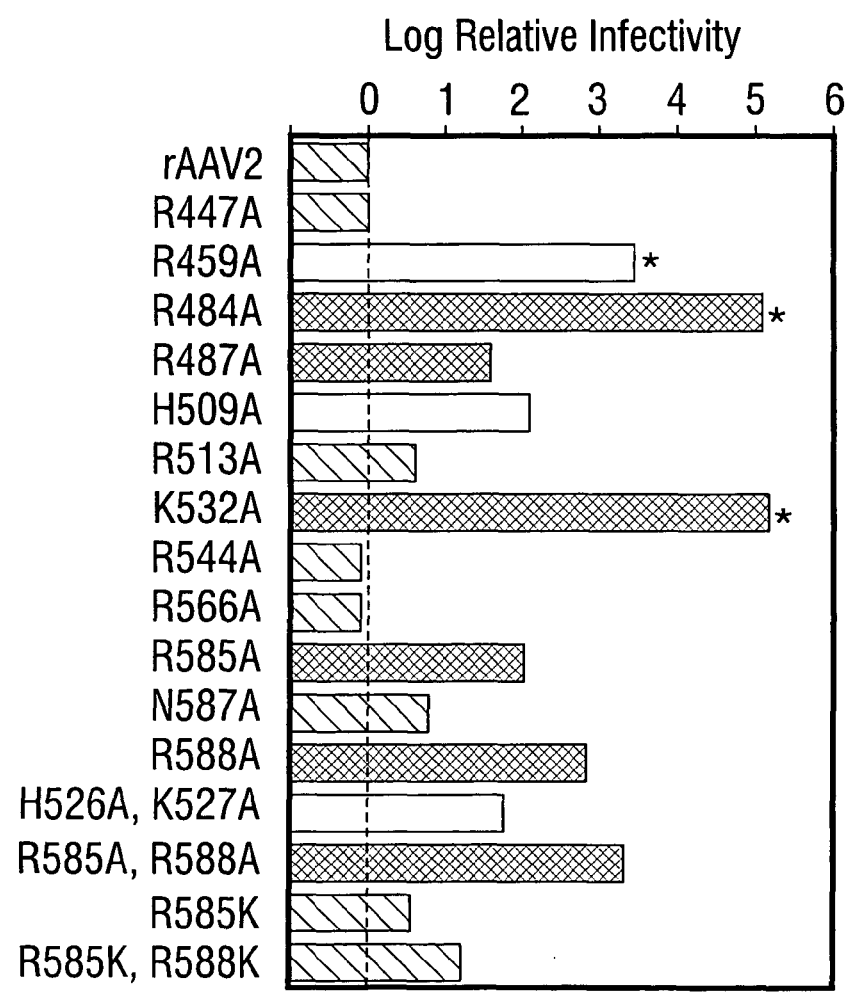

FIG. 10 shows particle-to-infectivity ratios of mutants relative to wild type. The particle-to-infectivity ratio for each mutant was calculated by dividing the average genomic titer by the average green cell assay titer (Table 2). The P/I ratio of each mutant was then normalized to wild type by dividing the P/I of each mutant by the P/I of wild type rAAV2, and the $log_{10}$ value of the ratio was plotted. Wild type, therefore, equals one and is indicated by the dashed line. Grey bars, mutant viruses with infectivity comparable to wild type;

Black bars, mutant viruses that are heparin binding deficient; White bars, mutant viruses with an undetermined block to infectivity; Asterisks indicate those mutants for which no green cells were scored. For these mutants the green cell assay titer used was the limit of detection in the assay. Thus, the log difference is a minimum estimate.

Figure 11:
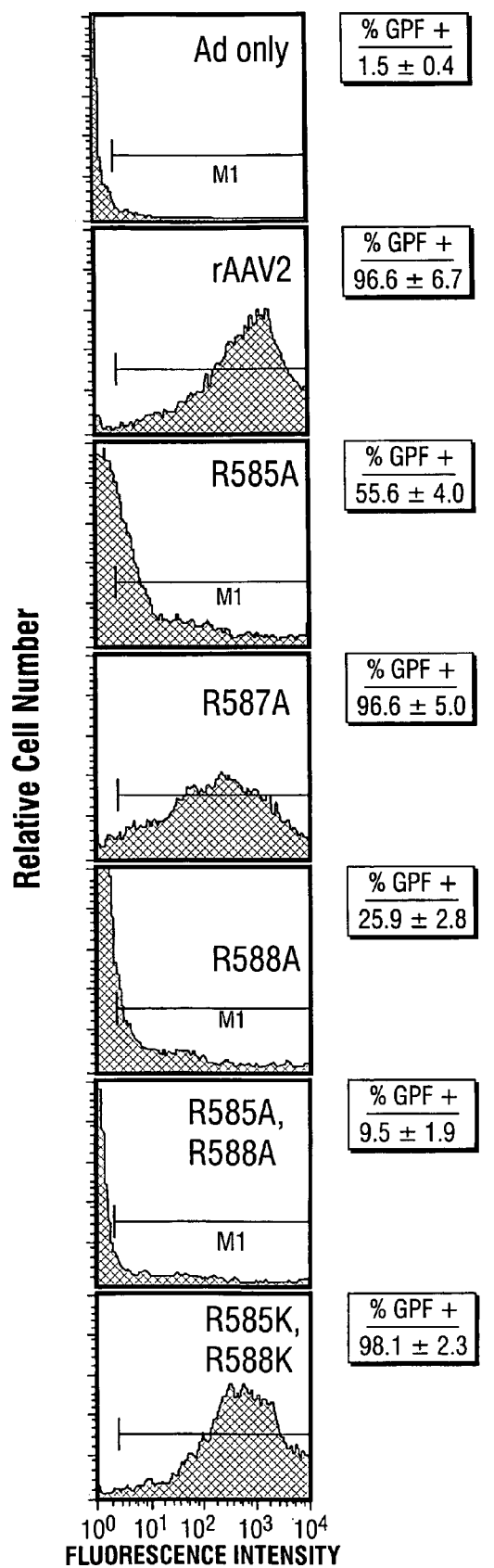

FIG. 11 shows GFP transduction ability of mutants in HeLa C12 cells. Cells were infected with wild type rAAV or mutant virus at an MOI=500 genomic particles and an Ad5 MOI=10 pfu per cell. Twenty-four hours post infection cells were fixed with 2% paraformaldehyde and the number of GFP positive cells was determined by FACS analysis.

FIG. 12A and FIG. 12B show binding and uptake of rAAV2 and R585A/R588A genomes in Hela C12 cells. FIG. 12A shows $10^6$ cells were infected with rAAV2 or R585/R588A at an MOI=100 or 1000 genome containing particles per cell, respectively. At the indicated times, infection media was removed and saved. The cells were washed and harvested, and Hirt DNA was extracted from both the infection media and the cell pellet. Southern analysis was performed using an $[\alpha\text{-}^{32}P]$-dATP labeled GFP probe. FIG. 12b shows the percent bound/internalized DNA was calculated by dividing the total DNA present in both the media and the cell pellet by the amount bound/internalized for each time point. The average of three determinations is shown. Error bars indicate a standard deviation.

Figure 13D:
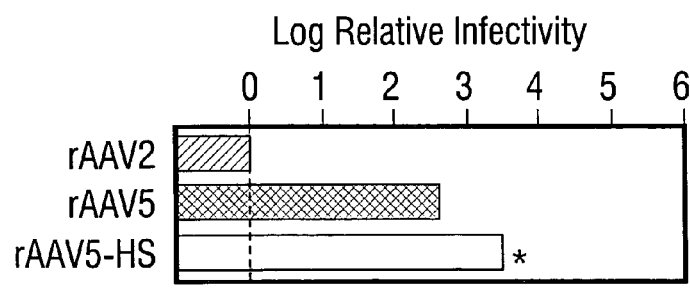

FIG. 13A, FIG. 13B, FIG. 13C and FIG. 13D show modifying the heparin binding properties of AAV5. FIG. 13A shows alignment of AAV2 amino acid residues 585 through 590 to residues predicted by amino acid alignment to be structurally equivalent in AAV5. FIG. 13B shows Western blot of iodixanol virus stocks. Equal volumes of virus were separated by 10% SDS-PAGE and analyzed by Western blot using the B1 antibody. FIG. 13C shows novel heparin binding properties of AAV5-HS. Heparin-agarose binding was performed as described in FIG. 8. See FIG. 8 for abbreviations. FIG. 17D shows, the log of the particle-to-infectivity ratio of the rAAV5 variants normalized to wild type rAAV2 as described in FIG. 10.

Figure 14:
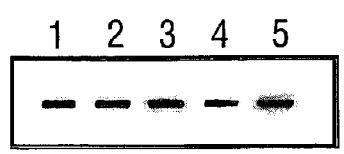

FIG. 14 shows an immunoslotblot of total capsid protein from novel production system following standard purification procedures. Immunoslotblot was probed with anti-VP1, 2,3 monoclonal antibody. 1. pIM45/pIM45-VP0; 2. pIM45-VP1/pIM45-VP2,3; 3. pIM45-VP2acg/pIM45-VP1,3; 4. pIM45-VP2atg/pIM45-VP1,3; 5. pIM45-VP3/pIM45-VP1, 2.

Figure 15:
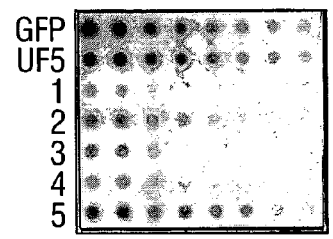
Figure 16A:
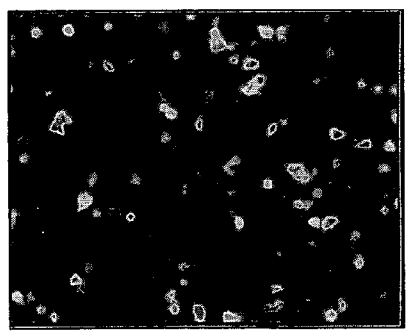
Figure 16B:
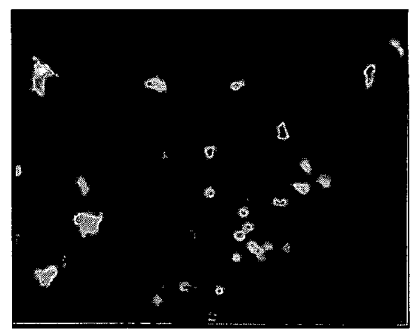
Figure 16C:
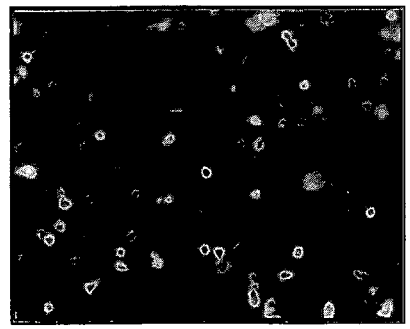
Figure 16D:
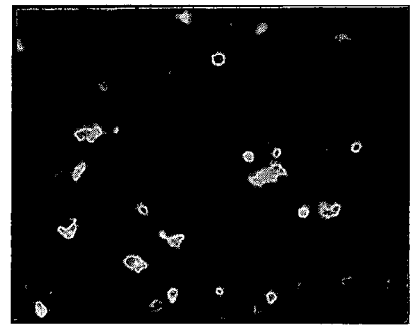

FIG. 15 shows a dot blot autoradiograph of DNA extracted from pTR-UF5 and system plasmid combinations. Numbering scheme is the same as described in FIG. 14. Equal volume aliquots from an iodixinol step gradient were with incubated with DNAseI, inactivated with EDTA, digested with proteinase K, phenol:chloroform extracted, and precipitated with ethanol. DNA was transferred to nitrocellulose and probed with radiolabeled GFP probe.

FIG. 16 shows the in viva transduction ability of recombinant AAV vectors produced using various system components. GFP fluorescence microscopy was performed on Hela C12 infected at an MOI of 1000 genomes/cell 24 hours post infection.

Figure 17A:
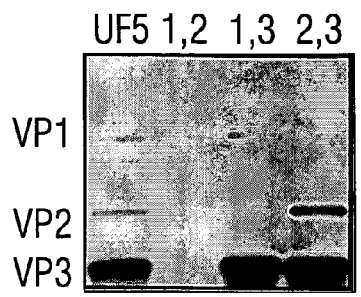
Figure 17B:
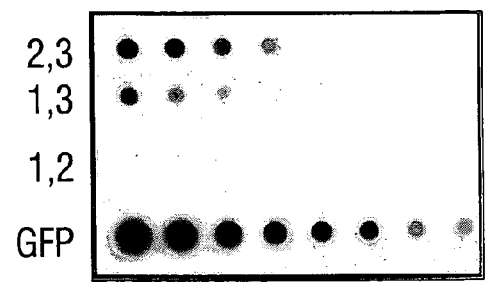
Figure 18A:
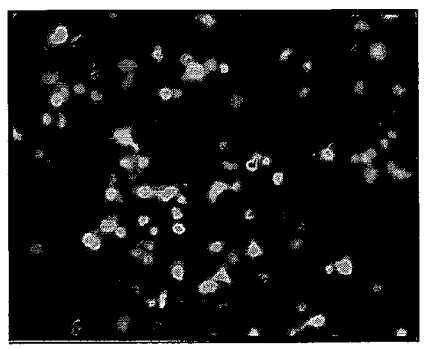
Figure 18B:
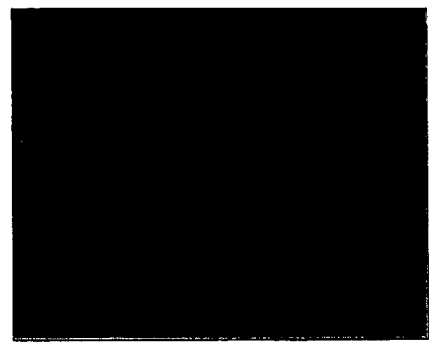
Figure 18C:
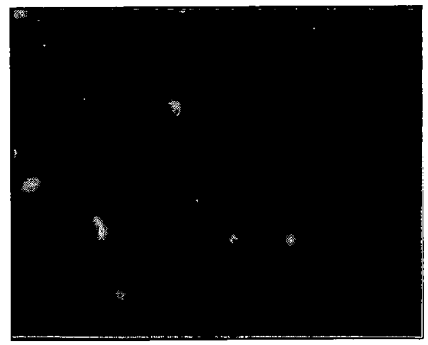
Figure 18D:

FIG. 17A and FIG. 17B show the Immunoblot and dot blot autoradiograph of virions produced from pTR-UF5; pIM45-VP1,2; pIM45-VP1,3; and pIM45-VP2,3 plasmids following standard purification protocols. The capsid proteins VP1, VP2, and VP3 are indicated. No virions were obtained in 40% iodixanol fraction from plasmid pIM45-VP1,2.

FIG. 18A, FIG. 18B, FIG. 18C and FIG. 18D show the in viva transduction ability of recombinant AAV vectors containing only two capsid proteins. GFP fluorescence microscopy was performed on Hela C12/24 hours post infection.

Figure 19:
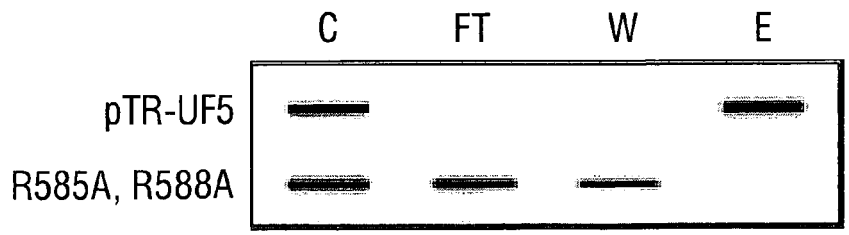
Figure 20:
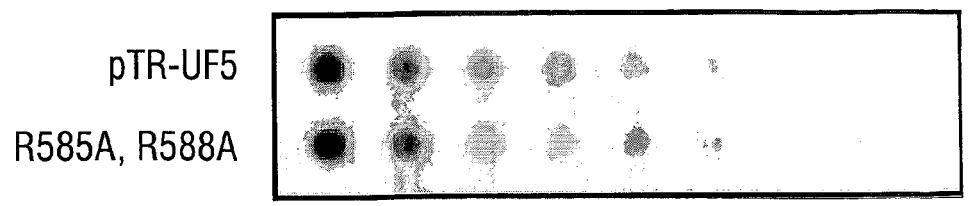
Figure 21A:
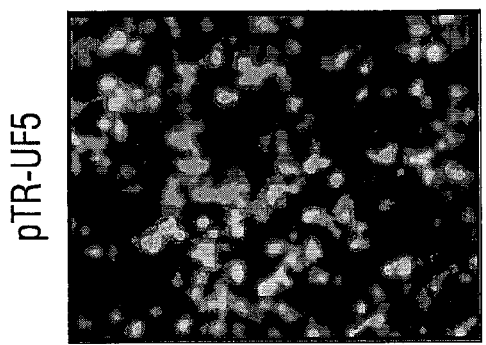
Figure 21B:
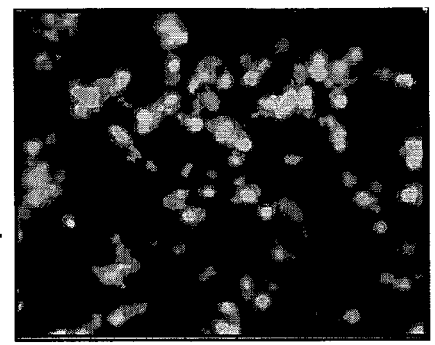
Figure 21C:
Figure 21D:
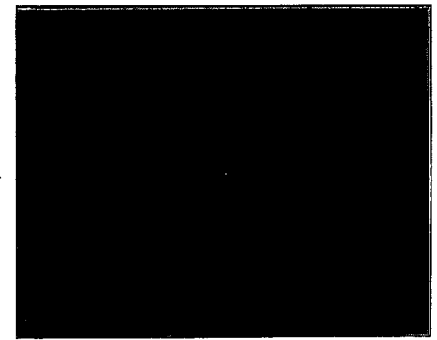

FIG. 19 depicts an immunoblot of protein fractions collected from iodixinol purified passed over a heparin-agarose column. Immunoblot was probed with anti-VP1,2,3 monoclonal antibody. C, 5E+10 virus particles loaded directly onto blot, FT, flowthrough fraction, W, wash fraction, E, 2M NaCl fraction FIG. 20 shows a dot blot autoradiograph of DNA extracted from pTR-UF5 and rAAV R585A, R588A. Equal volume aliquots from an iodixinal step gradient were with incubated with DNAseI, inactivated with EDTA, digested with proteinase K, phenol:chloroform extracted, and precipitated with ethanol. DNA was transferred to nitrocellulose and probed with radiolabeled GFP probe.

FIG. 21A, FIG. 21B, FIG. 21C and FIG. 21D show the in viva transduction ability of pTR-UF5 and R585A, R588A. GFP fluorescence microscopy was performed on Hela C12 and HEK 293 cells infected at an MOI of 1000 genomes/cell 24 hours post infection.

Figure 22:
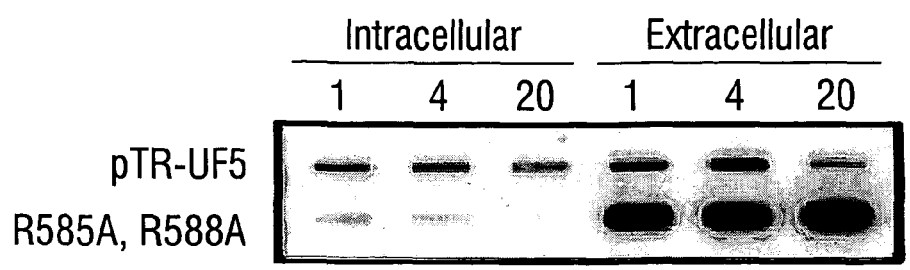

FIG. 22 shows a slot blot autoradiograph of an in viva DNA tracking time course experiment of pTR-UF5, rAAV R585A, R588A. Media and cells infected with pTR-UF5 and rAAV R585A, R588A were collected at 1,4. and 20 hours post infection. Hirt DNA was extracted, transferred to nitrocellulose and probed with a radiolabeled GFP probe.

Figure 23:
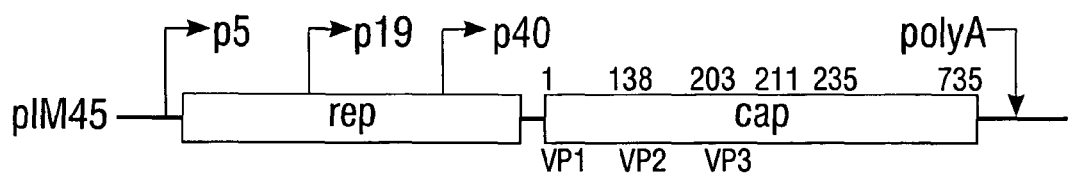

FIG. 23 shows a schematic diagram of the pIM45 vector showing the rep and cap sequences.

4. DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

4.1 rAAV Type 2

The adeno-associated virus type 2 (AAV2) is a small, non-enveloped parvovirus that has received considerable attention as a gene therapy vector (see, e.g., Muzyczka and Berns, 2001). The capsid has a diameter of approximately 20 nm formed by an icosahedral lattice with T=1 symmetry (60 structurally equivalent subunits). In purified virions, three structural proteins, VP1, VP2, and VP3 with molecular masses of 87, 73, and 62 Kda, respectively, are present in a molar ratio of 1:1:18 (Buller and Rose, 1978). mRNAs encoding capsid proteins are synthesized from a single open reading frame and use alternative splicing and start codons to produce three VP proteins that share an identical 532 carboxyl-terminal amino acid domain (Becerra et al., 1988; Becerra et al., 1985), with VP2 and VP3 containing successive amino terminal truncations of VP1.

The atomic structure of the AAV2 capsid has been determined to a resolution of 3.5 angstroms (Xie et al., 2002). In this model, sixty copies of VP3 minus 14 amino terminal residues are present in an icosahedral arrangement. The VP3 protein contains 8 anti-parallel β-strands that adopt a barreloid structure similar to capsid proteins of other non-enveloped viruses. Loops of variable length connect the interior β-barrel scaffold and extend outwards to form the capsid surface. Cryo-electron microscopy of empty AAV2 particles generated a surface density map that described holes, spikes and canyon features similar to those found in other parvoviruses (Kronenberg et al., 2001). Before the crystal structure was available, several alternative methods were investigated in an attempt to localize specific regions of the capsid. Neutralizing antibody screening of peptide sequences derived from VP1 found multiple antigenic determinants distributed on the capsid exterior in both linear and conformation dependent forms (Moskalenko et al., 2000). Computer modeling of AAV structure based on the known atomic structure of the related canine parvovirus coupled with genetic modification of the capsid identified several positions that were on the surface of the capsid and could tolerate insertions and substitutions (Grifman et al., 2001; Nicklin et al., 2001; Rabinowitz et al., 1999; Ried et al., 2002; Shi et al., 2001; Wu et al., 2000; Yang et al., 1998).

Cell membrane binding and entry initiates all viral infections. Non-enveloped viruses rely on membrane bound extracellular receptors for attachment to the cell membrane. AAV2 has evolved a dynamic and multistep infectious entry pathway that utilizes the abundantly expressed heparan sulfate proteoglycan (HSPG) as its primary target (Summerford and Samulski, 1998). Two co-receptors, αVβ5 integrin and basic fibroblast growth factor receptor (bFGFR) have been identified, which act as secondary receptors that may stabilize virus attachment or participate during internalization (Duan et al., 1999; Qing et al., 1999; Summerford et al., 1999). HSPG is a macromolecule expressed by many cell types and is a component of the extracellular matrix of most tissues (see, e.g., Hileman et al., 1998; Mull9oy and Linhardt, 2001). Attached to the core protein are glycosaminoglycan side chains heparin and heparin sulfate (HS). These carbohydrate polymers are formed by disaccharide repeats consisting of alternating N-acetylglucosamine and iduronic acid residues in a α-1,4 linkage. The saccharides can be modified by N-sulfation as well as 2-O and 6-O-sulfation to impart a dense overall negative charge at physiological pH. As a result, HS interacts with an extensive range of proteins primarily by electrostatic attraction between the electron dense sulfate groups and a cluster of positively charged amino acids. Two linear consensus-binding sequences, XBBXBX (SEQ ID NO:1) and XBBBXXBX (SEQ ID NO:2), and a conformation dependent sequence, TXXBXXTBXXXTBB (SEQ ID NO:3), (where B is any basic amino acids including His, Lys or Arg and X is any hydropathic amino acid and T is a turn) have been reported (Hileman et al., 1998). Although HSPG is thought to participate in attachment during the infectious process of numerous human viruses (Liu and Thorp, 2002), information about the molecular mechanisms of these interactions is limited. A report describing the atomic structure of the foot and mouth disease virus co-crystallized with a HS pentasaccharide is available and serves as the only model defined at the atomic level that describes the molecular interaction between a non-enveloped icosahedral virus and HS (Fry et al., 1999).

Several laboratories have attempted to retarget AAV vectors to non-permissive cell types by inserting sequences coding for short foreign peptides into VP3. Interestingly, insertions at position 587, including an L14 integrin binding peptide, a myc tag, an IgG binding domain truncation of protein A and an endothelial cell targeting peptide, abolished the natural heparin binding ability of virus capsids with these alterations (Girod et al., 1999; Grifman et al., 2001; Nicklin et al., 2001; Ried et al., 2002; Shi et al., 2001). Similarly, an alanine repeat insertion at position 509, an L14 peptide insertion at position 520, a hemagluttinin tag insertion at positions 522 and 591, and peptides derived from the human luteinizng hormone receptor and the bovine papilloma virus at inserted positions 520 and 584, respectively, have been reported to disrupt heparin binding (Shi et al., 2001; Wu et al., 2000). Curiously, alanine substitutions of acidic residues between 561 and 565 also reduced heparin binding, suggesting that nearby basic residues were affected (Wu et al., 2000). Finally, a substitution mutation of two arginines and a glutamine at positions 585, 588, and 587, respectively, binds poorly to heparin-agarose (Wu et al., 2000). Taken together, these genetic modifications suggested two potential heparin-binding loci that cluster between positions 509-522 and 561-591.

4.2 rAAV Capsid Proteins

Supramolecular assembly of 60 individual capsid protein subunits into a non-enveloped, T-1 icosahedral lattice capable of protecting a 4.7 kb single-stranded DNA genome is a critical step in the life-cycle of the helper-dependent human parvovirus, adeno-associated virus2 (AAV2). The mature 20 nm diameter AAV2 particle is composed of three structural proteins designated VP1, VP2, and VP3 (molecular masses of 87, 73, and 62 kDa respectively) in a ratio of 1:1:18. Based on its symmetry and these molecular weight estimates, of the 60 capsid proteins comprising the particle, three are VP1 proteins, three are VP2 proteins, and fifty-four are VP3 proteins. The employment of three structural proteins makes AAV serotypes unique among parvoviruses, as all others known package their genomes within icosahedral particles composed of only two capsid proteins. The anti-parallel β-strand barreloid arrangement of these 60 capsid proteins results in a particle with a defined tropism that is highly resistant to degradation.

The AAV2 genome contains two large open reading frames (ORF), rep and cap, flanked by inverted terminal repeats. The AAV2 capsid proteins are produced in an overlapping fashion from the cap ORF; arising through alternative mRNA splicing of the transcript (initiated at the p40 promoter), with subsequent alternative translational start codon usage. A common stop codon is employed for all three capsid proteins. Correct capsid protein stoichiometry is maintained by translating VP1 from the 2.4 KB mRNA, while VP2 and VP3 arise from the 2.3-kB mRNA using a weaker ACG start codon for VP2 protein production with resultant read-through translation for the production of the VP3 protein. Differing only in the length of their N-terminus, these proteins are produced such that the amino acid sequence of VP3 is contained within the significantly less abundant and longer VP1 and VP2 proteins. As such, VP1's unique 137 amino acid N-terminal extension of VP2 contains a phospholipase enzymatic activity important for viral infectivity. Similarly, VP2 extends the N-terminus of VP3 by 64 amino acids with this VP1/VP2 overlap region possessing a putative nuclear localization signal (NLS) involved in the nuclear translocation of VP2. The VP3 region common to all three capsid proteins contains the critical β-barrel structural motifs characteristic of all parvoviruses and particle surface loops involved in determining viral tropism.

While specific activities have been attributed to regions of an individual AAV2 capsid protein, the role of each capsid protein in the structural formation of the particle is less clear. Early studies in which all AAV2 capsid expression was eliminated revealed that capsid protein expression is required for the accumulation of single stranded genomes. It follows that AAV2 particle assembly occurs within the nucleus, and a putative NLS for VP2 has been localized to the VP1/VP2 overlap region in transfected COS cells.

In the absence of VP1 expression, this study suggested a major role of VP2 is the nuclear localization of VP3. However, since VP1 was deleted in this study, one cannot rule out that VP1 has the ability to nuclear localize VP3. Site-directed missense mutagenesis of the individual capsid proteins' start codons suggested that infectious particles are obtained only when all three capsid proteins are present. In contrast, later genetic analysis demonstrated that in the absence of VP1, VP2 and VP3 are able to encapsidate progeny genomes. Similarly, in vitro assembly of purified individual AAV capsid proteins demonstrated that VP2 and VP3 could form an AAV2-like particle. Baculovirus expression of the AAV2 capsid proteins within SF9 cells suggests an absolute requirement for VP2, although this study failed to eliminate VP3-like fragments produced by the VP2-baculovirus. However, it is feasible that studies of AAV2 assembly in baculovirus have subtle differences with particles assembled in mammalian cells.

An examination of the assembly process of the related autonomous canine parvovirus, CPV, in baculovirus observed significantly more aggregation of capsid proteins in insect cells. In addition, the results of the baculovirus and NLS studies have the caveat that they were performed in the absence of AAV2 Rep proteins, Ad helper gene functions, and a replicating AAV2 genome. Furthermore, the p40 promoter in these studies does not control AAV2 capsid protein expression, resulting in altered stoichiometry of the available capsid protein pool. Indeed, the above concerns seem warranted, as a recent insertional mutagenesis study of the AAV2 cap ORF, using standard AAV2 production protocols, reported the purification of an AAV2-like particle composed of only the VP3 protein. Therefore, despite the uncertainty of the precise role of VP1 and VP2 in particle formation, the evidence thus far suggests that the VP3 protein is absolutely required for the formation of an AAV2 particle. Finally, co localization studies of AAV2 assembly in 293 cells demonstrated an interaction of AAV2 Rep and capsid proteins with Ad proteins and the replicating genome in the nucleus, thus, supporting a current model of AAV2 assembly which proposes nucleoplasmic formation of empty particles with subsequent maturation of the particle as a result of Rep 52/40 mediated translocation of capsid protein associated single stranded genomes into the preformed particles.

4.3 Genetic Modification of rAAV Capsid Proteins

Great interest in the assembly, structure, and mutability of the AAV2 particle results from its promise as a recombinant gene delivery vehicle (rAAV2) in vivo. Essential to the clinical development of rAAV2 vectors for gene therapy is the ability to target specific tissue types. Manipulation of the rAAV2 particle in order to control its cellular receptor interactions is essential for vector targeting. The feasibility of various targeting strategies based on AAV cap ORF mutagenesis is currently an area of active investigation. A better understanding of the AAV2 particle surface architecture through systematic scanning-alanine and insertional mutagenesis of the AAV cap ORF and recent publication of the AAV2 crystal structure has identified several amino acid regions on the surface of the particle that tolerate sequence alteration without loss of capsid stability or integrity.

However, small changes in charge, sequence, and/or position of the mutation can result in dramatic changes in the mutant particle phenotype. One limitation in sequence mutation of the overlapping cap ORF is that mutation of only one capsid protein across its entire sequence is currently not possible. The full potential in manipulation of the particle is not reached with direct alteration of regions of capsid overlap. Predicted surface regions of capsid overlap leading to defective phenotypes upon mutagenesis may allow production of viable particles if such mutations were only in one or two of the capsid proteins. An additional degree of flexibility in modifying the rAAV2 particle would result from the ability to mutate the entire coding region of a specific capsid protein without altering the remaining two capsid proteins. Indeed, while mutations in the C-terminus of the VP3 region have been reported to be completely defective in particle formation following insertion of HA and 6×His tags into the overlapping cap ORF, a recent report focusing on the purification of rAAV2 particles demonstrated that the C-terminus of VP3 is capable of accepting a 6×His tag if VP1 and VP2 are not altered. This rAAV2 production strategy involved expressing VP1 and VP2 from one construct, and expressing the VP3-6×His fusion protein from a CMV promoter in a second plasmid. In the absence of the isolation of a specific capsid protein's expression, the N-terminal 137 amino acids of VP1 are the only region of the cap ORF where mutations are restricted to a single capsid protein. Successful insertions within this region have included HA and serpin. The VP1/VP2 overlap region (amino acid 138-202) also has been receptive to sequence modification. Insertions in this region have included HA, serpin and luetinizing hormone receptor ligand sequences immediately following amino acid 138 in the cap ORF.

The success of inserting sequences to the VP1 and VP1/VP2 regions may be due in part to less disruption of the integrity of the particle compared to insertion in the VP3 region of capsid overlap (amino acid 203-735). It is important to note that these mutant particles would require further mutation of the putative heparin-binding motif to restrict infection to the target cell. Not surprisingly, since it is the longest region of capsid protein overlap, contains many critical structural motifs, and targeting sequences in this region have 60 representatives in the rAAV particle, mutations in the VP3 region of the AAV2 cap ORF have resulted in the highest number of defective phenotypes. Yet, one location within the VP3 region has received much attention for the successful insertion of small targeting sequences in all three capsid proteins (amino acid 587). One major advantage of targeting insertions to this position is that the resultant mutant particle also has lost the ability to bind its native receptor. Viable mutations in the VP3 region of the cap ORF have been restricted in size (<30 amino acids).

One caveat of creating genetically-targeted rAAV2 particles, is the consideration that many cell surface receptors have ligands whose coding sequence are much larger than those successfully inserted directly into the overlapping cap ORF. Due to the modest size of this ORF (~2 kB), the insertion of larger peptide sequences into the capsid coding sequences may result in serious disruption of splicing, read-through translation, capsid structure and/or stability. The insertion of large sequences into the rAAV2 particle have been limited to a study involving the fusion of the CD34 single chain antibody coding sequence with the N-termini of the individual capsid proteins following isolation of their expression to separate CMV promoters. Viable CD34-retargeted rAAV particles of extremely low titer were produced only when this fusion was to VP2 protein, and co-expression of wild-type VP2 protein was required. Nonetheless, the fusion of large peptide sequences to the N-terminus of VP2 does not interfere with the incorporation of this capsid protein into the rAAV2 particle.

4.4 Wild-Type Aav2 Binds to Heparan Sulfate Proteoglycan

The adeno-associated virus type-2 (AAV2) uses heparan sulfate proteoglycan (HSPG) as its primary cellular receptor. In order to identify amino acids within the capsid of AAV2 that contribute to HSPG association, biochemical information about heparin/heparin sulfate (HS), AAV serotype protein sequence alignments, and data from previous capsid studies was used to select residues for mutagenesis. In the present invention, charged-to-alanine substitution mutagenesis was performed on individual and combinations of basic residues for the production and purification of recombinant viruses that contained a GFP reporter gene cassette. Intact capsids were assayed for their ability to bind to heparin-agarose in vitro and virions that packaged DNA were assayed for their ability to transduce normally permissive cell lines. It was found that mutation of arginine residues at position 585 or 588 eliminated binding to heparin-agarose. Mutation of residues R484, R487, and K532 showed partial binding to heparin-agarose. A general correlation between heparin-agarose binding and infectivity was observed as measured by GFP transduction; however, a subset of mutants that partially bound heparin-agarose (R484A and K532A) were completely non-infectious, suggesting that they had additional blocks to infectivity that were unrelated to heparin binding. Conservative mutation of positions R585 and R588 to lysine slightly reduced heparin-agarose binding, and had comparable effects on infectivity. Substitution of AAV2 residues 585 through 590 into a location predicted to be structurally equivalent in AAV5 generated a hybrid virus that bound to heparin-agarose efficiently, was able to package DNA, but was non-infectious. Taken together, these suggest that residues R585 and R588 are primarily responsible for heparin sulfate binding and mutation of these residues has little effect on other aspects of the viral life cycle.

Computer modeling using the AAV2 VP3 atomic coordinates revealed that residues which contribute to heparin binding form a cluster of five basic amino acids on the surface of each three-fold axis of symmetry related spike. Three other kinds of mutants were found as well. Mutants, R459A, H509A and H526A/K527A bound heparin as well as wild type but were defective for transduction. Another mutant, H358A, was defective for capsid assembly. Finally, a mutant R459A produced significantly lower levels of full capsids, suggesting a packaging defect.

4.5 Pharmaceutical Compositions

The genetic constructs of the present invention may be prepared in a variety of compositions, and may also be formulated in appropriate pharmaceutical vehicles for administration to human or animal subjects. The AAV molecules of the present invention and compositions comprising them provide new and useful therapeutics for the treatment, control, and amelioration of symptoms of a variety of disorders. Moreover, pharmaceutical compositions comprising one or more of the nucleic acid compounds disclosed herein, provide significant advantages over existing conventional therapies—namely, (1) their reduced side effects, (2) their increased efficacy for prolonged periods of time, (3) their ability to increase patient compliance due to their ability to provide therapeutic effects following as little as a single administration of the selected therapeutic AAV composition to affected individuals. Exemplary pharmaceutical compositions and methods for their administration are discussed in significant detail hereinbelow.

The invention also provides compositions comprising one or more of the disclosed vectors, expression systems, virions, viral particles; or mammalian cells. As described hereinbelow, such compositions may further comprise a pharmaceutical excipient, buffer, or diluent, and may be formulated for administration to an animal, and particularly a human being. Such compositions may further optionally comprise a liposome, a lipid, a lipid complex, a microsphere, a microparticle, a nanosphere, or a nanoparticle, or may be otherwise formulated for administration to the cells, tissues, organs, or body of a mammal in need thereof. Such compositions may be formulated for use in therapy, such as for example, in the amelioration, prevention, or treatment of conditions such as peptide deficiency, polypeptide deficiency, tumor, cancer or other malignant growth, neurological dysfunction, autoimmune diseases, lupus, cardiovascular disease, pulmonary disease, ischemia, stroke, cerebrovascular accidents, diabetes and diseases of the pancreas, neural diseases, including Alzheimer's, Huntington's, Tay-Sach's, and Parkinson's diseases, memory loss, trauma, motor impairment, and the like, as well as biliary, renal or hepatic disease or dysfunction, as well as musculoskeletal diseases including, for example, arthritis, cystic fibrosis (CF), amyotrophic lateral sclerosis (ALS), multiple sclerosis (MS), muscular dystrophy (MD), and such like, to name only a few.

In certain embodiments, the present invention concerns formulation of one or more of the rAAV compositions disclosed herein in pharmaceutically acceptable solutions for administration to a cell or an animal, either alone or in combination with one or more other modalities of therapy, and in particular, for therapy of human cells, tissues, and diseases affecting man.

It will also be understood that, if desired, nucleic acid segments, RNA, DNA or PNA compositions that express one or more of therapeutic gene products may be administered in combination with other agents as well, such as, e.g., proteins or polypeptides or various pharmaceutically-active agents, including one or more systemic or topical administrations of therapeutic polypeptides, biologically active fragments, or variants thereof. In fact, there is virtually no limit to other components that may also be included, given that the additional agents do not cause a significant adverse effect upon contact with the target cells or host tissues. The rAAV compositions may thus be delivered along with various other agents as required in the particular instance. Such compositions may be purified from host cells or other biological sources, or alternatively may be chemically synthesized as described herein. Likewise, such compositions may further comprise substituted or derivatized RNA, DNA, or PNA compositions.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound(s) in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the AAV vector-based therapeutic constructs in suitably formulated pharmaceutical compositions disclosed herein either subcutaneously, intraocularly, intravitreally, parenterally, intravenously, intracerebroventricularly, intramuscularly, intrathecally, orally, intraperitoneally, by oral or nasal inhalation, or by direct injection to one or more neural cells, nervous tissues, or even by direct injection or administration to the brain, CNS or to the peripheral nervous system. The methods of administration may also include those modalities as described in U.S. Pat. No. 5,543,158; U.S. Pat. No. 5,641,515 and U.S. Pat. No. 5,399,363 (each specifically incorporated herein by reference in its entirety). Solutions of the active compounds as freebase or pharmacologically acceptable salts may be prepared in sterile water and may also suitably mixed with one or more surfactants, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms of the AAV-based viral compositions suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active AAV vector-delivered therapeutic polypeptide-encoding DNA fragments in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The AAV vector compositions disclosed herein may also be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human, and in particular, when administered to the human eye. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The amount of AAV compositions and time of administration of such compositions will be within the purview of the skilled artisan having benefit of the present teachings. It is likely, however, that the administration of therapeutically-effective amounts of the disclosed compositions may be achieved by a single administration, such as for example, a single injection of sufficient numbers of infectious particles to provide therapeutic benefit to the patient undergoing such treatment. Alternatively, in some circumstances, it may be desirable to provide multiple, or successive administrations of the AAV vector compositions, either over a relatively short, or a relatively prolonged period of time, as may be determined by the medical practitioner overseeing the administration of such compositions. For example, the number of infectious particles administered to a mammal may be on the order of about $10^7$, $10^8$, $10^9$, $10^{10}$, $10^{11}$, $10^{12}$, $10^{13}$, or even higher, infectious particles/ml given either as a single dose, or divided into two or more administrations as may be required to achieve therapy of the particular disease or disorder being treated. In fact, in certain embodiments, it may be desirable to administer two or more different AAV vector compositions,

4.6 Liposome-, Nanocapsule-, and Microparticle-Mediated Delivery

In certain embodiments, the inventors contemplate the use of liposomes, nanocapsules, microparticles, microspheres, lipid particles, vesicles, and the like, for the introduction of the compositions of the present invention into suitable host cells. In particular, the rAAV vector delivered gene therapy compositions of the present invention may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art (see for example, Couvreur et al., 1977; Couvreur, 1988; Lasic, 1998; which describes the use of liposomes and nanocapsules in the targeted antibiotic therapy for intracellular bacterial infections and diseases). Recently, liposomes were developed with improved serum stability and circulation half-times (Gabizon and Papahadjopoulos, 1988; Allen and Chonn, 1987; U.S. Pat. No. 5,741,516, specifically incorporated herein by reference in its entirety). Further, various methods of liposome and liposome like preparations as potential drug carriers have been reviewed (Takakura, 1998; Chandran et al., 1997; Margalit, 1995; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally resistant to transfection by other procedures including T cell suspensions, primary hepatocyte cultures and PC 12 cells (Renneisen et al., 1990; Muller et al., 1990). In addition, liposomes are free of the DNA length constraints that are typical of viral-based delivery systems. Liposomes have been used effectively to introduce genes, drugs (Heath and Martin, 1986; Heath et al., 1986; Balazsovits et al., 1989; Fresta and Puglisi, 1996), radiotherapeutic agents (Pikul et al., 1987), enzymes (Imaizumi et al., 1990a; Imaizumi et al., 1990b), viruses (Faller and Baltimore, 1984), transcription factors and allosteric effectors (Nicolau and Gersonde, 1979) into a variety of cultured cell lines and animals. In addition, several successful clinical trails examining the effectiveness of liposome-mediated drug delivery have been completed (Lopez-Berestein et al., 1985a; 1985b; Coune, 1988; Sculier et al., 1988). Furthermore, several studies suggest that the use of liposomes is not associated with autoimmune responses, toxicity or gonadal localization after systemic delivery (Mori and Fukatsu, 1992).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

In addition to the teachings of Couvreur et al. (1977; 1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins, such as cytochrome c, bind, deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity, and surface charge. They may persist in tissues for h or days, depending on their composition, and half lives in the blood range from min to several h. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow, and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Alternatively, the invention provides for pharmaceutically acceptable nanocapsule formulations of the AAV vector-based polynucleotide compositions of the present invention. Nanocapsules can generally entrap compounds in a stable and reproducible way (Henry-Michelland et al., 1987; Quintanar-Guerrero et al., 1998; Douglas et al., 1987). To avoid side effects due to intracellular polymeric overloading, such ultrafine particles (sized around 0.1 µm) should be designed using polymers able to be degraded in vivo. Biodegradable polyalkylcyanoacrylate nanoparticles that meet these requirements are contemplated for use in the present invention. Such particles may be are easily made, as described (Couvreur et al., 1980; Couvreur, 1988; zur Muhlen et al., 1998; Zambaux et al. 1998; Pinto-Alphandry et al., 1995 and U.S. Pat. No. 5,145,684, specifically incorporated herein by reference in its entirety).

4.7 Additional Modes of Delivery

In addition to the methods of delivery described above, the following techniques are also contemplated as alternative methods of delivering the disclosed rAAV vector based polynucleotide compositions to a target cell or animal. Sonophoresis (i.e., ultrasound) has been used and described in U.S. Pat. No. 5,656,016 (specifically incorporated herein by reference in its entirety) as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. No. 5,770,219 and U.S. Pat. No. 5,783,208) and feedback-controlled delivery (U.S. Pat. No. 5,697,899), each specifically incorporated herein by reference in its entirety.

4.8 Promoters and Enhancers

Recombinant AAV vectors form important aspects of the present invention. The term "expression vector or construct" means any type of genetic construct containing a nucleic acid in which part or all of the nucleic acid encoding sequence is capable of being transcribed. In preferred embodiments, expression only includes transcription of the nucleic acid, for example, to generate a biologically-active therapeutic peptides, polypeptides, proteins, antisense molecules, or catalytic RNA ribozymes from a transcribed gene.

Particularly useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene.

In preferred embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with an cytokine or serpin-encoding gene in its natural environment. Such promoters may include promoters normally associated with other genes, and/or promoters isolated from any bacterial, viral, eukaryotic, or mammalian cell.

Naturally, it will be important to employ a promoter that effectively directs the expression of the serpin or cytokine-encoding DNA segment in the cell type, organism, or even animal, chosen for expression. The use of promoter and cell type combinations for protein expression is generally known to those of skill in the art of molecular biology, for example, see Sambrook et al. (1989), incorporated herein by reference. The promoters employed may be constitutive, or inducible, and can be used under the appropriate conditions to direct high-level expression of the introduced DNA segment, or the promoters may direct tissue- or cell-specific expression of the therapeutic constructs, such as, for example, an islet cell- or pancreas-specific promoter such as the insulin promoter.

At least one module in a promoter functions to position the start site for RNA synthesis. The best-known example of this is the TATA box, but in some promoters lacking a TATA box, such as the promoter for the mammalian terminal deoxy-nucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid is not believed to be critical, so long as it is capable of expressing the serpin or cytokine-polypeptide encoding nucleic acid segment in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter, such as a CMV or an HSV promoter. In certain aspects of the invention, β-actin, and in particular, chicken β-actin promoters have been shown to be particularly preferred for certain embodiments of the invention.

In various other embodiments, the human cytomegalovirus (CMV) immediate early gene promoter, the SV40 early promoter and the Rous sarcoma virus long terminal repeat can be used to obtain high-level expression of transgenes. The use of other viral or mammalian cellular or bacterial phage promoters that are well known in the art to achieve expression of a transgene is contemplated as well, provided that the levels of expression are sufficient for a given purpose. A variety of promoter elements have been described in Tables 1 and 2 that may be employed, in the context of the present invention, to regulate the expression of the present serpin or cytokine-encoding nucleic acid segments comprised within the recombinant AAV vectors of the present invention.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

TABLE 1

ILLUSTRATIVE PROMOTER AND ENHANCER ELEMENTS

| PROMOTER/ENHANCER | REFERENCES |
|---|---|
| Immunoglobulin Heavy Chain | Banerji et al., 1983; Gilles et al., 1983; Grosschedl and Baltimore, 1985; Atchinson and Perry, 1986, 1987; Imler et al., 1987; Weinberger et al., 1984; Kiledjian et al., 1988; Porton et al.; 1990 |
| Immunoglobulin Light Chain | Queen and Baltimore, 1983; Picard and Schaffner, 1984 |
| T-Cell Receptor | Luria et al., 1987; Winoto and Baltimore, 1989; Redondo et al.; 1990 |
| HLA DQ a and DQ β | Sullivan and Peterlin, 1987 |
| β-Interferon | Goodbourn et al., 1986; Fujita et al., 1987; Goodbourn and Maniatis, 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-Dra | Sherman et al., 1989 |
| β-Actin | Kawamoto et al., 1988; Ng et al.; 1989 |
| Muscle Creatine Kinase | Jaynes et al., 1988; Horlick and Benfield, 1989; Johnson et al., 1989 |
| Prealbumin (Transthyretin) | Costa et al., 1988 |
| Elastase I | Omitz et al., 1987 |
| Metallothionein | Karin et al., 1987; Culotta and Hamer, 1989 |
| Collagenase | Pinkert et al., 1987; Angel et al., 1987 |
| Albumin Gene | Pinkert et al., 1987; Tronche et al., 1989, 1990 |
| α-Fetoprotein | Godbout et al., 1988; Campere and Tilghman, 1989 |
| t-Globin | Bodine and Ley, 1987; Perez-Stable and Constantini, 1990 |
| β-Globin | Trudel and Constantini, 1987 |
| e-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $\alpha_{1\text{-}Antitrypain}$ | Latimer et al., 1990 |
| H2B (TH2B) Histone | Hwang et al., 1990 |
| Mouse or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Duchenne Muscular Dystrophy | Klamut et al., 1990 |
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987; Schaffner et al., 1988 |
| Polyoma | Swartzendruber and Lehman, 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and Villarreal, 1988 |

TABLE 1-continued

ILLUSTRATIVE PROMOTER AND ENHANCER ELEMENTS

| PROMOTER/ENHANCER | REFERENCES |
|---|---|
| Retroviruses | Kriegler and Botchan, 1982, 1983; Levinson et al., 1982; Kriegler et al., 1983, 1984a, b, 1988; Bosze et al., 1986; Miksicek et al., 1986; Celander and Haseltine, 1987; Thiesen et al., 1988; Celander et al., 1988; Choi et al., 1988; Reisman and Rotter, 1989 |
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al., 1987; Stephens and Hentschel, 1987 |
| Hepatitis B Virus | Bulla and Siddiqui, 1986; Jameel and Siddiqui, 1986; Shaul and Ben-Levy, 1987; Spandau and Lee, 1988; Vannice and Levinson, 1988 |
| Human Immunodeficiency Virus | Muesing et al., 1987; Hauber and Cullan, 1988; Jakobovits et al., 1988; Feng and Holland, 1988; Takebe et al., 1988; Rosen et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukemia Virus | Holbrook et al., 1987; Quinn et al., 1989 |

TABLE 2

INDUCIBLE ELEMENTS

| ELEMENT | INDUCER | REFERENCES |
|---|---|---|
| MT II | Phorbol Ester (TFA) Heavy metals | Palmiter et al., 1982; Haslinger and Karin, 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors and Varmus, 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | Ela | Imperiale and Nevins, 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | Ela, SV40 Large T Antigen | Taylor et al., 1989; Taylor and Kingston, 1990a, b |
| Proliferin | Phorbol Ester-TPA | Mordacq and Linzer, 1989 |
| Tumor Necrosis Factor | FMA | Hensel et al., 1989 |
| Thyroid Stimulating Hormone a Gene | Thyroid Hormone | Chatterjee et al., 1989 |

As used herein, the terms "engineered" and "recombinant" cells are intended to refer to a cell into which an exogenous DNA segment, such as DNA segment that leads to the transcription of a biologically-active serpin or cytokine polypeptide or a ribozyme specific for such a biologically-active serpin or cytokine polypeptide product, has been introduced. Therefore, engineered cells are distinguishable from naturally occurring cells, which do not contain a recombinantly introduced exogenous DNA segment. Engineered cells are thus cells having DNA segment introduced through the hand of man.

To express a biologically-active serpin or cytokine encoding gene in accordance with the present invention one would prepare an rAAV expression vector that comprises a biologically-active serpin or cytokine polypeptide-encoding nucleic acid segment under the control of one or more promoters. To bring a sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded polypeptide. This is the meaning of "recombinant expression" in this context. Particularly preferred recombinant vector constructs are those that comprise an rAAV vector. Such vectors are described in detail herein.

4.9 Mutagenesis and Preparation of Modified Nucleotide Compositions

In certain embodiments, it may be desirable to prepared modified nucleotide compositions, such as, for example, in the generation of the nucleic acid segments that encode either parts of the AAV vector itself, or the promoter, or even the therapeutic gene delivered by such rAAV vectors. Various means exist in the art, and are routinely employed by the artisan to generate modified nucleotide compositions.

Site-specific mutagenesis is a technique useful in the preparation and testing of sequence variants by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector that includes within its sequence a DNA sequence encoding the desired ribozyme or other nucleic acid construct. An oligonucleotide primer bearing the desired mutated sequence is synthetically prepared. This primer is then annealed with the single-stranded DNA preparation, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected nucleic acid sequences using site-directed mutagenesis is provided as a means of producing potentially useful species and is not meant to be limiting, as there are other ways in which sequence variants may be obtained. For example, recombinant vectors encoding the desired gene may be treated with mutagenic agents, such as hydroxylamine, to obtain sequence variants.

4.10 Nucleic Acid Amplification

In certain embodiments, it may be necessary to employ one or more nucleic acid amplification techniques to produce the nucleic acid segments of the present invention. Various methods are well-known to artisans in the field, including for example, those techniques described herein:

Nucleic acid, used as a template for amplification, may be isolated from cells contained in the biological sample according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA and is used directly as the template for amplification.

Pairs of primers that selectively hybridize to nucleic acids corresponding to the ribozymes or conserved flanking regions are contacted with the isolated nucleic acid under conditions that permit selective hybridization. The term "primer", as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (e.g., Affymax technology).

A number of template dependent processes are available to amplify the marker sequences present in a given template sample. One of the best-known amplification methods is the polymerase chain reaction (referred to as PCR™), which is described in detail in U.S. Pat. No. 4,683,195, U.S. Pat. No. 4,683,202 and U.S. Pat. No. 4,800,159 (each of which is incorporated herein by reference in its entirety).

Briefly, in PCR™, two primer sequences are prepared that are complementary to regions on opposite complementary strands of the marker sequence. An excess of deoxynucleoside triphosphates is added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al. (1989). Alternative methods for reverse transcription utilize thermostable, RNA-dependent DNA polymerases. These methods are described in Int. Pat. Appl. Publ. No. WO 90/07641 (specifically incorporated herein by reference). Polymerase chain reaction methodologies are well known in the art.

Another method for amplification is the ligase chain reaction ("LCR"), disclosed in EPA No. 320 308, and incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qβ Replicase (QβR), described in Int. Pat. Appl. No. PCT/US87/00880, incorporated herein by reference, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[α-thio]-triphosphates in one strand of a restriction site may also be useful in the amplification of nucleic acids in the present invention.

Strand Displacement Amplification (SDA), described in U.S. Pat. Nos. 5,455,166, 5,648,211, 5,712,124 and 5,744,311, each incorporated herein by reference, is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in Int. Pat. Appl. No. PCT/US89/01025, each of which is incorporated herein by reference in its entirety, may be used in accordance with the present invention. In the former application, "modified" primers are used in a PCR™-like, template- and enzyme-dependent synthesis. The primers may be modified by labeling with a capture moiety (e.g., biotin) and/or a detector moiety (e.g., enzyme). In the latter application, an excess of labeled probes is added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR Gingeras et al., Int. Pat. Appl. Publ. No. WO 88/10315, incorporated herein by reference. In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer that has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNAs are reverse transcribed into single stranded DNA, which is then converted to double stranded DNA, and then transcribed once again with an RNA polymerase such as T7 or SP6. The resulting products, whether truncated or complete, indicate target specific sequences. Davey et al., EPA No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., Int. Pat. Appl. Publ. No. WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR™" (Frohman, 1990, specifically incorporated herein by reference).

Methods based on ligation of two (or more) oligonucleotides in the presence of nucleic acid having the sequence of the resulting "di-oligonucleotide," thereby amplifying the di-oligonucleotide, may also be used in the amplification step of the present invention.

Following any amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods (see e.g., Sambrook et al., 1989).

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography.

Amplification products must be visualized in order to confirm amplification of the marker sequences. One typical visualization method involves staining of a gel with ethidium bromide and visualization under LW light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art and can be found in many standard books on molecular protocols. See Sambrook et al., 1989. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

4.11 Methods of Nucleic Acid Delivery and DNA Transfection

In certain embodiments, it is contemplated that one or more RNA, DNA, PNAs and/or substituted polynucleotide compositions disclosed herein will be used to transfect an appropriate host cell. Technology for introduction of PNAs, RNAs, and DNAs into cells is well known to those of skill in the art.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Wong and Neumann, 1982; Fromm et al., 1985; Tur-Kaspa et al., 1986; Potter et al., 1984; Suzuki et al., 1998; Vanbever et al., 1998), direct microinjection (Capecchi, 1980; Harland and Weintraub, 1985), DNA-loaded liposomes (Nicolau and Sene, 1982; Fraley et al., 1979; Takakura, 1998) and lipofectamine-DNA complexes, cell sonication (Fechheimer et al., 1987), gene bombardment using high velocity microprojectiles (Yang et al., 1990; Klein et al., 1992), and receptor-mediated transfection (Curiel et al., 1991; Wagner et al., 1992; Wu and Wu, 1987; Wu and Wu, 1988). Some of these techniques may be successfully adapted for in vivo or ex vivo use.

4.12 Expression Vectors

The present invention contemplates a variety of AAV-based expression systems, and vectors. In one embodiment the preferred AAV expression vectors comprise at least a first nucleic acid segment that encodes a therapeutic peptide, protein, or polypeptide. In another embodiment, the preferred AAV expression vectors disclosed herein comprise at least a first nucleic acid segment that encodes an antisense molecule. In another embodiment, a promoter is operatively linked to a sequence region that encodes a functional mRNA, a tRNA, a ribozyme or an antisense RNA.

As used herein, the term "operatively linked" means that a promoter is connected to a functional RNA in such a way that the transcription of that functional RNA is controlled and regulated by that promoter. Means for operatively linking a promoter to a functional RNA are well known in the art.

The choice of which expression vector and ultimately to which promoter a polypeptide coding region is operatively linked depend directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the functional RNA to which it is operatively linked.

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

A variety of methods have been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

4.13 Biological Functional Equivalents

Modification and changes to the structure of the polynucleotides and polypeptides of wild-type rAAV vectors to provide the improved rAAV virions as described in the present invention to obtain functional viral vectors that possess desirable characteristics, particularly with respect to improved delivery of therapeutic gene constructs to selected mammalian cell, tissues, and organs for the treatment, prevention, and prophylaxis of various diseases and disorders, as well as means for the amelioration of symptoms of such diseases, and to facilitate the expression of exogenous therapeutic and/or prophylactic polypeptides of interest via rAAV vector-mediated gene therapy. As mentioned above, one of the key aspects of the present invention is the creation of one or more mutations into specific polynucleotide sequences that encode one or more of the therapeutic agents encoded by the disclosed rAAV constructs. In certain circumstances, the resulting polypeptide sequence is altered by these mutations, or in other cases, the sequence of the polypeptide is unchanged by one or more mutations in the encoding polynucleotide to produce modified vectors with improved properties for effecting gene therapy in mammalian systems.

When it is desirable to alter the amino acid sequence of a polypeptide to create an equivalent, or even an improved, second-generation molecule, the amino acid changes may be achieved by changing one or more of the codons of the encoding DNA sequence, according to Table 3.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the polynucleotide sequences disclosed herein, without appreciable loss of their biological utility or activity.

TABLE 3

| Amino Acids | | | Codons | | | |
|---|---|---|---|---|---|---|
| Alanine | Ala | A | GCA GCC | GCG GCU | | |
| Cysteine | Cys | C | UGC UGU | | | |
| Aspartic acid | Asp | D | GAC GAU | | | |
| Glutamic acid | Glu | E | GAA GAG | | | |
| Phenylalanine | Phe | F | UUC UUU | | | |
| Glycine | Gly | G | GGA GGC | GGG GGU | | |
| Histidine | His | H | CAC CAU | | | |
| Isoleucine | Ile | I | AUA AUC | AUU | | |
| Lysine | Lys | K | AAA AAG | | | |
| Leucine | Leu | L | UUA UUG | CUA CUC | CUG CUU | |
| Methionine | Met | M | AUG | | | |
| Asparagine | Asn | N | AAC AAU | | | |
| Proline | Pro | P | CCA CCC | CCG CCU | | |
| Glutamine | Gln | Q | CAA CAG | | | |
| Arginine | Arg | R | AGA AGG | CGA CGC | CGG CGU | |
| Serine | Ser | S | AGC AGU | UCA UCC | UCG UCU | |
| Threonine | Thr | T | ACA ACC | ACG ACU | | |
| Valine | Val | V | GUA GUC | GUG GUU | | |
| Tryptophan | Trp | W | UGG | | | |
| Tyrosine | Tyr | Y | UAC UAU | | | |

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those that are within ±1 are particularly preferred, and those within ±0.5 are even more particularly preferred. It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take several of the foregoing characteristics into consideration are well known to those of skill in the art and include: arginine and lysine; glutamate and aspartate; serine and threonine; glutamine and asparagine; and valine, leucine and isoleucine.

4.14 Therapeutic and Diagnostic Kits

The invention also encompasses one or more of the modified rAAV vector compositions described herein together with one or more pharmaceutically-acceptable excipients, carriers, diluents, adjuvants, and/or other components, as may be employed in the formulation of particular rAAV-polynucleotide delivery formulations, and in the preparation of therapeutic agents for administration to a mammal, and in particularly, to a human. In particular, such kits may comprise one or more of the disclosed rAAV compositions in combination with instructions for using the viral vector in the treatment of such disorders in a mammal, and may typically further include containers prepared for convenient commercial packaging.

As such, preferred animals for administration of the pharmaceutical compositions disclosed herein include mammals, and particularly humans. Other preferred animals include murines, bovines, equines, porcines, canines, and felines. The composition may include partially or significantly purified rAAV compositions, either alone, or in combination with one or more additional active ingredients, which may be obtained from natural or recombinant sources, or which may be obtainable naturally or either chemically synthesized, or alternatively produced in vitro from recombinant host cells expressing DNA segments encoding such additional active ingredients.

Therapeutic kits may also be prepared that comprise at least one of the compositions disclosed herein and instructions for using the composition as a therapeutic agent. The container means for such kits may typically comprise at least one vial, test tube, flask, bottle, syringe or other container means, into which the disclosed rAAV composition(s) may be placed, and preferably suitably aliquoted. Where a second therapeutic polypeptide composition is also provided, the kit may also contain a second distinct container means into which this second composition may be placed. Alternatively, the plurality of therapeutic biologically active compositions may be prepared in a single pharmaceutical composition, and may be packaged in a single container means, such as a vial, flask, syringe, bottle, or other suitable single container means. The kits of the present invention will also typically include a means for containing the vial(s) in close confinement for commercial sale, such as, e.g., injection or blow-molded plastic containers into which the desired vial(s) are retained.

4.15 Ribozymes

As mentioned above, one aspect of the invention concerns the use of the modified capsid vectors to deliver catalytic RNA molecules (ribozymes) to selected mammalian cells and tissues to effect a reduction or elimination of expression of one or more native DNA or mRNA molecules, so as to prevent or reduce the amount of the translation product of such mRNAs. Ribozymes are biological catalysts consisting of only RNA. They promote a variety of reactions involving RNA and DNA molecules including site-specific cleavage, ligation, polymerization, and phosphoryl exchange (Cech, 1989; Cech, 1990). Ribozymes fall into three broad classes: (1) RNAse P, (2) self-splicing introns, and (3) self-cleaving viral agents. Self-cleaving agents include hepatitis delta virus and components of plant virus satellite RNAs that sever the RNA genome as part of a rolling-circle mode of replication. Because of their small size and great specificity, ribozymes have the greatest potential for biotechnical applications. The ability of ribozymes to cleave other RNA molecules at specific sites in a catalytic manner has brought them into consideration as inhibitors of viral replication or of cell proliferation and gives them potential advantage over antisense RNA. Indeed, ribozymes have already been used to cleave viral targets and oncogene products in living cells (Koizumi et al., 1992; Kashani-Sabet et al., 1992; Taylor and Rossi, 1991; von-Weizsacker et al., 1992; Ojwang et al., 1992; Stephenson and Gibson, 1991; Yu et al., 1993; Xing and Whitton, 1993; Yu et al., 1995; Little and Lee, 1995).

Two kinds of ribozymes have been employed widely, hairpins and hammerheads. Both catalyze sequence-specific cleavage resulting in products with a 5' hydroxyl and a 2',3'-cyclic phosphate. Hammerhead ribozymes have been used more commonly, because they impose few restrictions on the target site. Hairpin ribozymes are more stable and, consequently, function better than hammerheads at physiologic temperature and magnesium concentrations.

A number of patents have issued describing various ribozymes and methods for designing ribozymes. See, for example, U.S. Pat. Nos. 5,646,031; 5,646,020; 5,639,655; 5,093,246; 4,987,071; 5,116,742; and 5,037,746, each specifically incorporated herein by reference in its entirety. However, the ability of ribozymes to provide therapeutic benefit in vivo has not yet been demonstrated.

Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 (specifically incorporated herein by reference) reports that certain ribozymes can act as endonucleases with a sequence-specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

Six basic varieties of naturally occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., 1992). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or *Neurospora* VS RNA motif Examples of hammerhead motifs are described by Rossi et al. (1992). Examples of hairpin motifs are described by Hampel et al. (Eur. Pat. Appl. Publ. No. EP 0360257), Hampel and Tritz (1989), Hampel et al. (1990) and U.S. Pat. No. 5,631,359 (specifically incorporated herein by reference). An example of the hepatitis δ virus motif is described by Perrotta and Been (1992); an example of the RNaseP motif is described by Guerrier-Takada et al. (1983); *Neurospora* VS RNA ribozyme motif is described by Collins (Saville and Collins, 1990; Saville and Collins, 1991; Collins and Olive, 1993); and an example of the Group I intron is described in U.S. Pat. No. 4,987,071 (specifically incorporated herein by reference). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

In certain embodiments, it may be important to produce enzymatic cleaving agents that exhibit a high degree of specificity for the RNA of a desired target, such as one of the sequences disclosed herein. The enzymatic nucleic acid molecule is preferably targeted to a highly conserved sequence region of a target mRNA. Such enzymatic nucleic acid molecules can be delivered exogenously to specific cells as required, although in preferred embodiments the ribozymes are expressed from DNA or RNA vectors that are delivered to specific cells.

Small enzymatic nucleic acid motifs (e.g., of the hammerhead or the hairpin structure) may also be used for exogenous delivery. The simple structure of these molecules increases the ability of the enzymatic nucleic acid to invade targeted regions of the mRNA structure.

Alternatively, catalytic RNA molecules can be expressed within cells from eukaryotic promoters (e.g., Scanlon et al., 1991; Kashani-S abet et al., 1992; Dropulic et al., 1992; Weerasinghe et al., 1991; Ojwang et al., 1992; Chen et al., 1992; Sarver et al., 1990). Those skilled in the art realize that any ribozyme can be expressed in eukaryotic cells from the appropriate DNA vector. The activity of such ribozymes can be augmented by their release from the primary transcript by a second ribozyme (Int. Pat. Appl. Publ. No. WO 93/23569, and Int. Pat. Appl. Publ. No. WO 94/02595, both hereby incorporated by reference; Ohkawa et al., 1992; Taira et al., 1991; and Ventura et al., 1993).

Ribozymes may be added directly, or can be complexed with cationic lipids, lipid complexes, packaged within liposomes, or otherwise delivered to target cells. The RNA or RNA complexes can be locally administered to relevant tissues ex vivo, or in vivo through injection, aerosol inhalation, infusion pump or stent, with or without their incorporation in biopolymers.

Ribozymes may be designed as described in Int. Pat. Appl. Publ. No. WO 93/23569 and Int. Pat. Appl. Publ. No. WO 94/02595 (each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Hammerhead or hairpin ribozymes may be individually analyzed by computer folding (Jaeger et al., 1989) to assess whether the ribozyme sequences fold into the appropriate secondary structure, as described herein. Those ribozymes with unfavorable intramolecular interactions between the binding arms and the catalytic core are eliminated from consideration. Varying binding arm lengths can be chosen to optimize activity. Generally, at least 5 or so bases on each arm are able to bind to, or otherwise interact with, the target RNA.

Ribozymes of the hammerhead or hairpin motif may be designed to anneal to various sites in the mRNA message, and can be chemically synthesized. The method of synthesis used follows the procedure for normal RNA synthesis as described in Usman et al. (1987) and in Scaringe et al. (1990) and makes use of common nucleic acid protecting and coupling groups, such as dimethoxytrityl at the 5'-end, and phosphoramidites at the 3'-end. Average stepwise coupling yields are typically >98%. Hairpin ribozymes may be synthesized in two parts and annealed to reconstruct an active ribozyme (Chowrira and Burke, 1992). Ribozymes may be modified extensively to enhance stability by modification with nuclease resistant groups, for example, 2'-amino, 2'-C-allyl, 2'-fluoro, 2'-o-methyl, 2'-H (for a review see e.g., Usman and Cedergren, 1992). Ribozymes may be purified by gel electrophoresis using general methods or by high-pressure liquid chromatography and resuspended in water.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Perrault et al, 1990; Pieken et al., 1991; Usman and Cedergren, 1992; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

A preferred means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells (Elroy-Stein and Moss, 1990; Gao and Huang, 1993; Lieber et al., 1993; Zhou et al., 1990). Ribozymes expressed from such promoters can function in mammalian cells (Kashani-Sabet et al., 1992; Ojwang et al., 1992; Chen et al., 1992; Yu et al., 1993; L'Huillier et al., 1992; Lisziewicz et al., 1993). Although incorporation of the present ribozyme constructs into adeno-associated viral vectors is preferred, such transcription units can be incorporated into a variety of vectors for introduction into mammalian cells, including but not restricted to, plasmid DNA vectors, other viral DNA vectors (such as adenovirus vectors), or viral RNA vectors (such as retroviral, semliki forest virus, sindbis virus vectors).

Sullivan et al. (Int. Pat. Appl. Publ. No. WO 94/02595) describes general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraocular, retinal, subretinal, intraperitoneal, intracerebroventricular, intrathecal delivery, and/or direct injection to one or more tissues of the brain. More detailed descriptions of ribozyme and rAAV vector delivery and administration are provided in Int. Pat. Appl. Publ. No. WO 94/02595 and Int. Pat. Appl. Publ. No. WO 93/23569, each specifically incorporated herein by reference.

Ribozymes and the AAV vectored-constructs of the present invention may be used to inhibit gene expression and define the role (essentially) of specified gene products in the progression of one or more neural diseases, dysfunctions, cancers, and/or disorders. In this manner, other genetic targets may be defined as important mediators of the disease. These studies lead to better treatment of the disease progression by affording the possibility of combination therapies (e.g., multiple ribozymes targeted to different genes, ribozymes coupled with known small molecule inhibitors, or intermittent treatment with combinations of ribozymes and/or other chemical or biological molecules).

4.16 Antisense Oligonucleotides

In certain embodiments, the AAV constructs of the invention will find utility in the delivery of antisense oligonucleotides and polynucleotides for inhibiting the expression of a selected mammalian mRNA in neural cells.

In the art the letters, A, G, C, T, and U respectively indicate nucleotides in which the nucleoside is Adenosine (Ade), Guanosine (Gua), Cytidine (Cyt), Thymidine (Thy), and Uridine (Ura). As used in the specification and claims, compounds that are "antisense" to a particular PNA, DNA or mRNA "sense" strand are nucleotide compounds that have a nucleoside sequence that is complementary to the sense strand. It will be understood by those skilled in the art that the present invention broadly includes oligonucleotide compounds that are capable of binding to the selected DNA or mRNA sense strand. It will also be understood that mRNA includes not only the ribonucleotide sequences encoding a protein, but also regions including the 5'-untranslated region, the 3'-untranslated region, the 5'-cap region and the intron/exon junction regions.

The invention includes compounds which are not strictly antisense; the compounds of the invention also include those oligonucleotides that may have some bases that are not complementary to bases in the sense strand provided such compounds have sufficient binding affinity for the particular DNA or mRNA for which an inhibition of expression is desired. In addition, base modifications or the use of universal bases such as inosine in the oligonucleotides of the invention are contemplated within the scope of the subject invention.

The antisense compounds may have some or all of the phosphates in the nucleotides replaced by phosphorothioates ($X=S$) or methylphosphonates ($X=CH_3$) or other $C_{1-4}$ aklphosphonates. The antisense compounds optionally may be further differentiated from native DNA by replacing one or both of the free hydroxy groups of the antisense molecule with $C_{1-4}$ alkoxy groups ($R=C_{1-4}$ alkoxy). As used herein, $C_{1-4}$ alkyl means a branched or unbranched hydrocarbon having 1 to 4 carbon-atoms.

The disclosed antisense compounds also may be substituted at the 3' and/or 5' ends by a substituted acridine derivative. As used herein, "substituted acridine," means any acridine derivative capable of intercalating nucleotide strands such as DNA. Preferred substituted acridines are 2-methoxy-6-chloro-9-pentylaminoacridine, N-(6-chloro-2-methoxyacridinyl)-O-methoxydiisopropylaminophosphinyl-3-aminopropanol, and N-(6-chloro-2-methoxyacridinyl)-O-methoxydiisopropylaminophosphinyl-5-aminopentanol. Other suitable acridine derivatives are readily apparent to persons skilled in the art. Additionally, as used herein "P(O)(O)-substituted acridine" means a phosphate covalently linked to a substitute acridine.

As used herein, the term "nucleotides" includes nucleotides in which the phosphate moiety is replaced by phosphorothioate or alkylphosphonate and the nucleotides may be substituted by substituted acridines.

In one embodiment, the antisense compounds of the invention differ from native DNA by the modification of the phosphodiester backbone to extend the life of the antisense molecule. For example, the phosphates can be replaced by phosphorothioates. The ends of the molecule may also be optimally substituted by an acridine derivative that intercalates nucleotide strands of DNA. Intl. Pat. Appl. Publ. No. WO 98/13526 and U.S. Pat. No. 5,849,902 (each specifically incorporated herein by reference in its entirety) describe a method of preparing three component chimeric antisense compositions, and discuss many of the currently available methodologies for synthesis of substituted oligonucleotides having improved antisense characteristics and/or half-life.

The reaction scheme involves $^1$H-tetrazole-catalyzed coupling of phosphoramidites to give phosphate intermediates that are subsequently reacted with sulfur in 2,6-lutidine to generate phosphate compounds. Oligonucleotide compounds are prepared by treating the phosphate compounds with thiophenoxide (1:2:2 thiophenol/triethylamine/tetrahydrofuran, room temperature, 1 hr). The reaction sequence is repeated until an oligonucleotide compound of the desired length has been prepared. The compounds are cleaved from the support by treating with ammonium hydroxide at room temperature for 1 hr and then are further deprotected by heating at about 50° C. overnight to yield preferred antisense compounds.

Selection of antisense compositions specific for a given gene sequence is based upon analysis of the chosen target sequence and determination of secondary structure, $T_m$, binding energy, relative stability, and antisense compositions were selected based upon their relative inability to form dimers, hairpins, or other secondary structures that would reduce or prohibit specific binding to the target mRNA in a host cell. Highly preferred target regions of the mRNA, are those that are at or near the AUG translation initiation codon, and those sequences that were substantially complementary to 5' regions of the mRNA. These secondary structure analyses and target site selection considerations were performed using v.4 of the OLIGO primer analysis software (Rychlik, 1997) and the BLASTN 2.0.5 algorithm software (Altschul et al., 1997).

4.17 Exemplary Definitions

In accordance with the present invention, polynucleotides, nucleic acid segments, nucleic acid sequences, and the like, include, but are not limited to, DNAs (including and not limited to genomic or extragenomic DNAs), genes, peptide nucleic acids (PNAs) RNAs (including, but not limited to, rRNAs, mRNAs and tRNAs), nucleosides, and suitable nucleic acid segments either obtained from native sources, chemically synthesized, modified, or otherwise prepared in whole or in part by the hand of man.

Unless defined otherwise, all technical and scientific terms used herein have the same meaning as commonly understood by one of ordinary skill in the art to which this invention belongs. Although any methods and compositions similar or equivalent to those described herein can be used in the practice or testing of the present invention, the preferred methods and compositions are described herein. For purposes of the present invention, the following terms are defined below:

A, an: In accordance with long standing patent law convention, the words "a" and "an" when used in this application, including the claims, denotes "one or more".

Expression: The combination of intracellular processes, including transcription and translation undergone by a polynucleotide such as a structural gene to synthesize the encoded peptide or polypeptide.

Promoter: a term used to generally describe the region or regions of a nucleic acid sequence that regulates transcription.

Regulatory Element: a term used to generally describe the region or regions of a nucleic acid sequence that regulates transcription.

Structural gene: A gene or sequence region that is expressed to produce an encoded peptide or polypeptide.

Transformation: A process of introducing an exogenous polynucleotide sequence (e.g., a vector, a recombinant DNA or RNA molecule) into a host cell or protoplast in which that exogenous nucleic acid segment is incorporated into at least a first chromosome or is capable of autonomous replication within the transformed host cell. Transfection, electroporation, and naked nucleic acid uptake all represent examples of techniques used to transform a host cell with one or more polynucleotides.

Transformed cell: A host cell whose nucleic acid complement has been altered by the introduction of one or more exogenous polynucleotides into that cell.

Transgenic cell: Any cell derived or regenerated from a transformed cell or derived from a transgenic cell, or from the progeny or offspring of any generation of such a transformed host cell.

Vector: A nucleic acid molecule (typically comprised of DNA) capable of replication in a host cell and/or to which another nucleic acid segment can be operatively linked so as to bring about replication of the attached segment. A plasmid, cosmid, or a virus is an exemplary vector.

The terms "substantially corresponds to", "substantially homologous", or "substantial identity" as used herein denotes a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared. The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides. Desirably, which highly homologous fragments are desired, the extent of percent identity between the two sequences will be at least about 80%, preferably at least about 85%, and more preferably about 90% or 95% or higher, as readily determined by one or more of the sequence comparison algorithms well-known to those of skill in the art, such as e.g., the FASTA program analysis described by Pearson and Lipman (1988).

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by the hand of man in a laboratory is naturally-occurring. As used herein, laboratory strains of rodents that may have been selectively bred according to classical genetics are considered naturally occurring animals.

As used herein, a "heterologous" is defined in relation to a predetermined referenced gene sequence. For example, with respect to a structural gene sequence, a heterologous promoter is defined as a promoter which does not naturally occur adjacent to the referenced structural gene, but which is positioned by laboratory manipulation. Likewise, a heterologous gene or nucleic acid segment is defined as a gene or segment that does not naturally occur adjacent to the referenced promoter and/or enhancer elements.

"Transcriptional regulatory element" refers to a polynucleotide sequence that activates transcription alone or in combination with one or more other nucleic acid sequences. A transcriptional regulatory element can, for example, comprise one or more promoters, one or more response elements, one or more negative regulatory elements, and/or one or more enhancers.

As used herein, a "transcription factor recognition site" and a "transcription factor binding site" refer to a polynucleotide sequence(s) or sequence motif(s) which are identified as being sites for the sequence-specific interaction of one or more transcription factors, frequently taking the form of direct protein-DNA binding. Typically, transcription factor binding sites can be identified by DNA footprinting, gel mobility shift assays, and the like, and/or can be predicted on the basis of known consensus sequence motifs, or by other methods known to those of skill in the art.

As used herein, the term "operably linked" refers to a linkage of two or more polynucleotides or two or more nucleic acid sequences in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

"Transcriptional unit" refers to a polynucleotide sequence that comprises at least a first structural gene operably linked to at least a first cis-acting promoter sequence and optionally linked operably to one or more other cis-acting nucleic acid sequences necessary for efficient transcription of the structural gene sequences, and at least a first distal regulatory element as may be required for the appropriate tissue-specific and developmental transcription of the structural gene sequence operably positioned under the control of the promoter and/or enhancer elements, as well as any additional cis sequences that are necessary for efficient transcription and translation (e.g., polyadenylation site(s), mRNA stability controlling sequence(s), etc.

The term "substantially complementary," when used to define either amino acid or nucleic acid sequences, means that a particular subject sequence, for example, an oligonucleotide sequence, is substantially complementary to all or a portion of the selected sequence, and thus will specifically bind to a portion of an mRNA encoding the selected sequence. As such, typically the sequences will be highly complementary to the mRNA "target" sequence, and will have no more than 1, 2, 3, 4, 5, 6, 7, 8, 9, or 10 base mismatches throughout the complementary portion of the sequence. In many instances, it may be desirable for the sequences to be exact matches, i.e. be completely complementary to the sequence to which the oligonucleotide specifically binds, and therefore have zero mismatches along the complementary stretch. As such, highly complementary sequences will typically bind quite specifically to the target sequence region of the mRNA and will therefore be highly efficient in reducing, and/or even inhibiting the translation of the target mRNA sequence into polypeptide product.

Substantially complementary oligonucleotide sequences will be greater than about 80 percent complementary (or "% exact-match") to the corresponding mRNA target sequence to which the oligonucleotide specifically binds, and will, more preferably be greater than about 85 percent complementary to the corresponding mRNA target sequence to which the oligonucleotide specifically binds. In certain aspects, as described above, it will be desirable to have even more substantially complementary oligonucleotide sequences for use in the practice of the invention, and in such instances, the oligonucleotide sequences will be greater than about 90 percent complementary to the corresponding mRNA target sequence to which the oligonucleotide specifically binds, and may in certain embodiments be greater than about 95 percent complementary to the corresponding mRNA target sequence to which the oligonucleotide specifically binds, and even up to and including 96%, 97%, 98%, 99%, and even 100% exact match complementary to all or a portion of the target mRNA to which the designed oligonucleotide specifically binds.

Percent similarity or percent complementary of any of the disclosed sequences may be determined, for example, by comparing sequence information using the GAP computer program, version 6.0, available from the University of Wisconsin Genetics Computer Group (UWGCG). The GAP program utilizes the alignment method of Needleman and Wunsch (1970). Briefly, the GAP program defines similarity as the number of aligned symbols (i.e., nucleotides or amino acids) that are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess (1986), (2) a penalty of 3.0 for each gap and an additional 0.10 penalty for each symbol in each gap; and (3) no penalty for end gaps.

5. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Improved rAAV Vectors Having Genetic Modifications in Specific Capsid Proteins

Given advances in purification methods for rAAV2, the requirements of the individual capsid protein species in rAAV2 particle formation were reexamined in the context of designing a novel rAAV2 production system that would allow for the modification of a specific capsid protein in regions of capsid sequence overlap. Currently, highly purified and concentrated preparations of rAAV2 particles are possible from two plasmid-based production systems. These systems differ in that one system supplies the necessary adenovirus helper functions and AAV rep and cap genes from one plasmid (pDG), while the other uses two plasmids to supply these proteins (pIM45 and pXX6). These constructs are transfected into an appropriate cell type along with a construct containing a transgene expression cassette flanked by the AAV terminal repeats (e.g., pTR-UF5). This example describes an rAAV2 production system based on modifications of the triple plasmid transfection method. In this system, the expression of a specific capsid protein is restricted to one pIM45 plasmid and complemented in trans with the remaining two capsid proteins expressed from a second pIM45 plasmid. This approach maintains expression of the capsid proteins in their genomic context while providing a platform for the genetic modification of a specific capsid protein or two of the capsid proteins across their entire coding sequence. Missense mutation of the capsid proteins' start codons generated pIM45 plasmids that express a single capsid protein: pIM45-VP1, pIM45-VP2 (ACG or ATG start codon), and pIM45-VP3. Such plasmids can be complemented with plasmids expressing the remaining 2 capsid proteins (pIM45-VP2,3, pIM45-VP1,3, and pIM45-VP1,2 (ACG or ATG start codon), respectively) in order to produce viable rAAV2 vectors. Using the system's plasmid components individually, a reevaluation of capsid protein requirements for the production of rAAV2 particles revealed that viable rAAV2-like particles are produced as long as the VP3 protein is present (VP1+2+3, VP1+3, VP2+3, and VP3 only). Focusing on large peptide insertions in the VP1 and VP2 proteins without altering the critical VP3 protein, the utility of this system is demonstrated through the production of viable rAAV2 particles containing 8-, 15-, and 29-kDa proteins inserted immediately following amino acid 138 in both VP1 and VP2 proteins or in VP2 protein alone. Finally, rAAV2-like particles can be produced with altered capsid protein stoichiometry if VP2 is significantly over expressed.

5.1.1 Construction of rAAV2 Capsid Mutant Plasmids that Express Two Capsid Proteins To isolate the expression of a specific capsid protein to one pIM45 plasmid and the remaining two capsid proteins to a second pIM45 plasmid, missense mutation of the AAV2 cap ORF start codons was employed as previously described. Using site-directed mutagenesis of a pIM45 template, the VP1 start codon was mutated to leucine to generate the construct, pIM45-VP2,3, the VP2 start codon to alanine to generate the construct, pIM45-VP1,3, and the VP3 start codon to leucine to generate the construct, pIM45-VP1,2 (FIG. 1A). Western blotting analysis of capsid protein expression in whole cell lysates 48 hours post transfection of 293 cells with these plasmids in the presence of Ad5 (MOI=10) was carried out using the B1 antibody which recognizes all three capsid proteins (FIG. 1A). As previously reported, the expression of VP1 and VP2 could be eliminated by missense mutation of their start codons (FIG. 1A, lanes 2 and 3), and, in contrast, mutation of the VP3 start codon resulted in expression of a smaller VP3-like fragment (VP3a) (FIG. 1A, lane 4). Since this construct did not eliminate all VP3-like proteins it was renamed, pIM45-M203L. In the baculovirus study of AAV particle assembly, it was suggested that mutation of the VP3 start codon allows translational initiation to occur downstream at the next available ATG codon with correct Kozak sequences. While no additional ATG codons are found between the VP1 start codon and the start of VP3, an examination of the VP3 capsid revealed that nine additional ATG codons are present (amino acid positions 211, 235, 371, 402, 434, 523, 558, 604, and 634). Of these methionines, only those at amino acid position 211, 235, 523, 558, and 604 are in a context that is predicted favorable by Kozak. Since the VP3a fragment is slightly smaller than wildtype VP3, the contribution of continued read through translational initiation to the appearance of the VP3a fragment was examined by mutating the next two available ATG codons (M211 and M235) on a pIM45-M203L template yielding the plasmids, pIM45-M203L, pIM45-M203,211L and pIM45-M203,211, 235L (FIG. 2A). Western blotting analysis of capsid protein expression in whole cell lysates 48 hours post transfection of 293 cells in the presence of Ad5 (MOI=10) revealed that translational initiation could occur at both these ATG codons. FIG. 1B (lane 2) again demonstrates the formation of VP3a following the mutation M203L. Combined mutation of M203 and M211 allowed less robust expression of a second still shorter VP3-like fragment (VP3b, FIG. 1B, lane 3). Subsequent mutation of M235 in the pIM45-M203,211L background led to disappearance of this VP3b fragment generating pIM45-VP1,2 (FIG. 1B, lane 4). Collectively, while missense mutagenesis of the VP1 start codon does not alter the sequence of the VP2 and VP3 protein expressed (pIM45-VP2,3, M1L), mutation of the VP2 start codon results in one point mutation in the expressed VP1 protein (pIM45-VP1,3, T138A), and elimination of all VP3-like proteins results in three mutations in the remaining VP1 and VP2 proteins (pIM45-VP1,2, M203,211,235L).

An alternative method has been reported for eliminating VP3 expression that limits mutation of remaining capsid sequences to one point mutation in the VP2 start codon. Changing the VP2 start codon from ACG to ATG results in loss of VP3 expression (pIM45-VP1,2A) with one point mutation in both the VP1 and VP2 proteins (T138M). Presumably, this stronger VP2 start codon prevents efficient translational initiation at the downstream VP3 start codon. The VP2 start codon was mutated to ATG on a pIM45 template (pIM45-VP1,2A (FIG. 1C)) as an alternative means of eliminating VP3 protein (while maximizing VP2 expression). As expected, Western blotting analysis of capsid protein expression in whole cell lysates 48 hr post transfection of 293 cells in the presence of Ad5 (MOI=10) with pIM45-VP1,2A showed normal levels of VP1 protein produced, with significantly increased expression of VP2 protein (FIG. 1C, lane 2).

5.1.2 Construction of rAAV2 Capsid Plasmid Mutants that Express a Single Capsid Protein To complete the complementary pIM45 capsid groups, pIM45 plasmids that express a single capsid protein were generated next. Employing the same missense mutations described above on templates that now only express two capsid proteins, the plasmids, pIM45-VP1, pIM45-VP2, pIM45-VP2A, and pIM45-VP3 (FIG. 2) were also generated. pIM45-VP1, has the VP2 start codon mutated to alanine and M203, M211, and M235 mutated to L in the expressed VP1 protein. pIM45-VP2 has the VP1 start codon mutated to leucine and M203, M211, and M235 mutated to L. The expressed VP2 protein contains only M203, M211, and M235 mutations. pIM45-VP3 has the VP1 start codon mutated to leucine and the VP2 start codon mutated to alanine. Like all VP3 protein in these complementary groups, the VP3 coding sequence is not mutated. Finally, pIM45-VP2A has the VP1 start codon mutated to leucine and the VP2 start codon mutated to methionine resulting in the single T138M modification of the VP2 protein being expressed. Western blotting analysis of capsid protein expression in whole cell lysates 48 hr post transfection of 293 cells with pIM45-VP1, pIM45-VP2, pIM45-VP2A, and pIM45-VP3 in the presence of Ad5 (MOI=10) demonstrated that a single capsid protein could be expressed from the pIM45 cap ORF (FIG. 2) and completed the catalogue of plasmids required of a system for further genetic manipulation of a specific capsid protein across its entire coding sequence.

5.1.3 The Vp3 N-Terminal M203 and M211 are Critical for AAV Particle Formation

As control experiments for the production of AAV particles from the complementary groups of single and double capsid expressing pIM45 plasmids, particle production was examined from the individual plasmids described. Since VP3 protein makes up the bulk of the particle, and mutagenesis studies have indicated that the N-terminal region of VP3 is important for AAV particle formation, the effects of the three mutations required to eliminate VP3 expression (M203,211,235L) were investigated on the recovery of rAAV particles following standard production and purification protocols. The plasmids pIM45-M203L, pIM45-M211L, pIM45-M235L, and pIM45M-203,211,235L were cotransfected separately with pTR-UF5 and pXX6 in a 1:1:8 molar ratio in 293 cells and 72 hrs later the cells were harvested and particles were purified as previously reported. Western blotting of capsid protein expression and dot blot analysis of genome containing particles was carried out on the mutant virus preparations (FIG. 3A). No particles were recovered from pIM45-M203L (lane 2) indicating that the combination of VP1, VP2, and VP3a does not able form a stable AAV particle. Equally important in the formation of the particle is M211 (lane 3), as this mutation also prevented particle recovery. Whether it is the M211L in VP1, VP2, or VP3 that leads to this defective phenotype is unclear. This issue is addressed infra when pIM45-VP1,2 is complemented with pIM45-VP3 to produce AAV particles (FIG. 4 #5). Finally, particles were obtained from pIM45-M235L (FIG. 3A, lane 4) that package DNA efficiently.

5.1.4 AAV-Like Particles can be Produced that Lack VP1 or VP2 Protein

While the effect of mutating the individual capsid start codons on the formation of infectious AAV particles has been reported, given the improvements in AAV2 production and purification methods, control experiments were performed to reexamine the role of each capsid protein in the formation of the AAV2 particle capable of binding heparin. First examined were the effects of the elimination of one capsid protein on AAV2 particle recovery. pIM45-VP2,3, pIM45-VP1,3, pIM45-VP1,2, and pIM45-VP1,2A were transfected separately into 293 cells with pTR-UF5 and pXX6 in a 1:1:8 molar ratio and 72 hrs later the cells were harvested and particles were purified as previously reported. Western blotting, A20 ELISA, and dot blot analysis of these virus preparations were carried out (FIG. 3B) and, in agreement with previous reports, the elimination of the VP1 protein (pIM45-VP2,3) resulted in the production of an AAV-like particle that packaged genomes efficiently (lane 4). Surprisingly, in contrast with the initial report mapping the capsid start codons, transfection of the pIM45-VP1,3 plasmid resulted in the purification of an AAV-like particle capable of packaging genomes efficiently composed of only VP1 and VP3 (lane 3) that had only a modest decrease in infectivity compared to particles containing all three capsid proteins (two-fold decrease). Finally, regardless if VP2 is overexpressed, particles composed of only VP1 and VP2 were not recovered (lane 2).

5.1.5 AAV-Like Particles can be Produced Composed Only of VP3 Capsid Proteins

Figures 1, 3C:
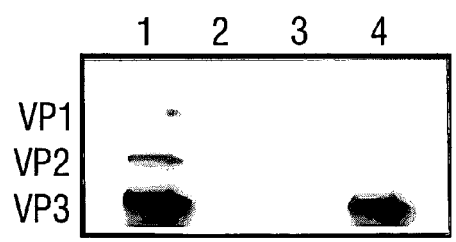
Figures 2, 3C:
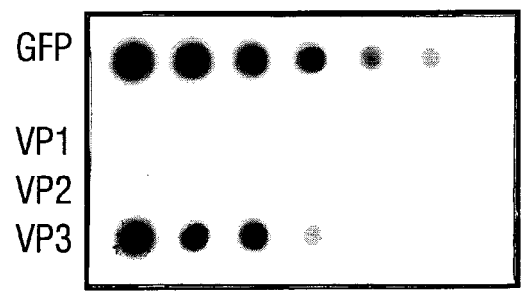

As with the pIM45 plasmids that express two capsid proteins, the ability of a single capsid protein to form an AAV-like particle was tested. pIM45-VP1, pIM45-VP2, pIM45-VP2A, and pIM45-VP3 were transfected separately into 293 cells with pTR-UF5 and pXX6 in a 1:1:8 molar ratio and harvested cells 72 hrs later and purified particles as previously described. Western blotting of capsid proteins, A20 ELISA, and dot blot analysis of virus preparations were carried out with no detectable AAV-like particles obtained from pIM45-VP1, pIM45-VP2, or pIM45-VP2A (FIG. 3C, lanes 2 and 3). Interestingly, like a recent insertional mutagenesis study of the cap ORF, an AAV-like particle composed exclusively of VP3 protein was purified (lane 3). Like the VP2,3 AAV-like particle, this particle had a significantly lower infectious phenotype.

5.1.6 rAAV Particles with all Three Capsid Proteins can be Produced from Capsid Complementation Groups Given the results of the control experiments, the ability to recover rAAV2 particles containing all three capsid proteins following transfection of two complementary pIM45 plasmids was tested (FIG. 4). To control for twice the Rep expression resulting from two pIM45 plasmids, an additional plasmid was constructed, pIM45-VP0, that expresses no capsid proteins as a result of 5 point mutations (M1L, T138A, M203, 211,235L). Complementary group VP0 (FIG. 4, #1) includes pIM45 and pIM45-VP0, group VP1 includes pIM45-VP1 and pIM45-VP2,3 (FIG. 4, #2), group VP2 includes pIM45-VP2 and pIM45-VP1,3 (FIG. 4, #3), group VP2A includes pIM45-VP2A and pIM45-VP1,3 (FIG. 4, #4), and group VP3 includes pIM45-VP3 and pIM45-VP1,2 (FIG. 4, #5). Western blotting of capsid proteins, A20 ELISA, and dot blot analysis of virus preparations were carried out following transfection of the individual groups into 293 cells with pTR-UF5 and pXX6 in a 1:1:8 molar ratio. 72 hrs post transfection the cells were harvested and particles were purified as previously described. Infectious rAAV particles containing all three capsid proteins with similar yields were recovered (FIG. 5A). Interestingly, the VP2A group resulted in the formation of particles with an apparent alteration of capsid protein stoichiometry and lower infectivity compared to other groups (lane 4). The characteristics of this group suggest that this preparation may contain a single unique particle that is defective per se or alternatively two particles may be assembled containing all three capsid proteins at normal levels and a defective interfering particle composed of VP2 and VP3 proteins with altered stoichiometry. Cotransfection of the pIM45-VP2A and pIM45-VP3 plasmid should yield a particle with an altered VP2:VP3 ratio if such a defective interfering particle contributes to the low titer of this group. Indeed, an AAV-like particle with an overrepresentation of VP2 protein was purified that resembled the VP2,3 and VP3 only particles with respect to infectivity (FIG. 5B, lane 4).

5.1.7 Production of AAV Particles with Insertions in the VP1/VP2 Overlap Region

Since the VP1/VP2 overlap region has been shown to be on the surface of the particle and flexible in the acceptance of targeting epitopes, the ability of this region to accept larger insertions was examined. Presumably, large insertions in the VP3 protein would decrease ones success in obtaining a particle due to steric hindrances in assembling the 60 modified capsid subunits. Sixty ligands were considered excessive when inserting large molecules into the AAV particle, so the strategy employed was to focus larger insertions to VP1 and/or VP2 proteins. Large insertions in both VP1 and VP2 protein immediately after amino acid 138 may have less steric constraints but may produce particles with defective trafficking due to the juxtaposition of a large insertion to the putative phospholipase motif in VP1 protein. Also, since VP1, essentially an N-terminal fusion of 137 amino acids to VP2, and a CD 34 sc antibody VP2 protein fusion are readily incorporated into an AAV particle, insertion of large epitopes only at the N-terminus of VP2 may have advantages. Notably, genetic modification of the VP2 protein exclusively has not been accomplished from within a pIM45 based AAV production scheme. To address the ability to insert large peptide sequences in the VP1/VP2 overlap region of the cap ORF, directional cloning sites were generated immediately after amino acid 138 in plasmids that express VP1 and VP2 or VP2 only (FIG. 6A). The choice of EagI/MluI restriction sites resulted in two amino acids insertions on either side of further inserted sequence (RP/RT). pIM45-VP1,2A and pIM45-VP2A were chosen as templates for engineering EagI/MluI restriction sites immediately after amino acid 138 in VP1 and VP2 or in VP2 only (pIM45VP1,2AEM138, pIM45-VP2AEM138, FIG. 6A). Templates with VP2 protein over expression were used to help ensure that genetically-modified VP2 would be present at sufficient levels for assembly. The pIM45-VP1,2AEM138 plasmid was complemented with pIM45-VP3, while the pIM45-VP2AEM138 plasmid was complemented with pIM45-VP1,3 for the production of rAAV particles carrying insertion sequences. Insertion of the coding sequence for leptin and GFP was in these plasmids generated pIM45-VP1,2Alep, pIM45-VP2Alep, pIM45-VP1,2AGFP, and pIM45-VP2AGFP. These plasmids and their complements were transfected with in 293 cells in the presence of pTR-UF5 (leptin-insertions) or pTR-dsRFP (GFP) and pXX6 in a 1:1:8 molar ratio. 72 hrs post transfection the cells were harvested and virus particles were purified as previously described. Western blotting, A20 ELISA, and dot blot analysis were carried out on the virus preparations (FIG. 6B and FIG. 6C). For the leptin-inserted virus preparations successful insertion in both VP1 and VP2 or VP2 only was possible in the purified particle, but GFP-insertion in the purified particle was only possible in the VP1 protein (VP2-GFP was excluded in both cases).

5.1.8 Discussion

This example increases the flexibility in probing the surface of the particle by isolating the expression of a given capsid protein to a separate plasmid. Such an approach allows for manipulation of this capsid protein only within the produced particle and allows for retesting regions of capsid overlap for the acceptance of sequence modification. Alternatively, the system also allows for the modification of only two of the capsid proteins while leaving the third protein unmodified. Using the missense mutation of capsid start codons to generate all required plasmids, characterization of the catalogue of plasmids required for this system yielded interesting results concerning the role of each capsid protein in the assembly of AAV-like particles.

Elimination of VP3-like fragments illustrates importance of VP3 N terminus, as particles with these mutations in the VP1 and VP2 proteins were recovered following complementation of pIM45-VP1,2 with pIM45-VP3. Evidence that ability to modify individual capsid proteins in regions of overlap may allow production of particles that were defective for production when mutations are in all three proteins. Increases the flexibility in manipulation of the particle for targeting purposes. Recently, isolation of the expression of a C-terminal modified VP3 separately allowed for modification of the c-terminus of VP3 with his tag and production of viable recombinant virus follow nickel chromatography. Like the study involving the VP3-6×His tag where the modified capsid protein was isolated and VP1 and VP2 did not carry the insertion, lethal mutations in the overlapping N-terminus region of VP3 (M203,211) resulted in particles from complementation group 3 when these mutations were only in VP1 and VP2 with normal VP3.

The present system allows for complementation and recovery of rAAV2 particles with all capsid proteins present. Since it allows for the genetic modification of only one or two of the capsid proteins, it can also be used for studies of previously reported lethal mutations in overlapping capsid sequences to see if mutations at the same positions in fewer capsid proteins rescue the position for particle manipulation. Important genetic modification would include insertion of genetic sequence for retargeting the virus, purification of the virus, monitoring of the virus particle following infection, or presentation of immunogenic epitopes on the surface of the virus particle.

Insertions of large peptides (leptin and GFP) into the overlapping region of VP1 and VP2 resulted in the purification of virus like particles carrying these insertions. This required preliminary isolation of the expression of VP1 and VP2 (pIM45-VP1,2A) or VP2 only (pIM45-VP2A) to a separate plasmid followed by insertion of peptide sequences after amino acid 138 allowed for the production of peptide inserted AAV-like particles following complementation with pIM45-VP3 or pIM45-VP1,3. This example is the first report of the purification of an AAV-like particle containing a mutation in the VP2 protein exclusively. Estimated similar stoichiometry of capsid proteins in particle. Retain ability to package genomes, bind A20, and are infectious as they retain native tropism due to intact heparin binding motif. VP2 overexpression may have ensured the inclusion of modified VP2 protein large insertions with VP2 acg start codon produced significantly less modified VP2 proteins.

5.2 Example 2

Heparin Sulfate Binding Motif in AAV2 Capsid Proteins Required for Native Tropism In this example, charged-to-alanine substitution mutants were made to analyze the effects of single and combinatorial mutations in the capsid gene. New point mutants that result in assembly, packaging, and receptor binding deficiencies have been discovered. Importantly, five amino acids, arginines 484, 487, 585, and 588, and one lysine at position 532 have been identified that appear to mediate the natural affinity of AAV for HSPG. Those observations contribute to the current map of the AAV capsid and provide a reagent for the discovery of novel, heparin independent targeting ligands.

5.2.1 Materials and Methods 5.2.1.1 Plasmids

Plasmid pIM45 (previously called pIM29-45) contains the Rep and Cap coding sequences from AAV with expression controlled by their natural promoters (McCarty et al., 1991). It was used as the parent template for construction of all the AAV2 mutant vectors.

Plasmid pXX6 supplies the adenovirus helper gene products in trans to allow rAAV production in an adenovirus free environment (Xiao et al., 1998).

Plasmid pTR2-UF5 supplies the recombinant AAV DNA to be packaged. It contains a cytomegalovirus promoter driving expression of a green fluorescent protein (GFP) reporter gene flanked by AAV2 terminal repeats (Klein et al., 1998). Plasmid pTR5-UF11 was constructed using an expression cassette consisting of a strong constitutive CBA promoter (Xu et al., 2001), GFP reporter gene (Zolotukhin et al., 1996), woodchuck hepatitis virus posttranscriptional regulatory element WPRE (Donello et al., 1998) and bovine growth hormone gene polyadenylation signal. The cassette was assembled using standard molecular biology techniques and substituted for the lacZ cassette in the plasmid backbone pAAV5RnlacZ containing AAV5 terminal repeats (Chiorini et al., 1999).

Plasmids pXYZ1, pXYZ5 contain the AAV1 and AAV5 Cap coding sequences, respectively, in addition to AAV2 Rep coding sequence with an ACG start codon under control of the AAV2 p5 promoter (Zolotukhin et al., 2002). Plasmid pAAV5-2 contains the AAV5 nucleotides 260 to 4448 without terminal repeats (Chiorini et al., 1999).

5.2.1.2 Construction of Mutant Capsid Plasmids

Quickchange site directed mutagenesis (Stratagene) was performed on plasmid pIM45 as per the manufacturer's instructions. For each AAV2 mutant, two complementary PCR primers that contained alanine or lysine substitutions in addition to a silent change for restriction endonuclease screening purposes were used to introduce changes into pIM45. For construction of AAV5-HS, pAAV5-2 was used as the parental template. Sequences for the oligonucleotides used are available upon request. PCR products were digested with DpnI to remove methylated template DNA, phenol:cholorform:isoamyl (25:24:1) extracted, ethanol precipitated, and transformed into electrocompetent JM109 cells. Miniprep DNA was extracted from overnight LB/amp cultures and screened with the appropriate restriction enzyme. All mutants were sequenced prior to use. Transfection quality plasmid DNA was produced by standard alkaline lysis method of a 1-liter TB culture followed by PEG precipitation and cesium chloride gradient purification.

5.2.1.3 Cell Culture

Human embryonic kidney 293's and cervical carcinoma HeLa C12's, a gift from Dr. Phil Johnson (Clark et al., 1996) were grown in Dulbecco Modified Eagle Medium (Gibco-BRL) supplemented with 100 U/ml penicillin, 100 U/ml streptomycin, 10% bovine calf serum, sodium pyruvate and L-glutamine. Cells were incubated at 37° C. in a 5% $CO_2$ atmosphere.

5.2.1.4 Production Of rAAV2 Particles

To produce AAV2 virions, low passage 293's were seeded so that they were approximately 75% confluent at transfection time. A triple plasmid transfection protocol (Xiao et al., 1998) was followed that included pIM45 to supply Rep and mutated capsid genes, pTR2-UF5 (Klein et al., 1998) to supply recombinant DNA with AAV2 terminal repeats and a CMV driven GFP reporter gene, and pXX6 (Xiao et al., 1998) to supply the adenovirus helper functions in trans. A total of 60 mg of plasmid DNA in a 1:1:1 molar ratio was transfected by lipofectamine (Invitrogen).

To produce pseudotyped rAAV 1 and rAAV5 particles, a total of 60 µg of pXYZ1 or pXYZ5 (Zolotukhin et al., 2002) was co-transfected with pTR2-UF5 plasmid DNA in a 1:1 molar ratio as above. To produce rAAV5 and rAAV5-HS virions a total of 60 µg of pAAV5 or pAAV5-HS was co-transfected with pTR5-UF11.

Purification of rAAV has been described previously (Zolotukhin et al., 1999; Zolotukhin et al., 2002). Briefly, 72 hr after transfection, cells were harvested and the pellets were resuspended in lysis buffer (0.15M NaCl, 50 mM Tris-Cl pH=8.5). Virus was released by three cycles of freezing and thawing. Benzonase (Sigma) was added to the cell lysate to a final concentration of 140 U/ml and incubated at 37° C. for 30 min. Cell debris was pelleted by centrifugation at 3,700×g for 30 min and the supernatant was loaded onto a 15%-25%-40%-60% iodixanol (5,5' [2-hydroxy-1,3-propanediyl)bis (acetyl-amino)]bis[N,N'-bis(2,3-dihydroxypropyl-2,4,6-tri-iodo-1,3-benzenecarboxamide] step gradient (Nycomed). The 40% fraction was collected after centrifugation at 69,000×g for 1 hr and stored at −80° C. until further use.

5.2.1.5 Virus Titer Determination

To determine the concentration of intact capsid particles, the A20 ELIZA (American Research Bioproducts) was used. The A20 antibody detects intact, fully assembled particles, both full and empty (Wistuba et al., 1995). Iodixinal purified stocks were serially diluted and processed by the manufacturer's recommended protocol. Only readings within the linear range of the kit standard were used.

To determine the concentration of DNA-containing particles, real-time (RT)-PCR™ was performed using a Perkin Elmer-Applied Biosystems (Foster City, Calif.) Prism 7700 sequence detector system. Equal volumes of iodixinal purified virus stocks were treated with 600 U/ml benzonase in 50 mM Tris-CL pH-7.5, 10 mM $MgCl_2$, 10 mM $CaCl_2$ at 37° C. for 30 min. 280 U/ml proteinase-K was added to reactions adjusted to 10 mM EDTA and 5% SDS, and then incubated at 37° C. for 30 min. Reactions were extracted with phenol\chloroform/isoamyl-alcohol (25:24:1) and undigested DNA was precipitated overnight with ethanol and glycogen carrier. Precipitated DNA pellets were resuspended in 100 µl of water. Five µl was used for RT-PCR™ analysis in a reaction mixture that included 900 nM each of GFP forward (5'-

TTCAAAGATGACGGGAACTACAA-3') (SEQ ID NO:4) and reverse (5'-TCAATGCCCTTCAGCTCGAT-3') (SEQ ID NO:5) primers, 250 nM Taqman probe (5'-6FAM-CCCGCGCTGAAGTCAAGTTCGAAG-TAMRA-3') (SEQ ID NO:6), 1× Taqman universal PCR master mix in a total volume of 50 µl. Cycling parameters were 1 cycle each of 50° C., 5 mins, and 95° C., 10 mins, followed by 40 cycles of 95° C., 15 sec and 60° C., 1 min. Only values within the linear portion of a standard curve having a coefficient of linearity greater than 0.98 were accepted. The average RT-PCR™ titer was calculated from virus preparations assayed three times.

To determine the infectious titer of the wt and mutant virus stocks, a green cell assay (GCA) was performed essentially as previously described (Zolotukhin et al., 1999). Briefly, HeLa C12 cells were seeded in a 96 well plate so that they were approximately 75% confluent at infection time. Cells were infected with 10-fold serial dilutions of iodixanol purified mutant viruses and Ad5 at a constant multiplicity of infection (MOI)=10. Cells were incubated at 37° C. in a 5% $CO_2$ atmosphere for 24 hrs and examined by fluorescence microscopy. The average GCA titer was calculated by averaging the number of green cells counted in individual wells from two or three virus preparations assayed three times. Particle to infectivity ratios were calculated by dividing the average RT-PCR™ titer by the average GCA titer. In some figures, this number was expressed as a $log_{10}$ value with rAAV2 arbitrarily set to one.

5.2.1.6 In Vitro Heparin Binding Assay

Bio-Rad microspin columns were treated with silicon dioxide to minimize non-specific binding of the virus to the column wall. A 500 pp heparin-agarose (Sigma H-6508) gravity column was prepared by washing with 3 column volumes each of 1×TD (137 nM NaCl, 15 mM KCl, 10 mM $Na_2PO_4$, 5 mM $MgCl_2$, 2 mM $KH_2PO_4$, pH=7.4), 1×TD+2M NaCl and 1×TD. Approximately equal numbers of virus particles were added to 1×TD to a final volume of 600 µl and loaded onto the column. The column was washed with 7 column volumes of 1×TD. Bound virus was eluted with 1×TD+2M NaCl. The entire volume of the flow through, wash, and eluate fractions were pooled separately, denatured by boiling in SDS, and slot blotted onto nitrocellulose for immunoblot analysis. The membrane (Osmonics) was blocked in PBS/0.05% Tween-20+5% dry milk, and incubated with B1 antibody (Wistuba et al., 1997) at a 1:3000 dilution for 18 hrs at 4° C. Anti-mouse IgG-horse radish peroxidase was used to detect bands by enhanced chemiluminesence (Amersham-Pharmacia).

5.2.1.7 Fluorescence Activated Cell Sorting (FACS)

HeLa C12 cells were seeded in 6 well plates so that they were approximately 75% confluent at infection time. Cells were infected with an rAAV MOI=500 based on the genomic titer as determined by DNA dot blot assay (Zolotukhin et al., 1999). Adenovirus type-5 was used at an MOI-10 plaque forming units (pfu). Twenty-four hours postinfection, cells were washed, trypsinized, and fixed in 2% paraformaldyhede. FACS analysis for GFP expression was done in the ICBR Flow Cytometry lab of the University of Florida on a Becton-Dickinson FACS can.

5.2.1.8 Cell Attachment Assay $10^6$ Hela C12 cells were infected with rAAV2 at a genome containing particle MOI=100 or R585A/R588A at an MOI=1000 as determined by RT-PCR™. Cells were incubated at 37° C. in a 5% $CO_2$ atmosphere until harvesting. At indicated time points, the infection media was removed and saved and the cells were washed four times with PBS before being scraped. Low molecular weight DNA from the infection media and the cell pellet was extracted by the Hirt procedure (Hirt, 1967). DNA pellets were resuspended in 0.2M NaOH, incubated at 37° C. for 20 mins, and slot blotted onto nitrocellulose. DNA was UV cross-linked to the nitrocellulose and probed at 65° C. for 18 hrs with [$\alpha$-$^{32}$P]-dATP labeled GFP probe in hybridization buffer (7% SDS, 10 mM EDTA and 0.5M $Na_2HPO_4$). Membranes were washed twice in 2×SSC/0.1% SDS, 0.2×SSC/0.1% SDS, 0.1×SSC/0.1% SDS, and rinsed with water. The membranes were then exposed to film and quantitated using a BAS-1000 phosphor imager (Fuji).

5.2.2 Results 5.2.2.1 Selection and Generation of AAV Mutants

A considerable body of information regarding the determinants of HS-protein interactions suggests that their association is driven mainly by electrostatic attraction between acidic sulfate groups on the polysaccharide and basic R-groups on amino acids in the target protein (Hermens et al., 1999; Hileman et al., 1998). It was hypothesized that similar electrostatic interactions would govern HSPG-AAV2 association. In order to evaluate the role of particular amino acids in receptor binding, a panel of mutants was generated by site directed mutagenesis of selected residues. The selection was confined primarily to basic amino acids (His, Lys, Arg) in VP3 as AAV-like particles composed only of VP3 proteins have been purified by heparin affinity chromatography. Any basic amino acid substitution mutant that previously had demonstrated capsid instability or efficient purification by heparin affinity chromatography (Wu et al., 2000) was excluded from the pool of mutants.

Seven AAV serotypes have been reported (Bantel Schaal and zur Hausen, 1984; Gao et al., 2002; Hoggan et al., 1996; Parks et al., 1967; Rutledge et al., 1998). Several groups have shown that rAAV2 and rAAV3 bind efficiently to heparin sulfate (Rabinowitz et al., 2002; Shi et al., 2001; Wu et al., 2000). A single report concerning rAAV1 suggests that it binds with low affinity, if at all, to heparin (Rabinowitz et al., 2002). In contrast, rAAV4 and rAAV5 do not bind heparin and instead recognize 2,3, O-linked and 2,6 N-linked sialic acid moieties (Kaludov et al., 2001). Indeed, this may account for their different cellular tropisms. It was reasoned that residues conserved among all five serotypes were probably not participating directly in receptor discrimination and binding and were excluded from further consideration. Additionally, a number of charge to alanine substitution mutants in the AAV capsid had been identified, and these had been characterized for their ability to bind heparin sulfate columns (Wu et al., 2000) and amino acid positions that did not affect heparin binding or had been shown to be assembly mutants were excluded from further study. Using a Clustal W algorithm, a sequence alignment of capsid proteins from serotypes 1-5 was generated, and 9 basic residues in AAV2 that were conserved in AAV3 and/or AAV 1 but were uncharged or acidic in AAV4 and AAV5 were identified that had not previously been tested for heparin-agarose binding (Table 4). In addition to these 9 amino acids, Wu et al. (2000) described a virus deficient for heparin binding with alanine substitution mutations at positions 585, 587, and 588. Finally, during the course of these studies, the atomic structure of AAV2 was solved (Xie et al., 2002) and suggested that residues 484, 513, and 532 might participate in a heparin-binding pocket as they were located close to residues 585, 587, and 588. These six extra residues were also included to complete the mutant panel (Table 4).

TABLE 4

RESIDUES CHOSEN FOR MUTAGENESIS

| VP Residue[a] | AAV Serotype[b] | | | | |
|---|---|---|---|---|---|
| | 2 | 3 | 1 | 4 | 5 |
| 358 | H | H | H | Q | T |
| 447 | R | R | R | S | S |
| 459 | R | R | D | T | G |
| 484 | R | R | R | K | R |
| 487 | R | R | R | G | G |
| 509 | H | H | H | T | E |
| 513 | R | R | R | R | A |
| 526 | H | H | H | A | N |
| 527 | K | K | K | G | N |
| 532 | K | K | K | K | N |
| 544 | K | K | K | P | S |
| 566 | R | R | K | A | Q |
| 585 | R | S | S | S | S |
| 587 | N | N | S | S | T |
| 588 | R | T | T | N | T |

[a]Residues selected for mutagenesis were generated by a sequence alignment of the VP1 capsid protein from each serotype using the Clustal W algorithm (Vector NTi 5.2, Informax).
[b]Amino acids are represented by their one letter abbreviation. Blue letters represent positively charged, basic amino acids. Red letters represent any other amino acid.

5.2.2.2 Mutant Virus Production and Physical Characterization

A series of single and combinatorial capsid mutants were generated from the pool of candidate residues in the AAV2 capsid gene (Table 4). To designate the mutant viruses, the number of the mutated amino acid based on its position in VP1 was used. Iodixanol purified virus stocks were checked by western blot using the monoclonal antibody B1. The B1 antibody recognizes a linear epitope in the extreme carboxyl terminus of all three VP proteins from AAV serotypes 1, 2, 3 and 5 (Rabinowitz et al., 2002; Wobus et al., 2000). With the exception of H358A, capsid proteins were detected in all virus stocks (FIG. 7). To confirm that assembled capsids, rather than subunits or assembly intermediates, had been purified, the particle concentration was measured with an A20 antibody ELISA (Table 5). The A20 antibody recognizes a structural epitope that is found only on assembled capsids with or without packaged DNA (Grimm et al., 1998). Although there was some variability between stocks due to different transfection efficiencies and purification recoveries, only the H358A mutant was negative by A20 ELISA assay. Excluding H358A, a particle concentration range was determined that spanned 1.5 logs and correlated reasonably well with the B1 antibody results (FIG. 7; Table 5). Several possibilities may account for this range of particle titers, including that capsid subunits containing these mutations (i) form intact particles inefficiently, (ii) are unstable during purification or (iii) formed a particle with a partially disrupted A20 epitope. Since none of these mutations fell within the antigenic regions that have been mapped for A20 (Wobus et al., 2000), these results suggested that the A20 epitope had probably not been modified but rather the stability or assembly of some of the mutants was altered so that fewer particles were recovered after iodixanol centrifugation (FIG. 7; Table 5).

TABLE 5

TITERS AND HEPARIN BINDING PROPERTIES OF MUTANTS

| Mutant virus[a] | Particle titer[b] | | Infectious titer[c] | Particle to | Heparin | Empty/ |
|---|---|---|---|---|---|---|
| | A20/ml | Genome/ml | (IU/ml) | infectivity[d] | binding[e] | Full[g] |
| rAAV2 (WT) | $1.5 \times 10^{12}$ | $4.6 \times 10^{11}$ | $1.8 \times 10^{10}$ | 25 | + | 3.4 |
| H3558A | $<1.0 \times 10^{8}$ | $<1.0 \times 10^{6}$ | $<1.0 \times 10^{4}$ | N/D[f] | N/D | N/D |
| R447A | $1.2 \times 10^{12}$ | $3.4 \times 10^{10}$ | $1.3 \times 10^{9}$ | 25 | + | 35.9 |
| R459A | $9.1 \times 10^{10}$ | $7.2 \times 10^{8}$ | $<1.0 \times 10^{4}$ | >72500 | + | 126.3 |
| R484A | $1.5 \times 10^{11}$ | $3.0 \times 10^{10}$ | $<1.0 \times 10^{4}$ | >2976667 | +/− | 5.1 |
| R487A | $5.4 \times 10^{11}$ | $2.2 \times 10^{11}$ | $2.3 \times 10^{8}$ | 954 | +/− | 2.5 |
| H509A | $4.6 \times 10^{10}$ | $2.3 \times 10^{9}$ | $6.9 \times 10^{5}$ | 3285 | + | 20.3 |
| R513A | $2.9 \times 10^{11}$ | $1.7 \times 10^{10}$ | $1.6 \times 10^{8}$ | 106 | + | 17.9 |
| K532A | $1.1 \times 10^{11}$ | $3.6 \times 10^{10}$ | $<1.0 \times 10^{4}$ | >3633333 | +/− | 3.0 |
| K544A | $2.0 \times 10^{11}$ | $1.7 \times 10^{10}$ | $8.3 \times 10^{8}$ | 20 | + | 11.9 |
| R566A | $5.1 \times 10^{11}$ | $1.6 \times 10^{10}$ | $7.4 \times 10^{8}$ | 21 | + | 32.6 |
| R585A | $5.0 \times 10^{11}$ | $4.8 \times 10^{10}$ | $1.7 \times 10^{7}$ | 2812 | − | 1.4 |
| R587A | $4.4 \times 10^{11}$ | $1.3 \times 10^{10}$ | $1.7 \times 10^{7}$ | 165 | + | 34.7 |
| R588A | $2.4 \times 10^{11}$ | $5.6 \times 10^{10}$ | $3.0 \times 10^{6}$ | 18521 | − | 4.2 |
| H526A, K527A | $1.4 \times 10^{11}$ | $8.2 \times 10^{10}$ | $5.5 \times 10^{7}$ | 1489 | + | 1.8 |
| R585A, R588A | $1.2 \times 10^{12}$ | $9.2 \times 10^{11}$ | $1.9 \times 10^{7}$ | 48421 | − | 1.2 |
| R585K | $1.3 \times 10^{12}$ | $3.7 \times 10^{10}$ | $4.0 \times 10^{8}$ | 92 | + | 35.4 |
| R585K, R588K | $1.4 \times 10^{12}$ | $3.9 \times 10^{10}$ | $8.9 \times 10^{7}$ | 436 | + | 34.9 |
| AAV1 | N/D | $3.7 \times 10^{10}$ | $1.1 \times 10^{9}$ | 37 | +/− | N/D |
| AAV5 | N/D | $3.4 \times 10^{10}$ | $3.2 \times 10^{6}$ | 10692 | − | N/D |
| AAV5-HS | N/D | $8.0 \times 10^{8}$ | $<1.0 \times 10^{4}$ | >80000 | + | N/D |

[a]Two letters flanking a number designate each mutant. The first letter is the one letter abbreviation for the wild type amino acid followed by its numerical position in VP1 followed by the one letter abbreviation for the amino acid to which it was mutated.
[b]A20 particle titers were determined as described using the A20 ELISA assay. Genomic titers were determined by RT-PCR ™.
[c]Infectious titers were determined by green cell assay as described by counting GFP fluorescent cells.
[d]Particle-to-infectivity ratio was calculated by dividing the average genomic titer as determined by RT-PCR ™ by the average green cell assay titer.
[e]Determined by heparin-agarose binding assay. +, >95% virus recovered in the eluate; +/−, >50 recovered in the eluate; −, <5% of virus recovered in the eluate.
[f]N/D not determined.
[g]Empty-to-full ratio was determined by dividing the A20 particle titer by the average genomic titer.

To determine whether any mutations affected DNA packaging, the titer of DNA containing virions was determined by real-time (RT) PCR™ (Clark et al., 1999; Veldwijk et al., 2002) (Table 5) and confirmed by DNA dot blot hybridization. Although there was variation between preparations, the majority of the capsid mutants were able to package detectable DNA (Table 5). As expected, H358A was negative for DNA packaging, as it did not produce virus particles. It was concluded that none of the capsids in the mutant panel that made A20 positive particles were completely defective for DNA packaging. However, by comparing the A20 ELISA and PCR titers, it was noted that stocks of mutant R459A contained 40-fold more empty particles than wild type rAAV2. Thus, R459 could have a role in DNA packaging. Although less dramatic, mutants R447A, R566A, R587A, R585K, and R585K/R588K had approximately 10-fold more empty particles than rAAV2. The remainder of the virus preparations packaged DNA at levels comparable to wild type AAV2 (Table 5).

5.2.2.3 In Vitro Heparin Binding of Capsid Mutants

To assess the ability of mutant capsids to bind heparin sulfate, a modification of an assay previously described by Wu et al. (2002) was used. Virus preparations that had been purified by iodixanol step gradients were loaded on heparin agarose columns and the entire volume of the flow through, wash, and eluate fractions were pooled separately, denatured, and slot blotted onto nitrocellulose for immunoblot analysis with B1 antibody. A representative Western analysis for each mutant is shown in FIG. 8. As expected, wild type AAV2 was not observed in the flow through or wash fractions and most of the virus bound to the column was recovered at the elution step. Eight other mutants, R447A, R459A, H509A, R513A, K544A, K566A, N587A, and H526A/K527A, had a heparin-agarose binding phenotype indistinguishable from wild type. The results with R513A confirmed a previous report (Wu et al., 2000) in which a double mutant at positions 513 and 514 was positive for heparin binding. In marked contrast, it was observed that any capsid harboring a non-conservative mutation at position 585 or 588 was detected only in the flow through and wash. Intermediate heparin-agarose binding phenotypes in mutants R484A, R487A and K532A were also detected with approximately equal levels of signal detected in the flow through, wash, and eluate. The results with K532A were inconsistent with previous results in which a mutant containing alanine substitutions at positions 527 to 532 was found to be positive for heparin binding (Wu et al., 2000). These data suggested that at least five amino acids had the potential to contribute to the electrostatic attraction between AAV and heparin sulfate. These included predominantly R585 and R588, and to a lesser but detectable extent R484, R487, K532.

To confirm that the charge at R585 and R588 was primarily responsible for heparin interaction, two viruses were generated with conservative mutations, R585K and R585K/R588K, and tested them in the in vitro heparin binding assay. Both lysine and arginine residues are positively charged, however, lysine is slightly larger due to an additional methyl residue in the side group. Both of these capsids bound to heparin-agarose almost as well as wild type virus (FIG. 8). In each case, most of the virus was recovered in the eluate; however, the flow through and wash fractions also contained minor amounts of virus. This result suggested that both localized negative surface charge, and the relative position of the changes in this region of the capsid, are responsible for mediating the interaction with heparin-agarose.

Finally, as a control and to validate the heparin binding assay, the ability of wild type rAAV2, rAAV1, and rAAV5 to bind to heparin-agarose was compared. For this purpose, recombinant viruses were produced and purified by using a pseudotyping protocol developed to package AAV2 terminal repeat containing genomes into alternative serotype capsids (FIG. 9A) (Rabinowitz et al., 2002; Zolotukhin et al., 2002). Approximately equal amounts of input virus as determined by Western blot signal intensity were applied to a heparin-agarose column, and fractions from the column were slot blotted onto nitrocellulose for immunodetection using the B1 antibody (FIG. 9B). As expected, rAAV2 was efficiently retained by heparin-agarose under low ionic conditions but the majority of rAAV1 and all of rAAV5 was seen in the flow through and wash. A low amount of AAV1 was detected in the eluate. These data were consistent with previous reports (Rabinowitz et al., 2002).

5.2.2.4 Multiple Mutations in the AAV2 Capsid Effect Viral Transduction

To determine how the heparin-agarose binding phenotypes correlated to infectivity, iodixanol stocks were tested for their ability to transduce HeLa C12 cells by performing a green cell assay (GCA). Cells in a 96 well plate were co-infected with Ad5 at a constant MOI=10 pfu/cell and mutant AAV virus stocks in a 10-fold dilution series. Twenty-four hours post-infection (hpi), the number of GFP expressing cells in individual wells were counted and a GCA titer was calculated (Table 5). The detection limit of this assay was approximately $10^4$ transducing units/ml. The GCA titers were then normalized to genome containing physical particles by calculating a particle to infectivity (P/I) ratio. This ratio is equivalent to the number of genomes required to transduce one cell (Table 5). To get a measure of the relative impact of a particular mutation on viral infectivity, the P/I ratio of each mutant was divided by the wild type capsid P/I ratio and the $\log_{10}$ of this value was plotted in FIG. 10. This provided a simple comparison of how many genome-containing particles of each mutant were required to achieve the same number of transduced cells as the wild type virus.

Several phenotypes emerged from this analysis. Mutants R477A, K544A, and K566A were virtually identical to wild type, and mutants R513A, N587A, R585K, and R585K/R588K were only slightly defective (approximately 1 log). These seven mutants were found previously to bind heparin sulfate to the same extent as wild type rAAV2 (FIG. 8).

Three of the mutants R459A, R484A, and K532A produced virus that was essentially non-infectious with P/I ratio between $7.2 \times 10^4$ and $3.6 \times 10^6$ compared to the wild type ratio of 25 (Table 5, FIG. 10). The P/I ratios for these mutants were minimum estimates based on the GCA assay sensitivity of $1 \times 10^4$ IU/ml. In fact, no transduction events were seen with any of these mutants.

R459A was the most severe example of three mutants (R459A, H509A, and H526A/K527A) that were essentially wild type for heparin binding but defective for transduction (FIG. 10). These mutants were presumably defective in some late stage of viral infection.

Finally, all five of the mutants that were defective or partially defective for heparin binding (R484A, R487A, K532A, R585A, and R588A) were defective for transduction. However, the loss of infectivity did not correlate completely with the loss of heparin binding (compare FIG. 8 and FIG. 10). Two of these mutants (R484A and K532A) were only partially defective for heparin binding but severely defective (>5 logs) for transduction, suggesting that some other step in viral infection was defective in these mutants in addition to heparin binding. The remaining heparin binding mutants (R487A, R585A, and R588A) had defects in transduction that approximately correlated with their ability to bind heparin.

5.2.2.5 Evaluation of R585A/R588A Cell Attachment In Vivo

As mentioned earlier, alanine substitutions at either position 585 or 588 were the only mutations that completely abolished binding to HS (FIG. 8), suggesting that these two arginines were primarily responsible for heparin binding. Moreover, the extent to which mutation of either or both of these residues inhibited transduction (FIG. 10, 1.5-3 logs) was approximately the same when soluble heparin sulfate is used to inhibit wild type rAAV2 infection (Handa et al., 2000). Those mutants were, therefore, examined in more detail.

To see if the defect in transduction of R585 and R588 mutants could be overcome by using higher input MOI's, cells were co-infected with rAAV2 or the mutant viruses at an MOI=500 genome containing particles/cell. Twenty-four hours post-infection cells were examined by fluorescence microscopy and counted by FACS. The data from three independent experiments and representative histograms are shown in FIG. 11. As expected, the defects in transduction of the single mutants, R585A and R588A, could be overcome by higher MOI's (56% and 25% transduction for R585A, and R588A, respectively). Predictably, the level of recovery of the double mutant, R585A/R588A, was lower (10% transduction). However, it was clear that the fluorescence intensity profile for the heparin binding mutants was quite different from wild type, suggesting a significant delay in the onset of GFP expression by 24 hours. In contrast, the level of transduction of the conservative double mutant, R585K/R588K, and the heparin positive mutant, N587A, was indistinguishable from wild type.

As a more direct assay for cell attachment Hela C12 cells were transfected and the location of viral DNA tracked. Cells were infected with rAAV2 at an MOI=100 or R585A/R588A at an MOI=1000 genome containing particles as determined by RT-PCR™. At 1, 4, and 20 hpi, the infection media was removed and saved, and the cells were washed extensively to remove any residual unbound virus. The cells were then harvested and low molecular weight DNA was extracted from both the infection media (unbound) and the cell pellet (bound or internalized) by the Hirt procedure and transferred to nitrocellulose for Southern hybridization with an [$\alpha$-$^{32}$P]-dATP labeled GFP probe (FIG. 12A and FIG. 12B).

At all time points rAAV2 DNA was detectable both bound/internalized and in the infection media. In contrast, cells infected with 10-fold more genomic copies of R585A/R588A showed the vast majority of the signal only in the unbound fraction (FIG. 12A). Phosphor imager analysis determined that at each time point approximately one third of the total rAAV2 DNA was attached or internalized compared to only 1% of R585A/R588A (FIG. 12B). As these infections were performed at 37° C., the process of internalization should not have been prevented. This result demonstrated that the block in infection for mutant R585A/R588A occurred at the cell attachment stage or internalization stage, and correlated to heparin sulfate binding in vitro.

5.2.2.6 Loop Swapping Confers Heparin Binding to AAV5

Although the primary amino acid sequences are moderately divergent, the architectural position of β-sheets and loops is predicted to be very similar among AAV serotypes (Rabinowitz and Samulski, 2000). It was hypothesized that if R585 and R588 were the critical residues involved in HSPG binding, then it should be possible to substitute that region of AAV2 into AAV5 to create a hybrid virus capable of interacting with heparin-agarose. To achieve this, a recombinant virus, designated rAAV5-HS, was generated by replacing a short loop containing residues 585 through 590 from AAV2 into a region predicted to be structurally equivalent in AAV5 (FIG. 13A). Loop substitution rather than point mutagenesis was done to account for the possibility of additional Van der Waals interactions or hydrophobic contributions from nearby amino acids.

Production and purification of rAAV5-HS was unaffected by the six amino acid substitution (FIG. 13B; Table 5). When rAAV5-HS was tested in the in vitro heparin-agarose binding assay, it was indistinguishable from wild type rAAV2 (FIG. 7C). These data suggested that this region of AAV5 was surface accessible, and that heparin-agarose binding could be artificially conferred by the six amino acids containing R585 and R588.

To compare the infectivity of rAAV5 and rAAV5-HS, packaged viruses were generated that contained a recombinant AAV5 genome in which the GFP reporter gene was flanked by AAV5 terminal repeats. The infectivity of these viruses was compared to rAAV2 in a GCA assay and particle-to-infectivity ratios were calculated as before (FIG. 13D). rAAV5 was able to transduce Hela C12 cells at a low efficiency, approximately 2.5 logs lower than AAV2. However, no transduction was seen with AAV5-HS (<1×10$^4$ IU/ml) (Table 5; FIG. 13D). Given the minimum sensitivity of the GCA assay this meant that the P/I ratio of AAV5-HS was at least 3.5 logs higher than rAAV2 and at least 1 log higher than wild type rAAV5. It was concluded that, although substitution of these five heterologous amino acids into the AAV5 capsid restored heparin binding to the level of AAV2 capsids, it was not sufficient to produce AAV2 levels of infectivity in a cell line normally permissive for AAV2.

5.2.3 Discussion

This example describes the identification of amino acids in the capsid of AAV2 that mediate binding to heparin sulfate proteoglycans. Several lines of evidence suggest that HSPG serves as the primary receptor for AAV2. Inhibition of AAV2 infection can be demonstrated by competition with soluble analogs, GAG desulfation by sodium chlorate treatment, antibody competition, enzymatic removal of heparin, and use of mutant cell lines that express varying levels of HSPG (Handa et al., 2000; Qiu et al., 2000; Summerford and Samulski, 1998; Wu et al., 2000). Binding to heparin sulfate is usually the result of electrostatic charge interactions between basic amino acids (R, K, or H) and negatively charged sulfate residues (Hileman et al., 1998; Mulloy and Linhardt, 2001). During the course of previous mutagenesis studies, many of the basic amino acids in the AAV2 capsid that could potentially contribute to heparin sulfate binding were eliminated (Wu et al., 2000). In this example, the remaining basic residues were examined by looking at their conservation in AAV serotypes 1-5. Those that were present in all five serotypes were not likely to contribute significantly to heparin binding. Those that were conserved in the heparin binding serotypes, AAV1-3, but not in the remaining serotypes were targeted for mutagenesis. Finally, by taking advantage of the fact that R585 and R588 had been previously identified as potential heparin binding amino acids (Wu et al., 2000) and that these amino acids were located in a cluster of basic residues at the three fold axis of symmetry (Xie et al., 2002), all of the basic amino acids in this cluster were also targeted for mutagenesis. This approach yielded a total of 15 amino acids that could have been involved in heparin binding and alanine mutations were characterized at all of these positions. This approach, of course, does not necessarily identify all possible heparin binding amino acids. For example, R484, which is basic in all five serotypes was tested because of its proximity to R585 and R588 and subsequently proved to be involved in heparin binding.

5.2.3.1 Heparin Binding and Infectivity

These studies indicated that capsids with mutations at residue 484, 487, 532, 585 or 588, were partially or completely defective for heparin-agarose binding. The most severe defect was found with mutations in R585 and R588. No binding to heparin sulfate columns could be detected with either mutant (FIG. 8), and both mutations reduced the particle-to-infectivity ratio by two to three logs (Table 5). Mutants that contained substitutions at both positions had even lower infectivity.

The phenotypes of R487A, R585A, and R588A, were probably due largely to defective heparin binding. For example, the double mutant R585A/R588A was approximately 500 fold more defective in cell binding and internalization than wild type (FIG. 12B) when corrected for the MOI, and approximately 2000 fold less infectious (Table 5), as judged by the change in particle-to-infectivity ratio. Another indication that heparin binding was primarily responsible for the defects in R585 and R588 was the fact that conservative mutations at these two positions (R585K and R585K/R588K) produced virus particles with properties similar to wild type (FIG. 8; FIG. 10; FIG. 11; Table 5). Results from the conservative lysine substitutions at R585 and R588 are reasonably consistent with electrostatic attraction being the primary mediator for AAV-heparin interaction. R585K, the least defective heparin binding mutant (FIG. 8), had transduction levels nearly equal to rAAV2 (FIG. 10), and R585K/R588K was only slightly more defective for heparin binding (FIG. 8) and transduction (FIG. 10), and within one log of wild type. Furthermore, when cells were infected at a high MOI, robust transduction was observed for both mutants (FIG. 11). Finally, substitution of a six amino acid sequence containing R585 and R588 imparted heparin binding to AAV5 that was comparable to that seen with AAV2 (FIG. 13). Although similar studies were not performed with the R487 position, it was clear that mutation of R487 produced virus with a more modest defect in heparin binding (FIG. 8) and in infectivity (FIG. 10).

In addition to R487A, R585, and R588, two other mutants were found that were defective for heparin binding, R484A and K532A. R484A and K532A, like R487A, had a more modest effect on binding to heparin sulfate, but unlike the other heparin binding mutants, these two mutations had a dramatic effect on transduction efficiency. Both R484A and R532A were more than 5 logs less infectious than wild type capsids (Table 5; FIG. 10). This severe defect is presumably due to a different block in the infection process that is unrelated to heparin binding, but as yet it has not been identified. The result from K532A is consistent with earlier studies that identified a mutant (mut 37) that contained six amino acid substitutions that included K532A (Wu et al., 2000). Mut 37 had a phenotype identical to K532A in that it produced full virus particles that were non-infectious and more recently has been shown to have a modest defect (approximately 5 fold) in heparin binding and internalization. This potentially maps this defect to a single amino acid.

5.2.3.2 Computer Modeling

Using the recently published atomic structure of AAV2 (PDB ID code: 1LP3) (Xie et al., 2002), the positions of the heparin binding mutations were examined. Symmetry transformation operations from the original PDB file were applied to generate a VP3 trimer arrangement in the context of an icosahedron. When viewed in ribbon format looking directly down a three-fold axis, residues R484, R487, R532, R585 and R588, represented as balls-and-sticks, are located in a linear formation lining one side of each three-fold related spike. When viewed across the top surface of the trimer, residues R585 and R588, which are contributed by one of the peptides in the trimer, are positioned above a linear arrangement of R484, R487 and K532, which are contributed by a second peptide in the trimer. Thus, it appears that a heparin binding motif is formed from some combination of these five amino acids using amino acids from two different polypeptides. An electrostatic potential surface map of a VP3 trimer was also generated, in which areas of positive and negative charge are represented. When viewed perpendicular to the three fold-axis, the five amino acids mapped by this example appear to contribute collectively to a basic patch on one side of each three-fold related spike. The charge, clustering, and surface presentation of these residues are all consistent with a model of electrostatic attraction. Two other basic residues, H526 and K527, contribute to the basic cluster at the three fold spike but these residues do not appear to be involved in heparin binding (FIG. 8).

The five mutations that affected heparin binding were located in the large loop IV region, which among AAV serotypes has low overall sequence conservation and includes all of the previously identified insertion and substitution mutations that affect heparin binding. Interestingly, with the exception of N587, the stretch of amino acids encompassing 585 to 590 is unique to AAV2 and is not present in AAV3, which is the other AAV serotype that has been shown to bind efficiently to heparin sulfate. Mutation of N587 had no effect on heparin-agarose binding and only minor effects on transduction. Conceivably, residues R484, R487 and K532 could be the dominant residues involved in heparin sulfate binding for AAV3.

The apparent dissociation constant ($K_d$) of AAV2 and heparin sulfate was determined by competition analysis to be $2\times10^{9}$M (Qiu et al., 2000). Although this is higher than some heparin-protein interactions, it is sufficiently strong to suggest cooperative binding by one HS glycosaminoglycan chain to multiple attachment points. This example does not address whether heparin sulfate could form a bridge between basic residues in one of the threefold spikes to those in another. However, as the average chain length of heparin glycosaminoglycans varies between 50-200 disaccharide repeats that adopt a helical conformation 40-160 nm in length, it is conceivable that a heparin sulfate chain could wrap around the exterior of the capsid through cooperative binding of multiple spikes at the threefold axis of symmetry. Although a rigorous computational docking analysis was not undertaken, a heparin molecule (PDB ID code 1NTP) was manually superimposed in several orientations that placed multiple reactive sulfate and amine groups within accepted electrostatic attraction distances on pairs of residues spanning the spikes.

5.2.3.3 Mutants that Bind Heparin but are Still Defective

Several new mutants were found that bound heparin sulfate as well as wild type but still produced defective particles. H538A was defective for particle assembly. There are a number of reported examples of mutations that disrupt AAV2 particle formation, several of which are located in the conserved β-strand regions (Rabinowitz et al., 1999; Shi et al., 2001; Wu et al., 2000). Since H358 is neither surface accessible nor in a conserved β-strand, it is possible that it acts internally to stabilize the monomer subunit structure.

Mutants R459A, H509A, and H526A/K527 bound heparin-agarose efficiently but had particle-to-infectivity ratios that were two to more than three logs higher than wild type. Like K532A and R484A, these mutants are presumably defective in some stage of the infectious entry pathway between secondary receptor binding and uncoating. Ongoing studies in the lab are examining the block in infectivity for these mutants.

5.2.3.4 DNA Packaging

The process of DNA packaging is thought to occur by an active process requiring NTP consumption coupled to the helicase activity of the small Rep proteins (King et al., 2001). Although none of the mutations that assembled an A20 positive particle were completely deficient for DNA packaging, mutant R459A produced a 40-fold excess of empty capsid particles compared to rAAV2. Other studies have reported that short insertions at positions 323, 339, 466, 520, 540, 595, 597 that did not interfere with capsid formation still reduced DNA packaging to levels detectable only by PCR™ amplification (Shi et al., 2001). In addition, a point mutant R432A prevents DNA packaging (Wu et al., 2000). Although the relationship between these mutations and their mechanism of action is unclear, it is possible that they disrupt protein-capsid or DNA-capsid interactions.

5.2.3.5 Summary of Exemplary Production System

An exemplary rAAV production system has been described to produce modified rAAV vectors that comprise one or more altered capsid proteins. FIG. 14 shows the results of an immunoslotblot of total capsid protein following standard purification procedures of a representative expression system of the invention. FIG. 15 shows a dot blot autoradiograph of DNA extracted from pTR-UF5 and the system plasmid combinations. FIG. 16 shows the in vivo transduction ability of recombinant AAV vectors produced using various system components. FIG. 17 shows an Immunoblot and dot blot autoradiograph of virions produced from pTR-UF5; pIM45-VP1,2; pIM45-VP1,3; and pIM45-VP2,3 plasmids following standard purification protocols. FIG. 18 shows the in vivo transduction ability of recombinant AAV vectors containing only two capsid proteins, while FIG. 19 depicts an immunoblot of protein fractions collected from iodixinol purified passed over a heparin-agarose column. Using an anti-VP1,2,3 monoclonal antibody. FIG. 20 shows a dot blot autoradiograph of DNA extracted from pTR-UF5 and rAAV R585A, R588A, while FIG. 21 summarizes an exemplary system that demonstrates the in vivo transduction ability of pTR-UF5 and R585A, R588A. FIG. 22 shows a slot blot autoradiograph of an in vivo DNA tracking time course experiment of pTR-UF5, rAAV R585A, R588A, while FIG. 23 shows a schematic diagram of the pIM45 vector showing the rep and cap sequences.

6.0 REFERENCES

The following references, to the extent that they provide exemplary procedural or other details supplementary to those set forth herein, are specifically incorporated herein by reference.

U.S. Pat. No. 4,216,209.
U.S. Pat. No. 4,237,244.
U.S. Pat. No. 4,554,101.
U.S. Pat. No. 4,683,195.
U.S. Pat. No. 4,683,195.
U.S. Pat. No. 4,683,202.
U.S. Pat. No. 4,683,202.
U.S. Pat. No. 4,800,159.
U.S. Pat. No. 4,800,159.
U.S. Pat. No. 4,883,750.
U.S. Pat. No. 4,883,750.
U.S. Pat. No. 4,987,071.
U.S. Pat. No. 4,987,071.
U.S. Pat. No. 5,037,746.
U.S. Pat. No. 5,093,246.
U.S. Pat. No. 5,098,887.
U.S. Pat. No. 5,116,742.
U.S. Pat. No. 5,145,684.
U.S. Pat. No. 5,145,684.
U.S. Pat. No. 5,219,727.
U.S. Pat. No. 5,219,727.
U.S. Pat. No. 5,238,921.
U.S. Pat. No. 5,297,721.
U.S. Pat. No. 5,334,711.
U.S. Pat. No. 5,334,711.
U.S. Pat. No. 5,348,978.
U.S. Pat. No. 5,354,855.
U.S. Pat. No. 5,354,855.
U.S. Pat. No. 5,399,346.
U.S. Pat. No. 5,399,363.
U.S. Pat. No. 5,399,363.
U.S. Pat. No. 5,449,661.
U.S. Pat. No. 5,455,166.
U.S. Pat. No. 5,466,468.
U.S. Pat. No. 5,466,468.
U.S. Pat. No. 5,543,158.
U.S. Pat. No. 5,543,158.
U.S. Pat. No. 5,552,157.
U.S. Pat. No. 5,552,157.
U.S. Pat. No. 5,552,397.
U.S. Pat. No. 5,565,213.
U.S. Pat. No. 5,565,213.
U.S. Pat. No. 5,567,434.
U.S. Pat. No. 5,567,434.
U.S. Pat. No. 5,580,579
U.S. Pat. No. 5,602,306.
U.S. Pat. No. 5,631,359.
U.S. Pat. No. 5,631,359.
U.S. Pat. No. 5,639,655.
U.S. Pat. No. 5,639,940
U.S. Pat. No. 5,641,515
U.S. Pat. No. 5,641,515.
U.S. Pat. No. 5,646,020.
U.S. Pat. No. 5,646,031.
U.S. Pat. No. 5,648,211.
U.S. Pat. No. 5,656,016.
U.S. Pat. No. 5,697,899.
U.S. Pat. No. 5,712,124.
U.S. Pat. No. 5,720,936.
U.S. Pat. No. 5,725,871.
U.S. Pat. No. 5,738,868.
U.S. Pat. No. 5,738,868.
U.S. Pat. No. 5,741,516.
U.S. Pat. No. 5,741,516.
U.S. Pat. No. 5,744,311.
U.S. Pat. No. 5,756,353.
U.S. Pat. No. 5,770,219.
U.S. Pat. No. 5,779,708
U.S. Pat. No. 5,780,045
U.S. Pat. No. 5,783,208
U.S. Pat. No. 5,789,655.
U.S. Pat. No. 5,792,451.
U.S. Pat. No. 5,795,587.
U.S. Pat. No. 5,795,587.
U.S. Pat. No. 5,797,898.
U.S. Pat. No. 5,804,212.
U.S. Pat. No. 5,863,736.
U.S. Pat. No. 5,863,736.
Eur. Pat. Appl. Publ. No. EP 0273085.
Eur. Pat. Appl. Publ. No. EP 0329822.
Eur. Pat. Appl. Publ. No. EP 0360257.
Eur. Pat. Appl. Publ. No. EP 320308.
Eur. Pat. Appl. Publ. No. EP 92110298.4.
Great Britain Pat. Appl. No. 2202328.

Int. Pat. Appl. No. PCT/US87/00880.
Int. Pat. Appl. No. PCT/US87/00880.
Int. Pat. Appl. No. PCT/US88/10315.
Int. Pat. Appl. No. PCT/US88/10315.
Int. Pat. Appl. No. PCT/US89/01025.
Int. Pat. Appl. No. PCT/US89/01025.
Int. Pat. Appl. Publ. No. WO 89/06700.
Int. Pat. Appl. Publ. No. WO 91/03162.
Int. Pat. Appl. Publ. No. WO 92/07065.
Int. Pat. Appl. Publ. No. WO 93/15187.
Int. Pat. Appl. Publ. No. WO 93/23569.
Int. Pat. Appl. Publ. No. WO 94/02595.
Int. Pat. Appl. Publ. No. WO 94/13688.
Int. Pat. Appl. Publ. No. WO89/06700.
Int. Pat. Appl. Publ. No. WO90/07641.
Int. Pat. Appl. Publ. No. WO91/03162.
Int. Pat. Appl. Publ. No. WO92/07065.
Int. Pat. Appl. Publ. No. WO93/15187.
Int. Pat. Appl. Publ. No. WO93/23569.
Int. Pat. Appl. Publ. No. WO94/02595.
Int. Pat. Appl. Publ. No. WO94/13688.
Acton, Scherer, Lodish and Krieger, "Expression cloning of SR-BI, a CD36-related class B scavenger receptor,"*J. Biol. Chem.,* 269:21003-09, 1994.
Adair, Montani, Strick and Guyton, "Vascular development in chick embryos: a possible role for adenosine," *Am. J. Physiol.,* 256:H240-46, 1989.
Afione, Conrad, Kearns, Chunduru, Adams, Reynolds, Guggino, Cutting, Carter and Flotte, "In vivo model of adeno-associated virus vector persistence and rescue," *J. Virol.,* 70:3235-41, 1996.
Afione, Wang, Walsh, Guggino and Flotte, "Delayed expression of adeno-associated virus vector DNA,"*Intervirology,* 42:213-20, 1999.
Agarwal, Shiraishi, Visner and Nick, "Linoleyl hydroperoxide transcriptionally upregulates heme oxygenase-1 gene expression in human renal epithelial and aortic endothelial cells,"*J. Am. Soc. Nephrol.,* 9:1990-97, 1998.
Agbandje, Kajigaya, McKenna, Young and Rossman, "The structure of human parvovirus B19 at 8 Å resolution," *Virol.,* 203:106-15, 1994.
Agbandje, McKenna, Rossman, Strassheim and Parrish, "Structure determination of feline panleuopenia virus empty particles," *Proteins,* 16:155-71, 1993.
Agbandje-McKenna, Llamas-Saiz, Wang, Tattersall and Rossman, "Functional implications of the structure of the murine parvovirus, minute virus of mice," *Structure,* 6:1369-81, 1998.
Aiello, Avery, Arrigg, Keyt, Jampel, Shah, Pasquale, Thieme, Iwamoto, Park, et al., "Vascular endothelial growth factor in ocular fluid of patients with diabetic retinopathy and other retinal disorders," *N. Engl. J. Med.,* 331:1480-87, 1994.
Aiello, Bursell, Clermont, Duh, Ishii, Takagi, Mori, Ciulla, Ways, Jirousek, Smith and King, "Vascular endothelial growth factor-induced retinal permeability is mediated by protein kinase C in vivo and suppressed by an orally effective beta-isoform-selective inhibitor," *Diabetes,* 46:1473-80, 1997.
Aird, Edelberg, Weiler-Guettler, Simmons, Smith and Rosenberg, "Vascular bed-specific expression of an endothelial cell gene is programmed by the tissue microenvironment," *J. Cell Biol.,* 138:1117-24, 1997.
Akagi, Isaka, Akagi, Ikawa, Takenaka, Moriyama, Yamauchi, Horio, Ueda, Okabe and Imai, "Transcriptional activation of a hybrid promoter composed of cytomegalovirus enhancer and β-actin/β-globin gene in glomerular epithelial cells in vivo," *Kidney Int.,* 51:1265-69, 1997.
Alejandro, Lehmann, Ricordi, Kenyon, Angelico, Burke, Esquenazi, Nery, Betancourt, Kong, Miller and Mintz, "Long-term function (6 years) of islet allografts in type 1Type I diabetes," *Diabetes,* 46:1983-89, 1997.
Allen and Choun, "Large unilamellar liposomes with low uptake into the reticuloendothelial system," *FEBS Lett.,* 223:42-46, 1987.
Altschuler, Tritz and Hampel, *Gene,* 122:85-90, 1992.
Ardekani, Greenberger and Jahroudi, "Two repressor elements inhibit expression of the von Willebrand factor gene promoter in vitro," *Thromb. Haemost.,* 80:488-94, 1998.
Arreaza, Cameron, Jaramillo, Gill, Hardy, Laupland, Rapoport, Zucker, Chakrabarti, Chensue, Qin, Singh and Delovitch, "Neonatal activation of CD28 signaling overcomes T cell energy and prevents autoimmune diabetes by an IL-4-dependent mechanism,"*J. Clin. Invest.,* 100:2243-53, 1997.
Asahara, Murohara, Sullivan, Silver, van der Zee, Li, Witzenbichler, Schatteman and Isner, "Isolation of putative progenitor endothelial cells for angiogenesis," *Science,* 275:964-67, 1997.
Atchinson et al., *Science* 194:754-56, 1965.
Atchison, Casto and Hammon, "Electron microscopy of adenovirus-associated virus (AAV) in cell cultures," *Virology,* 29:353-57, 1966.
Atkinson and Eisenbarth, "Type 1 diabetes: new perspectives on disease pathogenesis and treatment," *Lancet,* 358:221-29, 2001.
Atkinson and Leiter, "The NOD mouse model of type 1Type I diabetes: as good as it gets?,"*Nat. Med.,* 5:601-04, 1999.
Atkinson and Maclaren, "The pathogenesis of insulin-dependent diabetes mellitus," *N. Engl. J. Med.,* 331:1428-36, 1994.
Auricchio, O'Connor, Hildinger and Wilson, "A single-step affinity column for purification of serotype-5 based adeno-associated viral vectors,"*Mol. Ther.,* 4:372-74, 2001.
Bach, "Insulin dependent diabetes mellitus as a beta-cell targeted disease of immunoregulation," *J. Autoimmun.,* 8:439-463, 1995.
Bach, "Insulin-dependent diabetes mellitus as an autoimmune disease," *Endocr. Rev.,* 15:516-42, 1994.
Bach and Chatenoud, "Tolerance to islet autoantigens in Type 1 diabetes," *Annu. Rev. Immunol.,* 19:131-61, 2001.
Balasa and Sarvetnick, "The paradoxical effects of interleukin 10 in the immunoregulation of autoimmune diabetes," *J. Autoimmun.,* 9:283-86, 1996.
Balasa, La Cava, Van Gunst, Mocnik, Balakrishna, Nguyen, Tucker and Sarvetnick, "A mechanism for IL-10-mediated diabetes in the nonobese diabetic (NOD) mouse: ICAM-1 deficiency blocks accelerated diabetes," *J. Immunol.,* 165:7330-37, 2000a.
Balasa, Van Gunst, Jung, Balakrishna, Santamaria, Hanafusa, Itoh and Sarvetnick, "Islet-specific expression of IL-10 promotes diabetes in nonobese diabetic mice independent of Fas, perforin, TNF receptor-1, and TNF receptor-2 molecules," *J. Immunol.,* 165:2841-47, 2000b.
Balazsovits, Mayer, Bally, Cullis, McDonell, Ginsberg and Falk, "Analysis of the effect of liposome encapsulation on the vesicant properties, acute and cardiac toxicities, and antitumor efficacy of doxorubicin," *Cancer Chemother. Pharmacol.,* 23:81-86, 1989.
Bantel Schaal and zur Hausen, "Characterization of the DNA of a defective human parvovirus isolated from a genital site," *Virology,* 134:52-63, 1984.

Barbis, Chang and Parrish, "Mutations adjacent to the dimple of the canine parvovirus capsid structure affect sialic acid binding," *Virol.*, 191:301-08, 1992.

Barcz, Sommer, Sokolnicka, Gawrychowski, Roszkowska-Purska, Janik and Skopinska-Rozewska, "The influence of theobromine on angiogenic activity and proangiogenic cytokines production of human ovarian cancer cells," *Oncol. Rep.*, 5:517-20, 1998.

Barrijal, Perros, Gu, Avalosse, Belenguer, Amalric and Rommelaere, "Nucleolin forms a specific complex with a fragment of the viral (minus) strand of minute virus of mice DNA," *Nucleic Acids Res.*, 20:5053-60, 1992.

Bartlett and Samulski, "Fluorescent viral vectors: a new technique for the pharmacological analysis of gene therapy," *Nat. Med.*, 4:635-7, 1998.

Bartlett et al., "Long-term expression of a fluorescent reporter gene via direct injection of plasmid vector into mouse skeletal muscle: Comparison of human creatine kinase and CMV promoter expression levels in vivo," *Cell Transplant.*, 5(3):411-419, 1996.

Bartlett Kleinschmidt, Boucher and Samulski, "Targeted adeno-associated virus vector transduction of nonpermissive cells mediated by a bispecific F(ab'γ)2 antibody," *Nat. Biotechnol.*, 17:181-86, 1999.

Baskar, Smith, Ciment, Hoffmann, Tucker, Tenney, Colberg-Poley, Nelson and Ghazal, "Developmental analysis of the cytomegalovirus enhancer in transgenic animals," *J. Virol.*, 70:3215-26, 1996.

Baskar, Smith, Nilayer, Jupp, Hoffmann, Peffer, Tenney, Colberg-Poley, Ghazal and Nelson, "The enhancer domain of the human cytomegalovirus major immediate-early promoter determines cell type-specific expression in transgenic mice," *J. Virol.*, 70:3207-14, 1996.

Becerra, Koczot, Fabisch and Rose, "Synthesis of adeno-associated virus structural proteins requires both alternative mRNA splicing and alternative initiations from a single transcript," *J. Virol.*, 62:2745-54, 1988.

Becerra, Rose, Hardy, Baroudy and Anderson, "Direct mapping of adeno-associated virus capsid proteins B and C: a possible ACG initiation codon," *Proc. Natl. Acad. Sci. USA*, 82:7919-23, 1985.

Beck, Jones, Chesnut, Walsh, Reynolds, Carter, Askin, Flotte and Guggino, "Repeated delivery of adeno-associated virus vectors to the rabbit airway,"*J. Virol.*, 73:9446-55, 1999.

Beck, Powell-Braxton, Widmer, Valverde and Hefti, "Igf1 gene disruption results in reduced brain size, CNS hypomyelination, and loss of hippocampal granule and striatal parvalbumin-containing neurons," *Neuron*, 14:717-30, 1995.

Bendelac, Carnaud, Boitard and Bach, "Syngeneic transfer of autoimmune diabetes from diabetic NOD mice to healthy neonates. Requirement for both L3T4+ and Lyt-2+ T cells, "*J. Exp. Med.*, 166:823-32, 1987.

Benhamou, Mullen, Shaked, Bahmiller and Csete, "Decreased alloreactivity to human islets secreting recombinant viral interleukin 10," *Transplantation*, 62:1306-12, 1996.

Bennett et al., "Adenovirus-mediated delivery of rhodopsin-promoted bcl-2 results in a delay in photoreceptor cell death in the rd/rd mouse," *Gene Ther.*, 5(9):1156-1164, 1998.

Bennett, Duan, Engelhardt and Maguire, "Real-time, noninvasive in vivo assessment of adeno-associated virus-mediated retinal transduction," *Invest. Ophthalmol. Vis. Sci.*, 38:2857-2863, 1997.

Bennett, Maguire, Cideciyan, Schnell, Glover, Anand, Aleman, Chirmule, Gupta, Huang, Gao, Nyberg, Tazelaar, Hughes, Wilson and Jacobson, "Stable transgene expression in rod photoreceptors after recombinant adeno-associated virus-mediated gene transfer to monkey retina," *Proc. Nat'l Acad. Sci. USA*, 96:9920-25, 1999.

Berns and Bohenzky, "Adeno-associated viruses: an update," *Adv. Virus Res.*, 32:243-306, 1987.

Berns and Giraud, "Adenovirus and adeno-associated virus as vectors for gene therapy,"*Ann. N.Y. Acad. Sci.*, 772:95-104, 1995.

Berns and Giraud, "Biology of adeno-associated virus," *Curr. Top. Microbiol. Immunol.*, 218:1-23, 1996.

Berns and Linden, "The cryptic life style of adeno-associated virus," *Bioessays*, 17:237-45, 1995.

Berns et al., In VIRUS PERSISTENCE, Mehay et al. (ed.), Cambridge Univ. Press, pp. 249-265, 1982.

Berns, In FIELDS VIROLOGY, Fields, (ed.), Raven Press, Philadelphia, Pa., pp. 2173-97, 1996.

Berns, In THE PARVOVIRUSES, Plenum Press, New York, 1984.

Berns, Kotin and Labow, "Regulation of adeno-associated virus DNA replication," *Biochim. Biophys. Acta*, 951:425-29, 1988.

Berns, Pinkerton, Thomas and Hogagn, "Detection of adeno-associated virus (AAV)-specific nucleotide sequences in DNA isolated from latently infected Detroit 6 cells," *Virology*, 68:556-60, 1975.

Bikfalvi and Han, "Angiogenic factors are hematopoietic growth factors and vice versa," *Leukemia*, 8:523-29, 1994.

Binley, Iqball, Kingsman, Kingsman and Naylor, "An adenoviral vector regulated by hypoxia for the treatment of ischaemic disease and cancer," *Gene Ther.*, 6:1721-27, 1999.

Birikh, Heaton and Eckstein, "The structure, function and application of the hammerhead ribozyme,"*Eur. J. Biochem.*, 245:1-16, 1997.

Blacklow, "Adeno-associated viruses of humans, p. 165-174," in PARVOVIRUSES AND HUMAN DISEASE, Pattison (ed.), CRC Press, Boca Raton, Fla., 1988.

Blacklow, Dolin and Hoggan, "Studies of the enhancement of an adenovirus-associated virus by herpes simplex virus,"*J. Gen. Virol.*, 10:29-36, 1971.

Blacklow, Hoggan and Rowe, "Isolation of adenovirus-associated viruses from man," *Proc. Natl. Acad. Sci. USA*, 58:1410-15, 1967.

Blacklow, Hoggan and Rowe, "Serologic evidence for human infection with adenovirus-associated viruses,"*J. Natl. Cancer Inst.*, 40:319-27, 1968a.

Blacklow, Hoggan, Kapikian, Austin and Rowe, "Epidemiology of adenovirus-associated virus infection in a nursery population,"*Am. J. Epidemiol.*, 88:368-78, 1968b.

Blacklow, Hoggan, Sereno, Brandt, Kim, Parrott and Chanock, "A seroepidemiologic study of adenovirus-associated virus infection in infants and children," *Am. J. Epidemiol.*, 94:359-66, 1971.

Boast, Binley, Iqball, Price, Spearman, Kingsman, Kingsman and Naylor, "Characterization of physiologically regulated vectors for the treatment of ischemic disease," *Hum. Gene Ther.*, 10:2197-208, 1999.

Borriello and Krauter, "Multiple murine alpha 1-protease inhibitor genes show unusual evolutionary divergence," *Proc. Nat'l Acad. Sci. USA*, 88:9417-21, 1991.

Boskovic and Twining, "Local control of α1-proteinase inhibitor levels: regulation of α1-proteinase inhibitor in the human cornea by growth factors and cytokines," *Biochim. Biophys. Acta*, 1403:37-46, 1998.

Bottino, Fernandez, Ricordi, Lehmann, Tsan, Oliver and Inverardi, "Transplantation of allogenic islets of Langerhans in the rat liver: effects of macrophage depletion on graft survival and microenvironment activation," *Diabetes*, 47:316-23, 1998.

Bourlais, Acar, Zia, Sado, Needham, Leverge, "Ophthalmic drug delivery systems—recent advances," *Prog. Retin Eye Res.*, 17(1):33-58, 1998.

Bowman, Campbell, Darrow, Ellis, Suresh and Atkinson, "Immunological and metabolic effects of prophylactic insulin therapy in the NOD-scid/scid adoptive transfer model of IDDM," *Diabetes*, 45:205-08, 1996.

Brantly, Wittes, Vogelmeier, Hubbard, Fells and Crystal, *Chest*, 100:703-08, 1991.

Brass, Crawford, Narciso and Gollan, "Evaluation of University of Wisconsin cold-storage solution in warm hypoxic perfusion of rat liver: the addition of fructose reduces injury," *Gastroenterology*, 105:1455-63, 1993.

Breakefield et al., TREATMENT OF GENETIC DISEASES, Churchill Livingstone, Inc., 1991. Briggs, Kadonga, Bell and Tjian, *Science*, 234:47-52, 1986.

Brown and Jampol, "New concepts of regulation of retinal vessel tone," *Arch. Ophthalmol.*, 114:199-204, 1996.

Brown, Reading, Jones, Fitchett, Howl, Martin, Longland, Michelangeli, Dubrova and Brown, "Critical evaluation of ECV304 as a human endothelial cell model defined by genetic analysis and functional responses: a comparison with the human bladder cancer derived epithelial cell line T24/83," *Lab. Invest.*, 80:37-45, 2000.

Brown, Twells, Hey, Cox, Levy et al., "Isolation and characterization of LRP6, a novel member of the low density lipoprotein receptor gene family," *Biochem. Biophys. Res. Commun.*, 248:879-88, 1998.

Buijn et al., *Science*, 281:1851-1853, 1998.

Buller, "Herpes simplex virus types 1 and 2 completely help adenovirus-associated virus replication," *J. Virol.*, 40:241-47, 1981.

Buller and Rose, "Characterization of adenovirus-associated virus-induced polypeptides in KB cells," *J. Virol.*, 25:331-38, 1978.

Buller, Janik, Sebring and Rose, "Herpes simplex virus types 1 and 2 completely help adenovirus-associated virus replication," *J. Virol.*, 40:241-47, 1981.

Burcin, Schiedner, Kochanek, Tsai and O'Malley, "Adenovirus-mediated regulable target gene expression in vivo," *Proc. Natl. Acad. Sci. USA*, 96:355-60, 1999.

Caldovic and Hackett Jr., "Development of position-independent expression vectors and their transfer into transgenic fish," *Mol. Mar. Biol. Biotechnol.*, 4(1):51-61, 1995.

Cameron, Areaza, Zucker, Chensue, Stricter, Chaaakrabaarti and Delovitch, "IL-4 prevents insulitis and insulin-dependent diabetes mellitus in nonobese diabetic mice by potentiation of regulatory T helper-2 cell function," *J. Immunol.*, 159:4686-92, 1997.

Cameron, Strathdee, Holmes, Arreaza, Dekaban and Delovitch, "Biolistic-mediated interleukin 4 gene transfer prevents the onset of type 1 Type I diabetes," *Hum. Gene Ther.*, 11: 1647-56, 2000.

Cao, Zhao, Stangl, Hasegawa, Richardson, Parker and Hobbs, "Developmental and hormonal regulation of murine scavenger receptor, class B, type 1," *Mol. Endocrinol.*, 13:1460-73, 1999.

Capecchi, "High efficiency transformation by direct microinjection of DNA into cultured mammalian cells," *Cell*, 22:479-88, 1980.

Carrell et al., "Structure and variation of human alpha 1-antitrypsin," *Nature*, 298:329-34, 1982.

Carroll, Rilo, Alejandro, Zeng, Khan, Fontes, Tzakis, Carr and Ricordi, "Long-term (>3-year) insulin independence in a patient with pancreatic islet cell transplantation following upper abdominal exenteration and liver replacement for fibrolamellar hepatocellular carcinoma," *Transplantation*, 59:875-79, 1995.

Carter and Flotte, "Development of adeno-associated virus vectors for gene therapy of cystic fibrosis," *Curr. Top. Microbiol. Immunol.*, 218:119-44, 1996.

Carter et al., In THE PARVOVIRUSES, Berns (ed.), Plenum, N.Y., pp. 153-207, 1983.

Carter, "The growth of adeno-associated virus," In HANDBOOK OF PARVOVIRUSES, Tijssen (ed.), CRC Press, Boca Raton, pp. 155-68, 1990.

Carter, Khoury and Denhardt, "Physical map and strand polarity of specific fragments of adenovirus-associated virus DNA produced by endonuclease R-EcoRI," *J. Virol.*, 16:559-68, 1975.

Carter, Marcus-Sekura, Laughlin and Ketner, "Properties of an adenovirus type 2 mutant, Ad2d1807, having a deletion near the right-hand genome terminus: failure to help AAV replication," *Virology*, 126:505-16, 1983.

Carter, Mendelson and Trempe, HANDBOOK OF PARVOVIRUSES, CRC Press, Boca Raton, pp. 169-226, 1990.

Carver, Dalrymple, Wright, Cottom, Reeves, Gibson, Keenan, Barrass, Scott, Colman, et al., "Transgenic livestock as bioreactors: stable expression of human alpha-1-antitrypsin by a flock of sheep," *Biotechnology NY*, 11(11): 1263-1270, 1993.

Casto, Armstrong, Atchison and Hammon, "Studies on the relationship between adeno-associated virus type 1 (AAV-1) and adenoviruses. II. Inhibition of adenovirus plaques by AAV; its nature and specificity," *Virol.*, 33:452-58, 1967.

Cech, *Annu. Rev. Biochem.*, 59:543-69, 1990.

Cech, *Biochem. Int.*, 18:7-14, 1989.

Cech et al., "In vitro splicing of the ribosomal RNA precursor of Tetrahymena: involvement of a guanosine nucleotide in the excision of the intervening sequence," *Cell*, 27(3 Pt 2):487-496, 1981.

Chakravarthy, Stitt, McNally et al., *Curr. Eye Res.*, 14:285-94, 1995.

Challberg, "A method for identifying the viral genes required for herpesvirus DNA replication," *Proc. Natl. Acad. Sci. USA*, 83:9094-103, 1986.

Chandran, Roy, Mishra, "Recent trends in drug delivery systems: liposomal drug delivery system—preparation and characterization," *Indian J. Exp. Biol.*, 35(8):801-809, 1997.

Chang and Prud'homme, "Intramuscular administration of expression plasmids encoding interferon-gamma receptor/IgG1 or IL-4/IgG1 chimeric proteins protects from autoimmunity," *J. Gene Med.*, 1:415-23, 1999.

Chao, Liu, Rabinowitz, Li, Samulski and Walsh, "Several log increase in therapeutic transgene delivery by distinct adeno-associated viral serotype vectors," *Mol. Ther.*, 2:619-23, 2000.

Chapman and Rossman, "Structure, sequence, and function correlations among parvoviruses," *Virol.*, 194:491-508, 1993.

Chejanovsky and Carter, "Mutagenesis of an AUG codon in the adeno-associated virus rep gene: effects on viral DNA replication," *Virology*, 173:120-28, 1989.

Chen and Okayama, "High-efficiency transformation of mammalian cells by plasmid DNA," *Mol. Cell. Biol.*, 7:2745-52, 1987.

Chen et al., "Multitarget-ribozyme directed to cleave at up to nine highly conserved HIV-1 env RNA regions inhibits HIV-1 replication—potential effectiveness against most presently sequenced HIV-1 isolates," *Nucl. Acids Res.,* 20:4581-4589, 1992.

Cheung, Hoggan, Hauswirth and Berns, "Integration of the adeno-associated virus genome into cellular DNA in latently infected human Detroit 6 cells," *J. Virol.,* 33:739-48, 1980.

Chiocca, Choi, Cai, DeLuca, Schaffer, DiFiglia, Breakefield and Martuza, "Transfer and expression of the lacZ gene in rat brain neurons mediated by herpes simplex virus mutants," *The New Biologist,* 2:739-46, 1990.

Chiorini, Kim, Yang and Kotin, "Cloning and characterization of adeno-associated virus type 5," *J. Virol.,* 73:1309-19, 1999.

Chiorini, Wendtner, Urcelay, Safer, Hallek and Kotin, "High-efficiency transfer of the T cell co-stimulatory molecule B7-2 to lymphoid cells using high-titer recombinant adeno-associated virus vectors," *Hum. Gene Ther.,* 6:1531-41, 1995.

Chiorini, Yang, Liu, Safer and Kotin, "Cloning of adeno-associated virus type 4 (AAV4) and generation of recombinant AAV4 particles,"*J. Virol.,* 71:6823-33, 1997.

Chowrira and Burke, "Extensive phosphorothioate substitution yields highly active and nuclease-resistant hairpin ribozymes," *Nucl. Acids Res.,* 20:2835-2840, 1992.

Churg, Dai, Zay, Karsan, Hendricks, Yee, Martin, MacKenzie, Xie, Zhang, Shapiro and Wright, "α-1-antitrypsin and a broad spectrum metalloprotease inhibitor, RS113456, have similar acute anti-inflammatory effects," *Lab. Invest.,* 81:1119-31, 2001.

Cipolla, Porter and Osol, *Stroke,* 28:405-11, 1997.

Clark, Liu, McGrath and Johnson, "Highly purified recombinant adeno-associated virus vectors are biologically active and free of detectable helper and wild-type viruses," Hum. *Gene Ther.* 10:1031-39, 1999.

Clark, Sferra and Johnson, "Recombinant adeno-associated viral vectors mediate long-term transgene expression in muscle," *Hum. Gene Ther.,* 8:659-69, 1997.

Clark, Voulgaropoulou and Johnson, "A stable cell line carrying adenovirus-inducible rep and cap genes allows for infectivity titration of adeno-associated virus vectors," *Gene Therapy* 3:1124-32, 1996.

Clark, Voulgaropoulou, Fraley and Johnson, "Cell lines for the production of recombinant adeno-associated virus," *Hum. Gene Ther.,* 6:1329-41, 1995.

Clemmons, "IGF binding proteins: regulation of cellular actions," *Growth Regul.,* 2:80-87, 1992.

Cleveland, *Neuron,* 23:515-520, 1999.

Collins and Olive, "Reaction conditions and kinetics of self-cleavage of a ribozyme derived from *Neurospora* VS RNA," *Biochem.,* 32(11):2795-2799, 1993.

Conrad, Allen, Afione, Reynolds, Beck, Fee-Maki, Barrazza-Ortiz, Adams, Askin, Carter, Guggino and Flotte, "Safety of single-dose administration of an adeno-associated virus (AAV)-CFTR vector in the primate lung," *Gene Ther.,* 3:658-68, 1996.

Cook and McCormick, "Inhibition by cAMP of Ras-dependent activation of Raf," *Science,* 262:1069-72, 1993.

Cosentino, Hishikawa, Katusic and Luscher, *Circulation,* 96:25-28, 1997.

Coune, "Liposomes as drug delivery system in the treatment of infectious diseases: potential applications and clinical experience," *Infection,* 16:141-47, 1988.

Couvreur, "Polyalkyleyanoacrylates as colloidal drug carriers," *Crit. Rev. Ther. Drug Carrier Syst.,* 5:1-20, 1988.

Couvreur, Kante, Lenaerts, Scailteur, Roland and Speiser, "Tissue distribution of antitumor drugs associated with polyalkylcyanoacrylate nanoparticles," *J. Pharm. Sci.,* 69:199-202, 1980.

Couvreur, Tulkens, Roland, Trouet and Speiser, "Nanocapsules, a new lysosomotropic carrier," *FEBS Lett.,* 84:323-26, 1977.

Cowan, Baron, Crack, Coulber, Wilson and Rabinovitch, "Elafin, a serine elastase inhibitor, attenuates post-cardiac transplant coronary arteriopathy and reduces myocardial necrosis in rabbits after heterotopic cardiac transplantation," *J. Clin. Invest.,* 97:2452-68, 1996.

Cozzi, Tucker, Langford, Pino-Chavez, Wright, O'Connell, Young, Lancaster, McLanghlin, Hunt, Bordin, White, "Characterization of pigs transgenic for human decay-accelerating factor," *Transplantation,* 64(10):1383-1392, 1997.

Cretin, Buhler, Fournier, Caulfield, Oberholzer, Mentha and Morel, "Human islet allotransplantation: world experience and current status," *Dig. Surg.,* 15:656-62, 1998.

Crute, Tsurumi, Zhu, Weller, Olivo, Challberg, Mocarski and Lehman, "Herpes simplex virus 1 helicase-primase: a complex of three herpes-encoded gene products," *Proc. Natl. Acad. Sci. USA,* 86:2186-94, 1989.

Cukor, Blacklow, Hoggan and Berns, in THE PARVOVIRUSES, Berns (ed.), Plenum Press, NY, pp. 33-66, 1983.

Cunningham and Wells, "High resolution epitope mapping of hGH-receptor interactions by alanine-scanning mutagenesis," *Science,* 244:1081-85, 1989.

Curiel, Agarwal, Wagner and Cotton, "Adenovirus enhancement of transferrin-polylysine-mediated gene delivery," *Proc. Natl. Acad. Sci. USA,* 88:8850-54, 1991.

Cusi and DeFronzo, "Treatment of NIDDM, IDDM and other insulin-resistant states with IGF-I: physiological and clinical considerations,"*Diabetes Rev.,* 3:206-36, 1995.

D'Angelo, Lee and Weiner, "cAMP-dependent protein kinase inhibits the mitogenic action of vascular endothelial growth factor and fibriblast growth factor in capillary endothelial cells by blocking Raf activation," *J. Cell Biochem.,* 67:353-366, 1997.

Daiger, Rossiter, Greenberg, Christoffels and Hide, "Data services and software for identifying genes and mutations causing retinal degeneration," *Invest. Ophthalmol. Vis. Sci.,* 39:S295, 1998.

Daiger, Sullivan and Rodriguez, *Behavioral Brain Sci.,* 18:452-67, 1995.

Daly, Vogler, Levy, Haskins and Sands, "Neonatal gene transfer leads to widespread correction of pathology in a murine model of lysosomal storage disease," *Proc. Nat'l Acad. Sci. USA,* 96:2296-300, 1999.

Damert, Ikeda and Risau, "Activator-protein-1 binding potentiates the hypoxia-induciblefactor-1-mediated hypoxia-induced transcriptional activation of vascular-endothelial growth factor expression in C6 glioma cells," *Biochem. J.,* 327:419-23, 1997.

Datta, Chaddaha, Garber, Chung, Tytler, Dashti, Bradley, Gianturco and Anantharamaiah, "The receptor binding domain of apolipoprotein E, linked to a model class A amphipathic helix, enhances internalization and degradation of LDL by fibroblasts," *Biochem.,* 39:213-220, 2000.

Davidson, Stein, Heth, Martins, Kotin, Derksen, Zabner, Chodsi and Chiorini, "Recombinant adeno-associated virus type 2, 4, and 5 vectors: transduction of variant cell types and regions in the mammalian central nervous system," *Proc. Natl. Acad. Sci. USA,* 97:3428-43, 2000.

Davies, Mueller, Minson, Oconner, Krahl and Sarvetnick, "Interleukin-4 secretion by the allograft fails to affect the allograft-specific interleukin-4 response in vitro," *Transplantation*, 67:1583-89, 1999.

Davis, Szarowski, Turner, Morrisett and Shain, "In vivo activation and in situ BDNF-stimulated nuclear translocation of mitogen-activated/extracellular signal-regulated protein kinase is inhibited by ethanol in the developing rat hippocampus," *Neurosci. Lett.*, 272:95-98, 1999.

Delovitch and Singh, "The nonobese diabetic mouse as a model of autoimmune diabetes: immune dysregulation gets the NOD," *Immunity*, 7:727-38, 1997.

DeLuca and Schaffer, "Activities of herpes simplex virus type 1 (HSV-1) ICP4 genes specifying nonsense peptides," *Nucleic Acids Res.*, 15:4491-511, 1987.

DeLuca, McCarthy and Schaffer, "Isolation and characterization of deletion mutants of herpes simplex virus type 1 in the gene encoding immediate-early regulatory protein ICP4,"*J. Virol.*, 56:558-70, 1985.

Deng, Ketchum, Yang, Kucher, Weber, Shaked, Naji and Brayman, "IL-10 and TGF-β gene transfer to rodent islets: effect on xenogeneic islet graft survival in naive and B-cell-deficient mice," *Trans. Proc.*, 29:2207-08, 1997.

Deshpande, Chopra, Rangarajan, Shashidhara, Rodrigues and Krishna, *J. Biol. Chem.*, 272:10664-68, 1997.

DesJardin and Hauswirth*inv. Inv. Ophth. Vis. Sci.*, 37:154-65, 1996.

Dhami, Gilks, Xie, Zay, Wright and Churg, "Acute cigarette smoke-induced connective tissue breakdown is mediated by neutrophils and prevented by α1-antitrypsin," *Am. J. Respir. Cell Mol. Biol.*, 22:244-52, 2000.

Dills, Moss, Klein and Klein, "Association of elevated IGF-I levels with increased retinopathy in late-onset diabetes," *Diabetes*, 40:1725-30, 1991.

Ding, Qin, Kotenko, Pestka and Bromberg, "A single amino acid determines the immunostimulatory activity of interleukin 10,*" J. Exp. Med.*, 191:213-23, 2000.

Donello, Loeb and Hope, "Woodchuck hepatitis virus contains a tripartite posttranscriptional regulatory element," *J. Virol.*, 72:5085-92, 1998.

Dong, Fan and Frizzell, "Quantitative analysis of the packaging capacity of recombinant adeno-associated virus," *Hum. Gene Ther.*, 7:2101-12, 1996.

Douglas, Davis and Illum, "Nanoparticles in drug delivery," *Crit. Rev. Ther. Drug Carrier Syst.*, 3:233-61, 1987.

Drenser, Timmers, Hauswirth and Lewin, "Ribozyme-targeted destruction of RNAs associated with ADRP," *Inv. Ophth. Vis. Sci.*, 39:681-689, 1998.

Dropulic, Lin, Martin, Jeang, "Functional characterization of a U5 ribozyme: intracellular suppression of human immunodeficiency virus type 1 expression," *J. Virol.*, 66(3):1432-41, 1992.

Dryja and Berso, "Retinitis pigmentosa and allied diseases. Implications of genetic heterogeneity,"*Invest. Ophthalmol. Vis. Sci.*, 36:1197-1200, 1995.

Duan, Li, Kao, Yue, Pessin and Engelhardt, "Dynamin is required for recombinant adeno-associated virus type 2 infection,"*J. Virol.*, 73:10371-76, 1999.

Duan, Yue, Yan and Engelhardt, "A new dual-vector approach to enhance recombinant adeno-associated virus-mediated gene expression through intermolecular cis activation," *Nat. Med.*, 6:595-98, 2000.

Dunn, "Problems related to immunosuppression. Infection and malignancy occurring after solid organ transplantation," *Crit. Care Clin.*, 6:955-77, 1990.

Dunn, Hardman, Kari and Barrett, "Insulin-like growth factor 1 (IGF-1) alters drug sensitivity of HBL100 human breast cancer cells by inhibition of apoptosis induced by diverse anticancer drugs," *Cancer Res.*, 57:2687-93, 1997.

During et al., "Peroral gene therapy of lactose intolerance using an adeno-associated virus vector," *Nature Med.*, 4:1131-1135, 1998.

Dusseau and Hutchins, "Hypoxia-induced angiogenesis in chick chorioallantoic membranes: a role for adenosine," *Respir. Physiol.*, 17:33-44, 1988.

Dusseau, Hutchins and Malbasa, "Stimulation of angiogenesis by adenosine on the chick chorioallantoic membrane," *Circ. Res.*, 59:163-70, 1986.

Ebert and Bunn, "Regulation of transcription by hypoxia requires a multiprotein complex that includes hypoxia-inducible factor 1, an adjacent transcription factor, and p300/CREB binding protein,"*Mol. Cell Biol.*, 18:4089-96, 1998.

Ebert, Selgrath, DiTullio, Denman, Smith, Memon, Schindler, Monastersky, Vitale, Gordon, "Transgenic production of a variant of human tissue-type plasminogen activator in goat milk: generation of transgenic goats and analysis of expression," *Biotechnology NY*, 9(9):835-838, 1991.

Eglitis and Anderson, "Retroviral vectors for introduction of genes into mammalian cells," *Biotechniques* 6(7):608-614, 1988.

Eglitis, Kantoff, Kohn, Karson, Moen, Lothrop, Blaese, Anderson, "Retroviral-mediated gene transfer into hemopoietic cells,"*Avd. Exp. Med. Biol.*, 241:19-27, 1988.

Eisen and Brown, "DNA arrays for analysis of gene expression," *Methods Enzymol.*, 303:179-205, 1999.

Ellis, Guberski, Somogyi-Mann and Grant, "Increased $H_2O_2$, vascular endothelial growth factor and receptors in the retina of the BBZ/Wor diabetic rat." *Free Radic. Biol. Med.*, 28:91-101, 2000.

Elroy-Stein and Moss, "Cytoplasmic expression system based on constitutive synthesis of bacteriophage T7 RNA polymerase in mammalian cells," *Proc. Natl. Acad. Sci. USA*, 87:6743-7, 1990.

Ethier, Chander and Dobson, Jr., "Adenosine stimulates proliferation of human endothelial cells in culture,"*Am. J. Physiol.*, 265:H131-38, 1993.

Faktorovich, Steinberg, Yasamura et al., *Nature*, 347:83-86, 1990.

Faller and Baltimore, "Liposome encapsulation of retrovirus allows efficient super infection of resistant cell lines,"*J. Virol.*, 49:269-72, 1984.

Fechheimer, Boylan, Parker, Sisken, Patel and Zimmer, "Transfection of mammalian cells with plasmid DNA by scrape loading and sonication loading," *Proc. Natl. Acad. Sci. USA*, 84:8463-67, 1987.

Fedor and Uhlenbeck, "Substrate sequence effects on 'hammerhead' RNA catalytic efficiency,"*Proc. Nat'l Acad. Sci. USA*, 87:1668-1672, 1990.

Fellowes, Etheridge, Coade, Cooper, Stewart, Miller and Woo, "Amelioration of established collagen induced arthritis by systemic IL-10 gene delivery," *Gene Ther.*, 7:967-77, 2000.

Ferrari, Samulski, Shenk and Samulski, "Second strand synthesis is a rate-limiting step for efficient transduction by recombinant adeno-associated virus vectors," *J. Virol.*, 70:3227-34, 1996.

Ferrari, Xiao, McCarty and Samulski, *Nature Med.*, 3:1295-97, 1997.

Ferreira, Assouline, Schwachtgen, Bahnak, Meyer and Kerbiriou-Nabias, "The role of the 5'-flanking region in the cell-specific transcription of the human von Willebrand factor gene," *Biochem. J.*, 293:641-48, 1993.

Fife, Bower, Cooper, Stewart, Etheridge, Coombes, Buluwela and Miller, "Endothelial cell transfection with cationic liposomes and herpes simplex-thymidine kinase mediated killing," *Gene Ther.*, 5:614-20, 1998.

Finkenzeller, Sparacio, Technau, Marme and Siemeister, "Sp1 recognition sites in the proximal promoter of the human vascular endothelial growth factor gene are essential for platelet-derived growth factor-induced gene expression," *Oncogene*, 15:669-76, 1997.

Fischer et al., "Induction of alpha1-antitrypsin synthesis in human articular chondrocytes by interleukin-6-type cytokines: evidence for a local acute-phase response in the joint," *Arthritis Rheum.*, 42:1936-45, 1999.

Fisher, Gao, Weitzman, DeMatteo, Burda and Wilson, "Transduction with recombinant adeno-associated virus for gene therapy is limited by leading-strand synthesis," *J. Virol.*, 70:520-32, 1996.

Fisher, Jooss, Alston, Yang, Haecker, High, Pathak, Raper and Wilson, "Recombinant adeno-associated virus for muscle directed gene therapy," *Nat. Med.*, 3:306-12, 1997.

Fisher-Adams, Wong, Podsakoff, Forman and Chatterjee, "Integration of adeno-associated virus vectors in CD34+ human hematopoietic progenitor cells after transduction," *Blood*, 88:492-504, 1996.

Flamme and Risau, "Induction of vasculogenesis and hematopoiesis in vitro," *Development*, 116:435-39, 1992.

Flannery, Zolotukhin, Vaquero, LaVail, Muzyczka and Hauswirth, "Efficient photoreceptor-targeted gene expression in vivo by recombinant adeno-associated virus," *Proc. Natl. Acad. Sci. USA*, 94:6916-21, 1997.

Flotte, "Stable in vivo expression of the cystic fibrosis transmembrane conductance regulator with an adeno-associated virus vector," *Proc. Natl. Acad. Sci. USA*, 90:10613-10617, 1993.

Flotte and Carter, "Adeno-associated virus vectors for gene therapy," *Gene Ther.*, 2:357-62, 1995.

Flotte and Carter, "Adeno-associated virus vectors for gene therapy of cystic fibrosis," *Methods Enzymol.*, 292:717-32, 1998.

Flotte and Ferkol, "Genetic therapy. Past, present, and future," *Pediatr. Clin. North Am.*, 44:153-78, 1997.

Flotte, Afione and Zeitlin, "Adeno-associated virus vector gene expression occurs in nondividing cells in the absence of vector DNA integration," *Am. J. Respir. Cell Mol. Biol.*, 11:517-21, 1994.

Flotte, Afione, Conrad, McGrath, Solow, Oka, Zeitlin, Guggino and Carter, "Stable in vivo expression of the cystic fibrosis transmembrane conductance regulator with an adeno-associated virus vector," *Proc. Natl. Acad. Sci. USA*, 90:10613-17, 1993.

Flotte, Agarwal, Wang, Song, Fenjves, Inverardi, Chesnut, Afione, Loiler, Wasserfall, Kapturczak, Ellis, Nick and Atkinson, "Efficient ex vivo transduction of pancreatic islet cells with recombinant adeno-associated virus vectors," *Diabetes*, 50:515-20, 2001.

Flotte, Barraza-Ortiz, Solow, Afione, Carter and Guggino, "An improved system for packaging recombinant adeno-associated virus vectors capable of in vivo transduction," *Gene Ther.*, 2:29-37, 1995.

Flotte, Beck, Chesnut, Potter, Poirier and Zolotukhin, "A fluorescence video-endoscopy technique for detection of gene transfer and expression," *Gene Ther.*, 5:166-73, 1998.

Flotte, Carter, Conrad, Guggino, Reynolds, Rosenstein, Taylor, Walden and Wetzel, "A phase I study of an adeno-associated virus-CFTR gene vector in adult CF patients with mild lung disease," *Hum. Gene Ther.*, 7:1145-59, 1996.

Flotte, Solow, Owens, Afione, Zeitlin and Carter, "Gene expression from adeno-associated virus vectors in airway epithelial cells," *Am. J. Respir. Cell Mol. Biol.*, 7:349-56, 1992.

Forster and Symons, "Self-cleavage of plus and minus RNAs of a virusoid and a structural model for the active sites," *Cell*, 49:211-220, 1987.

Forsythe, Jiang, Iyer, Agani, Leung, Koos and Semenza, "Activation of vascular endothelial growth factor gene transcription by hypoxia-inducible factor 1," *Mol. Cell. Biol.*, 16:4604-13, 1996.

Fraley, Formari and Kaplan, "Entrapment of a bacterial plasmid in phospholipid vesicles: Potential for gene transfer," *Proc. Natl. Acad. Sci. USA*, 76:3348-52, 1979.

Frank, "On the pathogenesis of diabetic retinopathy. A 1990 update," *Ophthalmology*, 98:586-93, 1991.

Franz, Mueller, Haartong, Frey, Katus, "Transgenic animal models: new avenues in cardiovascular physiology," *J. Mol. Med.*, 75(2): 115-119, 1997.

Fredholm, Abbracchio, Burnstock, Daly, Harden, Jacobson, Leff and Williams, "Nomenclature and classification of purinoceptors," *Pharmacol. Rev.*, 46:143-56, 1994.

Fresta and Puglisi, "Application of liposomes as potential cutaneous drug delivery systems. In vitro and in vivo investigation with radioactively labeled vesicles," *J. Drug Target*, 4:95-101, 1996.

Frohman, In PCR PROTOCOLS: A GUIDE TO METHODS AND APPLICATIONS, Academic Press, New York, 1990.

Frohman, Downs, Kashio, Brinster, "Tissue distribution and molecular heterogeneity of human growth hormone-releasing factor in the transgenic mouse," *Endocrinology*, 127(5):2149-2156, 1990.

Fromm, Taylor and Walbot, "Expression of genes transferred into monocot and dicot plant cells by electroporation," *Proc. Natl. Acad. Sci. USA*, 82:5824-28, 1985.

Fry and Wood, "Gene therapy: potential applications in clinical transplantation," available only at http://www-erm-m.cbcu.com.ac.uk/99000691a.pdf, 1999.

Fry, Lea, Jackson, Newman, Ellard, Blakemore, Abu-Ghazaleh, Samuel, King and Stuart, "The structure and function of a foot-and-mouth disease virus-oligosaccharide receptor complex," *EMBO J.*, 18:543-54, 1999.

Fujita, Yui, Kusumota, Serizawa, Makino and Tochino, "Lymphocytic insulitis in a nonobese diabetic (NOD) strain of mice: an immunohistochemical and electron microscope investigation," *Biomed. Res.*, 3:429, 1982.

Fukuda, Ohyama, Lowitz, Matsuo, Pasqualini, Ruoslahti and Fukuda, "A peptide mimic of E-selectin ligand inhibits sialyl Lewis X-dependent lung colonization of tumor cells," *Cancer Res.*, 60:450-56, 2000.

Gabizon and Papahadjopoulos, "Liposomes formulations with prolonged circulation time in blood and enhanced uptake by tumors," *Proc. Natl. Acad. Sci. USA*, 85:6949-53, 1988.

Gade, Andrades, Nemni et al., *J. Vasc. Surg.*, 26:319-26, 1997.

Gallichan, Balasa, Davies and Sarvetnick, "Pancreatic IL-4 expression results in islet-reactive Th2 cells that inhibit diabetogenic lymphocytes in the nonobese diabetic mouse," *J. Immunol.*, 1163:1696-703, 1999.

Gallichan, Kafri, Krahl, Verma and Sarvetnick, "Lentivirus-mediated transduction of islet grafts with interleukin 4 results in sustained gene expression and protection from insulitis," *Hum. Gene Ther.*, 9:2717-26, 1998.

Gao and Huang, "Cytoplasmic expression of a reporter gene by co-delivery of T7 RNA polymerase and T7 promoter sequence with cationic liposomes," *Nucl. Acids Res.*, 21:2867-2872, 1993.

Gao, Alvira, Wang, Calcedo, Johnston and Wilson, "Novel adeno-associated viruses from rhesus monkeys as vectors for human gene therapy," *Proc. Natl. Acad. Sci. USA*, 99:11854-59, 2002.

Gao, Qu, Faust, Engdahl, Xiao, Hughes, Zoltick and Wilson, "High-titer adeno-associated viral vectors from a ReplCap cell line and hybrid shuttle virus," *Hum. Gene Ther.*, 9:2353-62, 1998.

Garver, Jr., Chytil, Courtney and Crystal, *Science*, 237:762-64, 1987.

Geboes, Ray, Rutgeerts, Callea, Desmet and Vantrappen, "Morphological identification of α-1-antitrypsin in the human small intestine," *Histopathology*, 6:55-60, 1982.

Gerlach et al., "Construction of a plant disease resistance gene from the satellite RNA of tobacco rinspot virus," *Nature* (London), 328:802-805, 1987.

Giannoukakis, Rundert, Robbins and Trucco, "Targeting autoimmune diabetes with gene therapy, *Diabetes*, 48:2107-21, 1999.

Gidday and Park, "Adenosine-mediated autoregulation of retinal arteriolar tone in the piglet," *Invest. Ophthalmol. Vis. Sci.*, 34:2713-19, 1993.

Gidday, Maceren, Shah, Meier and Zhu, "KATP channels mediate adenosine-induced hyperemia in retina," *Invest. Ophthalmol. Vis. Sci.*, 37:2624-33, 1996.

Gille, Swerlick and Caughman, "Transforming growth factor-alpha-induced transcriptional activation of the vascular permeability factor (VPF/VEGF) gene requires AP-2-dependent DNA binding and transactivation,"*Embo. J.*, 16:750-59, 1997.

Gilman, In CURRENT PROTOCOLS IN MOLECULAR BIOLOGY, Ausubel et al. (eds.), John Wiley & Sons, New York, pp. 4.7.1-4.7.8, 1987.

Giraud, Winocour and Berns, "Recombinant junctions formed by site-specific integration of adeno-associated virus into an episome,"*J. Virol.*, 69:6917-24, 1995.

Giraud, Winocour and Berns, "Site-specific integration by adeno-associated virus is directed by a cellular DNA sequence," *Proc. Natl. Acad. Sci. USA*, 91:10039-43, 1994.

Girod, Ried, Wobus, Lahm, Leike, Kleinschmidt, Deleage and Hallek, "Genetic capsid modifications allow efficient re-targeting of adeno-associated virus type 2," *Nat. Med.*, 5:1052-56, 1999.

Gnatenko, Arnold, Zolotukhin, Nuovo, Muzyczka and Bahou, "Characterization of recombinant adeno-associated virus-2 as a vehicle for gene delivery and expression into vascular cells," *J. Investig. Med.*, 45:87-98, 1997.

Go, Castle, Barrett, Kastelein, Dang, Mosmann, Moore and Howard, "Interleukin 10, a novel B cell stimulatory factor: unresponsiveness of X chromosome-linked immunodeficiency B cells,"*J. Exp. Med.*, 172:1625-31, 1990.

Goldstein, Ostwald and Roth, *Vision Res.*, 36:2979-74, 1996.

Gopal, "Gene transfer method for transient gene expression, stable transfection, and cotransfection of suspension cell cultures,"*Mol. Cell. Biol.*, 5:1188-90, 1985.

Goudy et al., "Elucidation of time and dose dependencies using AAV-IL-10 gene therapy for prevention of type 1 diabetes in the NOD mouse," *Mol. Ther.*, 5:S17 (Abstr. 46), 2002.

Goudy, Song, Wasserfall, Zhang, Kapturczak, Muir, Powers, Scott-Jorgensen, Campbell-Thompson, Crawford, Ellis, Flotte and Atkinson, "Adeno-associated virus vector-mediated IL-10 gene delivery prevents Type 1Type I diabetes in NOD mice," *Proc. Natl. Acad. Sci. USA*, 98:13913-18, 2001.

Graham and van der Eb, "Transformation of rat cells by DNA of human adenovirus 5," *Virology*, 4:536-39, 1973.

Graham, Smiley, Russell and Nairn, "Characteristics of a human cell line transformed by DNA from human adenovirus type 5," *J. Gen. Virol.*, 36:59-74, 1977.

Grant and King, "IGF-1 and blood vessels," *Diabetes Rev.*, 3:113-28, 1995.

Grant, Caballero and Millard, "Inhibition of IGF-I and b-FGF stimulated growth of human retinal endothelial cells by the somatostatin analogue, octreotide: a potential treatment for ocular neovascularization," *Regul. Pept.*, 48:267-78, 1993b.

Grant, Jerdan and Merimee, "Insulin-like growth factor-I modulates endothelial cell chemotaxis,"*J. Clin. Endocrinol. Metab.*, 65:370-71, 1987.

Grant, Mames, Fitzgerald, Ellis, Caballero, Chegini and Guy, "Insulin-like growth factor I as an angiogenic agent: in vivo and in vitro studies," *Ann. NY Acad. Sci.*, 692:230-42, 1993a.

Grant, Russell, Fitzgerald and Merimee, "Insulin-like growth factors in vitreous: studies in control and diabetic subjects with neovascularization,"*Diabetes*, 35:416-20, 1986.

Grant, Tarnuzzer, Caballero, Ozeck, Davis, Spoerri, Feoktistov, Biaggioni, Shryock and Belardinelli, "Adenosine receptor activation induces vascular endothelial growth factor in human retinal endothelial cells," *Circ. Res.*, 85:699-706, 1999.

Grant, Tarnuzzer, Caballero, Spoerri, Ozeck, Shryock and Belardinelli, "Adenosine mediates growth factor expression through A2B adenosine receptor (AdoR) in human retinal endothelial cells (HREC)," *Diabetes*, 47(suppl): A39, 1998.

Graser, DiLorenzo, Wang, Christianson, Chapman, Roopenian, Nathenson and Serreze, "Identification of a CD8 T cell that can independently mediate autoimmune diabetes development in the complete absence of CD4 T cell helper functions," *J. Immunol*, 164:3913-18, 2000.

Greelish, Su, Lankford, Burkman, Chen, Konig, Mercier, Desjardins, Mitchell, Zheng, Leferovich, Gao, Balice-Gordon, Wilson and Stedman, "Stable restoration of the sarcoglycan complex in dystrophic muscle perfused with histamine and a recombinant adeno-associated viral vector," *Nat. Med.*, 5:439-43, 1999.

Green and Roeder, "Transcripts of the adeno-associated virus genome: mapping of the major RNAs,"*J. Virol.*, 36:79-92, 1980.

Grifman, Trepel, Speece, Gilbert, Arap, Pasqualini and Weitzman, "Incorporation of tumor-targeting peptides into recombinant adeno-associated virus capsids," *Mol. Ther.*, 3:964-75, 2001.

Grimm, Kern, Pawlita, Ferrari, Samulski and Kleinschmidt, "Titration of AAV-2 particles via a novel capsid ELISA: packaging of genomes can limit production of recombinant AAV-2," *Gene Ther.*, 6:1322-30, 1999.

Grimm, Kern, Rittner and Kleinschmidt, "Novel tools for production and purification of recombinant adenoassociated virus vectors," *Hum. Gene Ther.*, 9:2745-60, 1998.

Grupping, Cnop, Van Schravendijk, Hannaert, Van Berkel and Pipeleers, "Low density lipoprotein binding and uptake by human and rat islet β cells," *Endocrinology*, 138:4064-68, 1997.

Guan, Guillot and Aird, "Characterization of the mouse von Willebrand factor promoter," *Blood*, 94:3405-12, 1999.

Guenette, Mooibroek, Wong and Tenniswood, "Cathepsin B, a cysteine protease implicated in metastatic progression, is also expressed during regression of the rat prostate and mammary glands," *Eur. J. Biochem.*, 226:311-21, 1994.

Guerrier-Takada, Gardiner, Marsh, pace, Altman, "The RNA moiety of ribonuclease P is the catalytic subunit of the enzyme," *Cell*, 35:849, 1983.

Guo, Chong, Shen, Foster, Sankary, McChesney, Mital, Jensik, Gebel and Williams, "In vivo effects of leflunomide on normal pancreatic islet and syngeneic islet graft function," *Transplantation*, 63:716-21, 1997.

Guy, Qi and Hauswirth, "Adeno-associated viral-mediated catalase expression suppresses optic neuritis in experimental allergic encephalomyelitis," *Proc. Nat'l Acad. Sci. USA*, 95:13847-13852, 1998.

Guy, Qi, Muzyczka and Hauswirth, "Reporter expression persists 1 year after adeno-associated virus-mediated gene transfer to the optic nerve," *Arch. Ophthalmol.*, 117:929-37, 1999.

Hahn, Laube, Lucke, Kloting, Kohnert and Warzock, "Toxic effects of cyclosporine on the endocrine pancreas of Wistar rats," *Transplantation*, 41:44-47, 1986.

Halbert, Standaert, Wilson and Miller, "Successful readministration of adeno-associated virus vectors to the mouse lung requires transient immunosuppression during the initial exposure," *J. Virol.*, 72:9795-805, 1998.

Hampel and Tritz, "RNA catalytic properties of the minimum (−)s TRSV sequence," *Biochem.*, 28:4929, 1989.

Hampel, Tritz, Hicks, Cruz, "'Hairpin' catalytic RNA model: evidence for helices and sequence requirement for substrate RNA," *Nucl. Acids Res.*, 18:299, 1990.

Handa, Muramatsu, Qiu, Mizukami and Brown, "Adeno-associated virus (AAV)-3-based vectors transduce haematopoietic cells not susceptible to transduction with AAV-2-based vectors," *J. Gen. Virol.*, 81:2077-84, 2000.

Handa, Shiroki and Shimojo, "Establishment and characterization of KB cell lines latently infected with adeno-associated virus type 1," *Virology*, 82:84-92, 1977.

Hangai, Yoshimura, Hirioi, Mandai and Honda, *Exp. Eye Res.*, 63:501-09, 1996.

Harland and Weintraub, "Translation of mammalian mRNA injected into *Xenopus oocytes* is specifically inhibited by antisense RNA," *J. Cell Biol.*, 101:1094-99, 1985.

Hashimoto, Kage, Ogita, Nakaoka, Matsuoka and Kira, "Adenosine as an endogenous mediator of hypoxia for induction of vascular endothelial growth factor mRNA in U-937 cells," *Biochem. Biophys. Res. Commun.*, 204:318-24, 1994.

Haskell and Bowen, "Efficient production of transgenic cattle by retroviral infection of early embryos," *Mol. Reprod. Dev.*, 40(3):386-390, 1995.

Haskins, Portas, Bradley, Wegmann and Lafferty, "T-lymphocyte clone specific for pancreatic islet antigen," *Diabetes*, 37:1444-48, 1988.

Hauswirth, Lewin, Zolotukhin and Muzyczka, "Production and purification of recombinant adeno-associated virus," *Methods Enzymol.*, 316:743-61, 2000.

Hauswirth, Lewin, Zolotukhin and Muzyczka, "Production and purification of recombinant AAV vectors," In: VERTEBRATE PHOTOTRANSDUCTION AND THE VISUAL CYCLE. METHODS IN ENZYMOLOGY 316, Palczewski (ed.), New York, Academic Press, in press, 2000.

Heath and Martin, "The development and application of protein-liposome conjugation techniques," *Chem. Phys. Lipids*, 40:347-58, 1986.

Heath, Lopez, Piper, Montgomery, Stern and Papahadjopoulos, "Liposome-mediated delivery of pteridine antifolates to cells: in vitro potency of methotrexate and its alpha and gamma substituents," *Biochim. Biophys. Acta*, 862:72-80, 1986.

Heilbronn, Burkle, Stephan and zur Hausen, "The adeno-associated virus rep gene suppresses herpes simplex virus-induced DNA amplification," *J. Virol.*, 64:3012-18, 1990.

Hemsley, Arnheim, Toney, Cortopassi and Galas, "A simple method for site-directed mutagenesis using the polymerase chain reaction," *Nucleic Acids Res.*, 17:6545-51, 1989.

Henry-Michelland et al., "Attachment of antibiotics to nanoparticles; Preparation, drug-release and antimicrobial activity in vitro," *Int. J. Pharm.*, 35:121-27, 1987.

Hering, Browatzki, Schultz, Bretzel and Federlin, "Clinical islet transplantation—registry report, accomplishments in the past and future research needs," *Cell Transplant.*, 2:269-82, discussion 283-305, 1993.

Hermens, ter Brake, Dijkhuizen, Sonnemans, Grimm, Kleinschmidt and Verhaagen, "Purification of recombinant adeno-associated virus by iodixanol gradient ultracentrifugation allows rapid and reproducible preparation of vector stocks for gene transfer in the nervous system," *Hum. Gene Ther.*, 10:1885-91, 1999.

Hermonat and Muzyczka, "Use of adeno-associated virus as a mammalian DNA cloning vector: transduction of neomycin resistance into mammalian tissue culture cells," *Proc. Natl. Acad. Sci. USA*, 81:6466-70, 1984.

Hermonat, Labow, Wright, Berns and Muzyczka, "Genetics of adeno-associated virus: isolation and preliminary characterization of adeno-associated virus type 2 mutants," *J. Virol.*, 51:329-39, 1984.

Hernandez, Wang, Kearns, Loiler, Poirier and Flotte, "Latent adeno-associated virus infection elicits humoral but not cell-mediated immune responses in a nonhuman primate model," *J. Virol.*, 73:8549-58, 1999.

Hertel, Herschlag and Uhlenbeck, "A kinetic and thermodynamic framework for the hammerhead ribozyme reaction," *Biochemistry*, 33:3374-3385, 1994.

Herzog, Hagstrom, Kung, Tai, Wilson, Fisher and High, "Stable gene transfer and expression of human blood coagulation factor IX after intramuscular injection of recombinant adeno-associated virus," *Proc. Natl. Acad. Sci. USA*, 94:5804-09, 1997.

Hey, Twells, Philips, Nakagawa, Brown et al., "Cloning of a novel member of the low-density lipoprotein receptor family," *Gene*, 216:103-11, 1998.

Hileman, Fromm, Weiler and Linhardt, "Glycosaminoglycan-protein interactions: definition of consensus sites in glycosaminoglycan binding proteins," *Bioessays*, 20:156-67, 1998.

Hirano, Fujihira, Ohara, Katsuki and Noguchi, "Morphological and functional changes of islets of Langerhans in FK506-treated rats," *Transplantation*, 53:889-94, 1992.

Hirano, Yamashita, Nakagawa, Ohya, Matsuura, Tsukamoto, Okamoto, Matsuyama, Matsumoto, Miyagawa and Matsuzawa, "Expression of human scavenger receptor class B type I in cultured human monocyte-derived macrophages and atherosclerotic lesions," *Circ. Res.*, 85:108-16, 1999.

Hirt, "Selective extraction of polyoma DNA from infected mouse cell cultures," *J. Mol. Biol.*, 26:365-69, 1967.

Hoggan, *Fed. Proc.*, 24:248, 1965.

Hoggan Thomas, Thomas and Johnson, In PROCEEDING OF THE FOURTH LEPETIT COLLOQUIUM, Cacoyac, Mexico, North Holland, Amsterdam, pp. 243-249, 1972.

Hoggan, Blacklow and Rowe, "Studies of small DNA viruses found in various adenovirus preparations: physical, biological, and immunological characteristics," *Proc. Natl. Acad. Sci. USA*, 55:1467-74, 1966.

Hoggan, Shatkin, Blacklow, Koczot and Rose, "Helper-dependent infectious deoxyribonucleic acid from adenovirus-associated virus," *J. Virol.,* 2:850-51, 1968.

Holzknecht and Platt, "The fine cytokine line between graft acceptance and rejection," *Nat. Med.,* 6:497-98, 2000.

Hoover et al., Eds., In: *Remington's Pharmaceutical Sciences,* 16th Edition, Mack Publishing Co., Easton, Pa., 1980.

Hogue, Ishizu, Matsumoto, Han, Arisaka, Takayama, Suzuki, Kato, Kanda, Watanabe and Handa, "Nuclear transport of the major capsid protein is essential for adeno-associated virus capsid formation,"*J. Virol.,* 73:7912-15, 1999.

Hsu, de Waal Malefyt, Fiorentino, Dang, Vieira, de Vries, Spits, Mosmann and Moore, "Expression of interleukin-10 activity by Epstein-Barr virus protein BCRF 1," *Science,* 250:830-32, 1990.

Huang and Hearing, "Adenovirus early region 4 encodes two gene products with redundant effects in lytic infection.,"*J. Virol.,* 63:2605-15, 1989.

Hussain, Strickland and Bakillah, "The Mammalian Low-Density Lipoprotein Receptor Family,"*Annu. Rev. Nutr.,* 19:141-72, 1999.

Hwang, Park, Park, "Gastric retentive drug-delivery systems," *Crit. Rev. Ther. Drug Carrier Syst.,* 15(3):243-284, 1998.

Hyer, Sharp, Brooks, Burrin and Kohner, "A two-year follow-up study of serum insulin-like growth factor-I in diabetics with retinopathy,"*Metabolism,* 38:586-89, 1989.

Im and Muzyczka, "The AAV origin binding protein Rep68 is an ATP-dependent site-specific endonuclease with DNA helicase activity," *Cell,* 61:447-57, 1990.

Imaizumi, Woolworth, Fishman and Chan, "Liposome-entrapped superoxide dismutase reduces cerebral infarction in cerebral ischemia in rats," *Stroke,* 21:1312-17, 1990a.

Imaizumi, Woolworth, Kinouchi, Chen, Fishman and Chan, "Liposome-entrapped superoxide dismutase ameliorates infarct volume in focal cerebral ischemia," *Acta. Neurochir. Suppl.,* 51:236-238, 1990b.

Inoue and Russell, "Packaging cells based on inducible gene amplification for the production of adeno-associated virus vectors," *J. Virol.,* 72:7024-31, 1998.

Ishii, Kim, Fujita, Endo, Saeki and Yamamoto, "cDNA cloning of a new low-density lipoprotein receptor-related protein and mapping of its gene (LRP3) to chromosome bands 19q12-q13.2," *Genomics,* 51:132-35, 1998.

Jacobsen, Madsen, Moestrup, Lund, Tommerup et al., "Molecular characterization of a novel human hybrid-type receptor that binds the alpha2-macroglobulin receptor-associated protein," *J. Biol. Chem.,* 271:31379-83, 1996.

Jacobson, Cideciyan, Huang, Hanna, Freund, Affatigato, Carr, Zack, Stone and McInnes, "Retinal degenerations with truncation mutations in the cone-rod homeobox (CRX) gene," *Invest. Ophthalmol. Vis. Sci.,* 39:2417-2426, 1998.

Jaeger, Turner and Zuker, "Improved predictions of secondary structures for RNA," *Proc. Natl. Acad. Sci. USA,* 86:7706-10, 1989.

Jager, Zhao and Porter, "Endothelial cell-specific transcriptional targeting from a hybrid long terminal repeat retrovirus vector containing human prepro-endothelin-1 promoter sequences," *J. Virol.,* 73:9702-09, 1999.

Jaggar, Chan, Harris and Bicknell, "Endothelial cell-specific expression of tumor necrosis factor-α from the KDR or E-selectin promoters following retroviral delivery," *Hum. Gene Ther.,* 8:2239-47, 1997.

Janciauskiene, "Conformational properties of serine proteinase inhibitors (serpins) confer multiple pathophysiological roles,"*Biochim. Biophys. Acta,* 1535:221-35, 2001.

Jindal, "Post-transplant diabetes mellitus—a review," *Transplantation,* 58:1289-98, 1994.

Johansson et al., "Alpha-1-antitrypsin is present in the specific granules of human eosinophilic granulocytes," *Clin. Exp. Allergy,* 31:379-86, 2001.

Johnson and Curtis, "Preventive therapy for periodontal diseases,"*Adv. Dent. Res.,* 8:337-48, 1994.

Johnson et al., "Cytotoxicity of a replication-defective mutant of herpes simplex virus type 1," *J. Virol.,* 66:2952-65, 1992a.

Johnson et al., "Efficiency of gene transfer for restoration of normal airway epithelial function in cystic fibrosis," *Nat. Genet.,* 2:21-25, 1992b.

Johnson et al., "Improved cell survival by the reduction of immediate-early gene expression in the replication-defective mutants of herpes simplex virus type 1 but not by mutation of the virion host shutoff function," *J. Virol.,* 68:6347-62, 1994.

Johnston et al., "HSV/AAV hybrid amplicon vectors extend transgene expression in human glioma cells," *Hum. Gene Ther.,* 8:359-70, 1997.

Jones, Zou, Cowan and Kjeldgaard, "Improved methods for binding protein models in electron density maps and the location of errors in these models," *Acta. Crystallograph. A,* 47:110-19, 1991.

Jooss, Yang, Fisher and Wilson, "Transduction of dendritic cells by DNA viral vectors directs the immune response to transgene products in muscle fibers," *J. Virol.,* 727:4212-23, 1998.

Joslin et al., "The SEC receptor recognizes a pentapeptide neodomain of alpha 1-antitrypsin-protease complexes,"*J. Biol. Chem.,* 266:11282-88, 1991.

Joyce, "RNA evolution and the origins of life," *Nature,* 338:217-244, 1989.

Kaludov, Brown, Walters, Zabner and Chiorini, "Adeno-associated virus serotype 4 (AAV4) and AAV5 both require sialic acid binding for hemagglutination and efficient transduction but differ in sialic acid linkage specificity,"*J. Virol.,* 75:6884-93, 2001.

Kang, et al., "Up-regulation of luciferase gene expression with antisense oligonucleotides: implications and applications in functional assay development," *Biochemistry,* 37(18):6235-9, 1998.

Kaplitt, Leone, Samulski, Xiao, Pfaff, O'Malley and During, "Long-term gene expression and phenotypic correction using adeno-associated virus vectors in the mammalian brain," *Nat. Genet.,* 8:148-54, 1994.

Kapturczak, Flotte and Atkinson, *Curr. Mol. Med.,* 1:245-58, 2001.

Kashani-Sabet et al., "Reversal of the malignant phenotype by an anti-ras ribozyme," *Antisense Res. Dev.,* 2:3-15, 1992.

Kaufman, Platt Rabe, Dunn, Bach and Sutherland, "Differential roles of Mac-1+ cells, and CD4+ and CD8+ T lymphocytes in primary nonfunction and classic rejection of islet allografts,"*J. Exp. Med.,* 172:291-302, 1990.

Kay, Manno, Ragni, et al., "Evidence for gene transfer and expression of factor IX in haemophilia B patients treated with an AAV vector," *Nat. Genet.,* 24:257-261, 2000.

Kearns, Afione, Fulmer, Pang, Erikson, Egan, Landrum, Flotte and Cutting, "Recombinant adeno-associated virus (AAV-CFTR) vectors do not integrate in a site-specific fashion in an immortalized epithelial cell line," *Gene Ther.,* 3:748-55, 1996.

Kenyon, Alejandro, Mintz and Ricordi, "Islet cell transplantation: beyond the paradigms," *Diabetes Metab. Rev.*, 12:361-72, 1996.

Kenyon, Ranuncoli, Masetti, Chatzipetrou and Ricordi, "Islet transplantation: present and future perspectives," *Diabetes Metab. Rev.*, 14:303-13, 1998.

Keppler, Markert, Carnal, Berdoz, Bamat and Sordat, "Human colon carcinoma cells synthesize and secrete α1-proteinase inhibitor," *Biol. Chem. Hoppe-Seyler*, 377:301-11, 1996.

Kessler, Podsakoff, Chen, McQuiston, Colosi, Matelis, Kurtzman and Byrne, "Gene delivery to skeletal muscle results in sustained expression and systemic delivery of a therapeutic protein," *Proc. Natl. Acad. Sci. USA*, 93:14082-87, 1996.

Khleif et al., "Inhibition of cellular transformation by the adeno-associated virus rep gene," *Virology*, 181:738-41, 1991.

Kief and Warner, "Coordinate control of syntheses of ribosomal ribonucleic acid and ribosomal proteins during nutritional shift-up in *Saccharomyces cerevisiae*," *Mol. Cell Biol.*, 1:1007-1015, 1981.

Kim and Cech, "Three-dimensional model of the active site of the self-splicing rRNA precursor of Tetrahymena," *Proc. Natl. Acad. Sci. USA* 84:8788-8792, 1987.

Kimura, Weisz, Kurashima, Hashimoto, Ogura, D'Acquisto, Addeo, Makuuchi and Esumi, "Hypoxia response element of the human vascular endothelial growth factor gene mediates transcriptional regulation by nitric oxide: control of hypoxia-inducible factor-1 activity by nitric oxide," *Blood*, 95:189-97, 2000.

King, Dubielzig, Grimm and Kleinschmidt, "DNA helicase-mediated packaging of adeno-associated virus type 2 genomes into preformed capsids," *EMBO J.*, 20:3282-91, 2001.

King, Goodman, Buzney, Moses and Kahn, "Receptors and growth-promoting effects of insulin and insulin-like growth factors on cells from bovine retinal capillaries and aorta," *J. Clin. Invest.*, 75:1028-36, 1985.

Klein, Meyer, Peel, Zolotukhin, Meyers, Muzyczka and King, "Neuron-specific transduction in the rat septohippocampal or nigrostriatal pathway by recombinant adeno-associated virus vectors,"*Exper. Neurol.* 150:183-94, 1998.

Klein, Wolf, Wu, Sanford, "High-velocity microprojectiles for delivering nucleic acids into living cells. 1987," *Biotechnology*, 24:384-386, 1992.

Knipe, "The role of viral and cellular nuclear proteins in herpes simplex virus replication," *Adv. Virus Res.*, 37:85-123, 1989.

Knipe et al., "Characterization of two conformational forms of the major DNA-binding protein encoded by herpes simplex virus 1,"*J. Virol.*, 44:736-41, 1982.

Knoell, Ralston, Coulter and Wewers, "Alpha 1-antitrypsin and protease complexation is induced by lipopolysaccharide, interleukin-1β, and tumor necrosis factor-alpha in monocytes,"*Am. J. Respir. Crit. Care Med.*, 157:246-55, 1998.

Koeberl, Alexander, Halbert, et al., "Persistent expression of human clotting factor IX from mouse liver after intravenous injection of adeno-associated virus vectors," *Proc. Nat'l Acad. Sci. USA*, 94:1426-1431, 1997.

Kohner and Oakley, "Diabetic retinopathy," *Metabolism*, 24:1085-102, 1975.

Koizumi, Kamiya and Ohtsuka, *Gene*, 117:179-84, 1992.

Kolaczynski and Caro, "Insulin-like growth factor-1 therapy in diabetes: physiologic basis, clinical benefits, and risks, "*Ann. Intern. Med.*, 120:47-55, 1994.

Korhonen, Lahtinen, Halmekyto, Alhonen, Janne, Dumont and Alitalo, "Endothelial-specific gene expression directed by the tie gene promoter in vivo," *Blood*, 86:1828-35, 1995.

Kotin, "Prospects for the use of adeno-associated virus as a vector for human gene therapy," *Hum. Gene Ther.*, 5:793-801, 1994.

Kotin and Berns, "Organization of adeno-associated virus DNA in latently infected Detroit 6 cells," *Virology*, 170:460-67, 1989.

Kotin, Linden and Berns, "Characterization of a preferred site on human chromosome 19q for integration of adeno-associated virus DNA by non-homologous recombination," *EMBO Journal*, 11:5071-78, 1992.

Kotin, Menninger, Ward and Berns, "Mapping and direct visualization of a region-specific viral DNA integration site on chromosome 19q13-qter," *Genomics*, 10:831-34, 1991.

Kotin, Siniscalco, Samulski, Zhu, Hunter, Laughlin, McLaughlin, Muzyczka, Rocchi and Berns, "Site-specific integration by adeno-associated virus," *Proc. Natl. Acad. Sci. USA*, 87:2211-15, 1990.

Kraulis, "MOLSCRIPT: a program to produce both detailed and schematic plots of protein structures,"*J. Appl. Cryst.*, 24:946-50, 1991.

Kroemer, Hirsch, Gonzalez-Garcia and Martinez, "Differential involvement of Th1 and Th2 cytokines in autoimmune diseases," *Autoimmunity*, 24:25-33, 1996.

Kronenberg, Kleinschmidt and Bottcher, "Electron cryo-microscopy and image reconstruction of adeno-associated virus type 2 empty capsids," *EMBO Rep.*, 2:997-1002, 2001.

Kuby, In IMMUNOLOGY, 2nd Edition. W.H. Freeman & Company, New York, 1994.

Kvietikova, Wenger, Marti and Gassmann, "The transcription factors ATF-1 and CREB-1 bind constitutively to the hypoxia-inducible factor-1 (HIF-1) DNA recognition site," *Nucleic Acids Res.*, 23:4542-50, 1995.

Kwoh, Davis, Whitfield, Chappelle, DiMichele, Gingeras, "Transcription-based amplification system and detection of amplified human immunodeficiency virus type 1 with a bead-based sandwich hybridization format," *Proc. Natl. Acad. Sci. USA*, 86(4):1173-1177, 1989.

Kyte and Doolittle, "A simple method for displaying the hydropathic character of a protein," *J. Mol. Biol.*, 157:105-32, 1982.

L'Huillier, David, Bellamy, "Cytoplasmic delivery of ribozymes leads to efficient reduction in alpha-lactalbumin mRNA levels in C1271 mouse cells," *EMBO J.*, 11(12):4411-4418, 1992.

LaFace and Peck, "Reciprocal allogeneic bone marrow transplantation between NOD mice and diabetes-nonsusceptible mice associated with transfer and prevention of autoimmune diabetes," *Diabetes*, 38:894-901, 1989.

Lam and Tso, *Res. Commun. Mol. Pathol. Pharmacol.*, 92:329-40, 1996.

Langford and Miell, "The insulin-like growth factor-I binding protein axis: physiology, pathophysiology and therapeutic manipulation," *Eur. J. Clin. Invest.*, 23:503-16, 1993.

Lasic, "Novel applications of liposomes," *Trends Biotechnol.*, 16:307-21, 1998.

Laughlin et al., "Defective-interfering particles of the human parvovirus adeno-associated virus," *Virology*, 94:162-74, 1979.

Laughlin, Tratschin, Coon and Carter, "Cloning of infectious adeno-associated virus genomes in bacterial plasmids," *Gene*, 23:65-73, 1983.

Lem, Applebury, Falk, Flannery and Simon, *J. Biol. Chem.*, 266:9667-72, 1991.

Lem, Flannery, Li, et al., "Retinal degeneration is rescued in transgenic rd mice by expression of the cGMP phosphodiesterase beta subunit," *Proc. Nat'l Acad. Sci. USA*, 89:4422-4426, 1992.

Lewin, Drenser, Hauswirth, Nishikawa, Yasumura, Flannery and LaVail, "Ribozyme rescue of photoreceptor cells in a transgenic rat model of autosomal dominant retinitis pigmentosa," *Nat. Med.*, 4:967-971, 1998.

Li, Eastman, Schwartz and Draghia-Akli, *Nat. Biotechnol.*, 17:241-45, 1999.

Li, Samulski and Xiao, "Role for highly regulated rep gene expression in adeno-associated virus vector production,"*J. Virol.*, 71:5236-43, 1997.

Liblau, Singer and McDevitt, "Th1 and Th2CD4+ T-cells in the pathogenesis of organ specific autoimmune diseases," *Immunology Today*, 16:34-38, 1995.

Lieber, Sandig, Sommer, Bahring, Strauss, "Stable high-level gene expression in mammalian cells by T7 phage RNA polymerase,"*Methods Enzymol.*, 217:47-66, 1993.

Like and Rossini, "Streptozotocin-induced pancreatic insulitis: new model of diabetes mellitus," *Science*, 193:415-17, 1976.

Like, Biron, Weringer, Byman, Sroczynski and Guberski, "Prevention of diabetes in BioBreeding/Worcester rats with monoclonal antibodies that recognize T lymphocytes or natural killer cells,"*J. Exp. Med.*, 164:1145-59, 1986.

Limb, Chignell, Green, LeRoy and Dumonde, "Distribution of TNF alpha and its reactive vascular adhesion molecules in fibrovascular membranes of proliferative diabetic retinopathy," *Br. J. Ophthalmol.*, 80:168-73, 1996.

Linden and Woo, "AAVant-garde gene therapy," *Nat. Med.*, 5:21-22, 1999.

Linden, Ward, Giraud, Winocour and Berns, "Site-specific integration by adeno-associated virus," *Proc. Natl. Acad. Sci. USA*, 93:11288-94, 1996.

Linetsky, Bottino, Lehmann, Alejandro, Inverardi and Ricordi, "Improved human islet isolation using a new enzyme blend, liberase," *Diabetes*, 46:1120-23, 1997.

Linetsky, Inverardi, Kenyon, Alejandro and Ricordi, "Endotoxin contamination of reagents used during isolation and purification of human pancreatic islets," *Transplant Proc.*, 30:345-46, 1998.

Liptak et al., "Functional order of assembly of herpes simplex virus DNA replication proteins into prereplicative site structures," *J. Virol.*, 70:1759-67, 1996.

Lisziewicz et al., "Inhibition of human immunodeficiency virus type 1 replication by regulated expression of a polymeric Tat activation response RNA decoy as a strategy for gene therapy in AIDS," *Proc. Natl. Acad. Sci. USA*, 90:8000-8004, 1993.

Little and Lee, *J. Biol. Chem.*, 270:9526-34, 1995. Liu and Thorp, "Cell surface heparan sulfate and its roles in assisting viral infections,"*Med. Res. Rev.*, 22:1-25, 2002.

Loeb, Cordier, Harris, Weitzman and Hope, "Enhanced expression of transgenes from adeno-associated virus vectors with the woodchuck hepatitis virus posttranscriptional regulatory element: implications for gene therapy," *Hum. Gene Ther.*, 10:2295-305, 1999.

Lopez-Berestein et al., "Liposomal amphotericin B for the treatment of systemic fungal infections in patients with cancer: a preliminary study," *J. Infect. Dis.*, 2151:704, 1985a.

Lopez-Berestein et al., "Protective effect of liposomal-amphotericin B against *C. albicans* infection in mice," *Cancer Drug Delivery*, 2:183, 1985b.

Lu, Xiao, Clapp, Li, Broxmeyer, "High efficiency retroviral mediated gene transducion into single isolated immature and replatable CD34(3+) hematopoietic stem/progenitor cells from human umbilical cord blood,"*J. Exp. Med.*, 178 (6):2089-2096, 1993.

Lukonis and Weller, "Characterization of nuclear structures in cells infected with herpes simplex virus type 1 in the absence of viral DNA replication," *J. Virol.*, 70:1751-58, 1996.

Luo, Paranya and Bischoff, "Noninflammatory expression of E-selectin is regulated by cell growth," *Blood*, 93:3785-91, 1999.

Lusby and Berns, "Mapping of the 5' termini of two adeno-associated virus 2 RNAs in the left half of the genome," *J. Virol.*, 41:518-26, 1982.

Lusby, Fife and Berns, "Nucleotide sequence of the inverted terminal repetition in adeno-associated virus DNA, "*J. Virol.*, 34:402-09, 1980.

Lutty, Mathews, Merges and McLeod, "Adenosine stimulates canine retinal microvascular endothelial cell migration and tube formation," *Curr. Eye Res.*, 17:594-607, 1998.

Lutty, Merges and McLeod, "5' nucleotidase and adenosine during retinal vasculogenesis and oxygen-induced retinopathy," *Invest. Ophthalmol. Vis. Sci.*, 41:218-29, 2000.

Lynch, Hara, Leonard, Williams, Dean and Geary, "Adeno-associated virus vectors for vascular gene delivery," *Circ. Res.*, 80:497-505, 1997.

Macen, Upton, Nation and McFadden, "SERP1, a serine proteinase inhibitor encoded by myxoma virus, is a secreted glycoprotein that interferes with inflammation," *Virology*, 195:348-63, 1993.

MacNeil, Suda, Moore, Mosmann and Zlotnik, "IL-10, a novel growth cofactor for mature and immature T cells,"*J. Immunol.*, 145:4167-73, 1990.

Maloy et al., In MICROBIAL GENETICS, 2nd Edition, Jones and Barlett Publishers, Boston, Mass., 1994.

Mandel, Spratt, Snyder and Leff, "Midbrain injection of recombinant adeno-associated virus encoding rat glial cell line-derived neurotrophic factor protects nigral neurons in a progressive 6-hydroxydopamine-induced degeneration model of Parkinson's disease in rats," *Proc. Natl. Acad. Sci. USA*, 94:14083-88, 1997.

Maniatis et al., "Molecular Cloning: a Laboratory Manual," Cold Spring Harbor Laboratory, Cold Spring Harbor, N.Y., 1982.

Marcus et al., "Adeno-associated virus RNA transcription in vivo," *Eur. J. Biochem.*, 121:147-54, 1981.

Margalit, "Liposome-mediated drug targeting in topical and regional therapies," *Crit. Rev. Ther. Drug Carrier Syst.*, 12(2-3):233-261, 1995.

Massetti, Inverardi, Ranuncoli, Iaria, Lupo, Vizzardelli, Kenyon, Alejandro and Ricordi, "Current indications and limits of pancreatic islet transplantation in diabetic nephropathy," *J. Nephrol.*, 10:245-2521, 1997.

Mathiowitz, Jacob, Jong, Carino, Chickering, Chaturvedi, Santos, Vijayaraghavan, Montgomery, Bassett, Morrell, "Biologically erodable microspheres as potential oral drug delivery systems," *Nature*, 386(6623):410-414, 1997.

Matsushita et al., "Adeno-associated virus vectors can be efficiently produced without helper virus," *Gene Ther.*, 5:938-45, 1998.

McAuthor and Raulet, "CD28-induced costimulation of T helper type 2 cells mediated by induction of responsiveness to interleukin 4,"*J. Exp. Med.*, 178:1645, 1993.

McCarthy et al., "Herpes simplex virus type 1 ICP27 deletion mutants exhibit altered patterns of transcription and are DNA deficient," *J. Virol.*, 63:18-27, 1989.

McCarty, Christensen and Muzyczka, "Sequences required for coordinate induction of adeno-associated virus p19 and p40 promoters by Rep protein," J. Virol., 65:2936-45, 1991.

McCown, Xiao, Li, Breese and Samulski, "Differential and persistent expression patterns of CNS gene transfer by an adeno-associated virus (AAV) vector," *Brain Res.*, 713:99-107, 1996.

McKenna, Olson, Chipman, Baker, Booth, Christensen, Aasted, Fox, Bloom, Wolfinburger and Agbandje-McKenna, "Three-dimensional structure of Aleutian mink disease parvovirus: implications for disease pathogenicity," *J. Virol.*, 73:6882-91, 1999.

McLauchlan et al., "Herpes simplex virus IE63 acts at the posttranscriptional level to stimulate viral mRNA 3' processing," *J. Virol.*, 66:6939-45, 1992.

McLaughlin, Collis, Hermonat and Muzyczka, *J. Virol.*, 62:1963-73, 1988.

Merimee, Zapf and Froesch, "Insulin-like growth factors: studies in diabetics with and without retinopathy," *N. Engl. J. Med.*, 309:527-30, 1983.

Merritt and Bacon, "Raster3D Photorealistic Molecular Graphics," p. 505-24, METHODS IN ENZYMOLOGY, Vol. 277, 1997.

Meyer-Schwickerath, Pfeiffer, Blum, Freyberger, Klein, Losche, Rollmann and Schatz, "Vitreous levels of the insulin-like growth factors I and II, and the insulin-like growth factor binding proteins 2 and 3, increase in neovascular eye disease. Studies in nondiabetic and diabetic subjects," *J. Clin. Invest.*, 92:2620-25, 1993.

Miao, Snyder, Schowalter, Patijn, Donahue, Winther and Kay, "The kinetics of rAAV integration in the liver [letter]," *Nat. Genet.*, 19:13-15, 1998.

Michel and Westhof, "Modeling of the three-dimensional architecture of group I catalytic introns based on comparative sequence analysis," *J. Mol. Biol.*, 216:585-610, 1990.

Mietus-Snyder, Glass and Pitas, "Transcriptional activation of scavenger receptor expression in human smooth muscle cells requires AP-1/c-Jun and C/EBPβ: both AP-1 binding and JNK activation are induced by phorbol esters and oxidative stress," *Arterioscler. Thromb. Vasc. Biol.*, 18:1440-49, 1998.

Miller, Appel, O'Neil and Wicker, "Both the Lyt-2+ and L3T4+T cell subsets are required for the transfer of diabetes in nonobese diabetic mice," *J. Immunol.*, 140:52-58, 1988.

Minet, Arnould, Michel, Roland, Mottet, Raes, Remade and Michiels, "ERK activation upon hypoxia: involvement in HIF-1 activation," *FEBS Lett.*, 468:53-58, 2000.

Mishra and Rose, "Adeno-associated virus DNA replication is induced by genes that are essential for HSV-1 DNA synthesis," *Virology*, 179:632-39, 1990.

Mitchell and Tjian, *Science*, 245:371-78, 1989.

Miyamoto, Akaike, Alam, Inoue, Hamamoto, Ikebe, Yoshitake, Okamoto and Maeda, "Novel functions of human α(1)-protease inhibitor after S-nitrosylation: inhibition of cysteine protease and antibacterial activity," *Biochem. Biophys. Res. Commun.*, 267:918-23, 2000.

Mizutani, Kern and Lorenzi, "Accelerated death of retinal microvascular cells in human and experimental diabetic retinopathy," *J. Clin. Invest.*, 97:2883-90, 1996.

Monahan, Samulski, Tazelaar, et al., "Direct intramuscular injection with recombinant AAV vectors results in sustained expression in a dog model of hemophilia," *Gene Ther.*, 5:40-49, 1998.

Moore, Vieira, Fiorentino, Trounstine, Khan and Mosmann, "Homology of cytokine synthesis inhibitory factor (IL-10) to the Epstein-Barr virus gene BCRFI," *Science*, 248:1230-34, 1990.

Mori and Fukatsu, "Anticonvulsant effect of DN-1417a derivative of thyrotropin-releasing hormone and liposome-entrapped DN-1417 on amygdaloid-kindled rats," *Epilepsia*, 33:994-1000, 1992.

Moritani, Yoshimoto, Tashiro, Hashimoto, Miyazaki, Li, Kudo, Iwahana, Hayashi, Sano et al., "Transgenic expression of IL-10 in pancreatic islet A cells accelerates autoimmune insulitis and diabetes in non-obese diabetic mice," *Int. Immunol.*, 6:1927-36, 1994.

Monis, *Learn. Motiv.*, 12:239-260, 1981.

Morris et al., *Eur. J. Neurosci.*, 2:1016, 1990.

Morwald, Yamazaki, Bujo, Kusunoki, Kanaki et al., "A novel mosaic protein containing LDL receptor elements is highly conserved in humans and chickens," *Arterioscler. Thromb. Vasc. Biol.*, 17:996-1002 (1997).

Moskalenko, Chen, van Roey, Donahue, Snyder, McArthur and Patel, "Epitope mapping of human anti-adeno-associated virus type 2 neutralizing antibodies: implications for gene therapy and virus structure," *J. Virol.*, 74:1761-66, 2000.

Mueller, Krahl and Sarvetnick, "Pancreatic expression of interleukin-4 abrogates insulitis and autoimmune diabetes I nonobese diabetic (NOD) mice," *J. Exp. Med.*, 184:1093-99, 1996.

Mukai, Munekata and Higashijima, "G protein antagonists. A novel hydrophobic peptide competes with receptor for G protein binding," *J. Biol. Chem.*, 267:16237-43, 1992.

Muller et al., "Efficient transfection and expression of heterologous genes in PC12 cells," *Cell Biol.*, 9:221-29, 1990.

Mulloy and Linhardt, "Order out of complexity—protein structures that interact with heparin," *Curr. Opin. Struct. Biol.*, 11:623-28, 2001.

Muralidhar, Becerra and Rose, "Site-directed mutagenesis of adeno-associated virus type 2 structural protein initiation codons: effects on regulation of synthesis and biological activity," *J. Virol.*, 68:170-76, 1994.

Murphy, Zhou, Giese, Williams, Escobedo and Dwarki, "Long-term correction of obesity and diabetes in genetically obese mice by a single intramuscular injection of recombinant adeno-associated virus encoding mouse leptin," *Proc. Natl. Acad. Sci. USA*, 94:13921-26, 1997.

Muzyczka and Berns, "Parvoviridae: The viruses and their replication," p. 2327-2360, In FIELDS VIROLOGY, Fourth ed., P. M. Howley (ed.), Lippincott Williams and Wilkins, New York, 2001.

Muzyczka and McLaughlin, "Use of adeno-associated virus as a mamalian transduction vector," In CURRENT COMMUNICATIONS IN MOLECULAR BIOLOGY: VIRAL VECTORS, Glzman and Hughes (eds.), Cold Spring Harbor Laboratory Press, Cold Spring Harbor, N.Y., pp. 39-44, 1988.

Muzyczka, "Use of adeno-associated virus as a general transduction vector for mammalian cells," *Curr. Top Microbiol. Immunol.*, 158:97-129, 1992.

Muzyczka, Samulski, Hermonat, Srivastava and Berns, "The genetics of adeno-associated virus," *Adv. Exp. Med. Biol.*, 179:151-61, 1984.

Nakai, Herzog, Hagstrom, et al., "Adeno-associated viral vector-mediated gene transfer of human blood coagulation factor IX into mouse liver," *Blood*, 91:4600-4607, 1998.

Nakai, Iwaki, Kay and Couto, "Isolation of recombinant adeno-associated virus vector-cellular DNA junctions from mouse liver," *J. Virol.*, 73:5438-5447, 1999.

Nathans, Thomas and Hogness, "Molecular genetics of human color vision: the genes encoding blue, green, and red pigments," *Science,* 232:193-202, 1986.

Nees, Herzog, Becker, Bock, Des Rosiers and Gerlach, "The coronary endothelium: a highly active metabolic barrier for adenosine," *Basic Res. Cardiol.,* 80:515-29, 1985.

Nettelbeck, Jerome and Muller, "A strategy for enhancing the transcriptional activity of weak cell type-specific promoters," *Gene Ther.,* 5:1656-64, 1998.

Nettelbeck, Jr. and Muller, "A dual specificity promoter system combining cell cycle-regulated and tissue-specific transcriptional control," *Gene Ther.,* 6:1276-81, 1999.

Ni, Zhou, McCarty, Zolotukhin and Muzyczka, "In vitro replication of adeno-associated virus DNA,"*J. Virol.,* 68:1128-38, 1994.

Nicholls, Sharp and Honig, "PROTEINS, Structure, Function and Genetics," 11:281, 1991.

Nickerson, Steurer, Steiger, Zheng, Steele and Strom, "Cytokines and the Th1/Th2 paradigm in transplantation," *Curr. Opin. Immunol.,* 6:757-64, 1994.

Nicklin, Buening, Dishart, de Alwis, Girod, Hacker, Thrasher, Ali, Hallek and Baker, "Efficient and selective AAV2-mediated gene transfer directed to human vascular endothelial cells,"*Mol. Ther.,* 4:174-81, 2001.

Nicolau and Gersonde, "Incorporation of inositol hexaphosphate into intact red blood cells, I. fusion of effector-containing lipid vesicles with erythrocytes," *Naturwissenschaften* (Germany), 66:563-66, 1979.

Nicolau and Sene, "Liposome-mediated DNA transfer in eukaryotic cells," *Biochem. Biophys. Acta,* 721:185-90, 1982.

Niemann, Baggott and Miller, "Binding of SPAAT, the 44-residue C-terminal peptide of alpha 1-antitrypsin, to proteins of the extracellular matrix," *J. Cell Biochem.,* 66:346-57, 1997.

Nitta, Tashiro, Tokui, Shimada, Takei, Tabayashi and Miyazaki, "Systemic delivery of interleukin 10 by intramuscular injection of expression plasmid DNA prevents autoimmune diabetes in nonobese diabetic mice," *Hum. Gene Ther.,* 9:1701-07, 1998.

Nussler, Carroll, Di Silvio, Rilo, Simmons, Starzl and Ricordi, "Hepatic nitric oxide generation as a putative mechanism for failure of intrahepatic islet cell grafts," *Transplant Proc.,* 24:2997, 1992.

O'Blenes, Zaidi, Cheah, McIntyre, Kaneda and Rabinovitch, "Gene transfer of the serine elastase inhibitor elafin protects against vein graft degeneration," *Circulation,* 102: III289-95, 2000.

Ohara, Dort, Gilbert, "One-sided polymerase chain reaction: the amplification of cDNA," *Proc. Natl. Acad. Sci. USA,* 86(15):5673-5677, 1989.

Ohkawa, Yuyama, Taira, "Activities of HIV-RNA targeted ribozymes transcribed from a 'shot-gun' type ribozyme-trimming plasmid," *Nucl. Acids Symp. Ser.,* 27:15-16, 1992.

Ojwang, Hampel, Looney, Wong-Staal, Rappaport, "Inhibition of human immunodeficiency virus type 1 expression by a hairpin ribozyme," *Proc. Natl. Acad. Sci. USA,* 89(22): 10802-10806, 1992.

Oldstone, "Prevention of Type I diabetes in Nonobese Diabetic Mice by Virus Infection," *Science,* 23:500, 1988.

Olsen et al., "Alpha-1-antitrypsin content in the serum, alveolar macrophages, and alveolar lavage fluid of smoking and nonsmoking normal subjects," *J. Clin. Invest.,* 55:427-430, 1975.

Ono, Hirose, Miyazaki, Yamamoto, Matsumoto,"Transgenic medaka fish bearing the mouse tyrosinase gene: expression and transmission of the transgene following electroporation of the orange-colored variant," *Pigment Cell Res.,* 10(3):168-175, 1997.

Ostwald, Goldstein, Pachnanda and Roth, *Invest. Ophthalmol. Vis. Sci.,* 36:2396-403, 1995.

Parish, Chandler, Quartey-Papafio, Simpson and Cooke, "The effect of bone marrow and thymus chimerism between non-obese diabetic (NOD) and NOD-E transgenic mice, on the expression and prevention of diabetes," *Eur. J. Immunol.,* 23:2667, 1993.

Parks, Green, Pina and Melnick, "Physicochemical characterization of adeno-associated satellite virus type 4 and its nucleic acid,"*J. Virol.,* 1:980-87, 1967. Parks, Melnick, Rongey, Mayor, "Physical assay and growth cycle studies of a defective adeno-satellite virus," *J. Virol.,* 1:171-80, 1967.

Patema, Moccetti, Mura, Feldon and Bueler, "Influence of promoter and WHV post-transcriptional regulatory element on AAV-mediated transgene expression in the rat brain," *Gene Ther.,* 7:1304-11, 2000.

Paterson et al., "The regions of the herpes simplex virus type 1 immediate early protein Vmw 175 required for site specific DNA binding closely correspond to those involved in transcriptional regulation," *Nucleic Acids Res.,* 16:11005-25, 1988a.

Paterson et al., "Mutational dissection of the HSV-1 immediate-early protein Vmw175 involved in transcriptional transactivation and repression," *Virology,* 166:186-96, 1988b.

Patterson, Perrella, Hsieh, Yoshizumi, Lee and Haber, "Cloning and functional analysis of the promoter for KDR/flk-1, a receptor for vascular endothelial growth factor," *J. Biol. Chem.,* 270:23111-18, 1995.

Peel, Zolotukhin, Schrimsher, Muzyczka and Reier, "Efficient transduction of green fluorescent protein in spinal cord neurons using adeno-associated virus vectors containing cell type-specific promoters," *Gene Ther.,* 4:16-24, 1997.

Peltier and Hansen, "Immunoregulatory activity, biochemistry, and phylogeny of ovine uterine serpin,"*Am. J. Reprod. Immunol.,* 45:266-72, 2001.

Penn, "Why do immunosuppressed patients develop cancer?," *Crit. Rev. Onogen.,* 1:27-52, 1989.

Pennline, Roque-Gaffney and Monahan, "Recombinant human IL-10 prevents the onset of diabetes in the nonobese diabetic mouse," *Clin. Immunol. Immunopathol.,* 71:169-75, 1994.

Pereira and Muzyczka, "The cellular transcription factor SP1 and an unknown cellular protein are required to mediate Rep protein activation of the adeno-associated virus p19 promoter," *J. Virol.,* 71:1747-56, 1997.

Pereira, McCarty and Muzyczka, "The adeno-associated virus (AAV) Rep protein acts as both a repressor and an activator to regulate AAV transcription during a productive infection,"*J. Virol.,* 71:1079-88, 1997.

Perlino, Cortese and Ciliberto, "The human alpha 1-antitrypsin gene is transcribed from two different promoters in macrophages and hepatocytes," *Embo. J.,* 6:2767-71, 1987.

Perlmutter and Punsal, "Distinct and additive effects of elastase and endotoxin on expression of al proteinase inhibitor in mononuclear phagocytes," *J. Biol. Chem.*, 263: 16499-503, 1988.

Perlmutter et al., "Expression of the alpha 1-proteinase inhibitor gene in human monocytes and macrophages," *Proc. Nat'l Acad. Sci. USA*, 82:795-799, 1985.

Perlmutter et al., "Identification of a serpin-enzyme complex receptor on human hepatoma cells and human monocytes," *Proc. Nat'l Acad. Sci. USA*, 87:3753-57, 1990.

Perlmutter, May and Sehgal, "Interferon beta 2/interleukin 6 modulates synthesis of alpha 1-antitrypsin in human mononuclear phagocytes and in human hepatoma cells," *J. Clin. Invest.*, 84:138-144, 1989.

Perreault, Wu, Cousinequ, Ogilvie, Cedergren, "Mixed deoxyribo- and ribo-oligonucleotides with catalytic activity," *Nature*, 344(6266):565, 1990.

Perrey, Ishibashi, Kitamine, Osuga, Yagyu, Chen, Shionoiri, Izuka, Yahagi, Tamura, Ohashi, Harada, Gotoda and Yamada, "The LDL receptor is the major pathway for 13-VLDL uptake by mouse peritoneal macrophages," *Atherosclerosis*, 154:51-60, 2001.

Perrotta and Been, "Cleavage of oligoribonucleotides by a ribozyme derived from the hepatitis delta virus RNA sequence," *Biochem.*, 31(1):16, 1992.

Peters, Gies, Gelb and Peterfreund, "Agonist-induced desensitization of A2B adenosine receptors," *Biochem. Pharmacol.*, 55:873-82, 1998.

Philip et al., "Efficient and sustained gene expression in primary T lymphocytes and primary and cultured tumor cells mediated by adeno-associated virus plasmid DNA complexed to cationic liposomes," *Mol. Cell. Biol.*, 14(4):2411-2418, 1994.

Phillips, Parish, Drage and Cooke, "Cutting edge: interactions through the IL-10 receptor regulate autoimmune diabetes," *J. Immunol.*, 167:6087-91, 2001.

Picard and Schaffner, "A Lymphocyte-specific enhancer in the mouse immunoglobulin kappa gene," *Nature*, 307:83, 1984.

Pieken, Olsen, Benseler, Aurup, Eckstein, "Kinetic characterization of ribonuclease-resistant 2'-modified hammerhead ribozymes," *Science*, 253(5017):314, 1991.

Pikul et al., "In vitro killing of melanoma by liposome-delivered intracellular irradiation," *Arch. Surg.*, 122:1417-20, 1987.

Pileggi, Molano, Berney, Cattan, Vizzardelli, Oliver, Fraker, Ricordi, Pastori, Bach and Inverardi, "Herne oxygenase-1 induction in islet cells results in protection from apoptosis and improved in vivo function after transplantation," *Diabetes*, 50:1983-91, 2001.

Pinto-Alphandary, Balland and Couvreur, "A new method to isolate polyalkylcyanoacrylate nanoparticle preparations," *J. Drug Target*, 3(2): 167-169, 1995.

Pinto-Sietsma and Paul, "Transgenic rats as models for hypertension," *J. Hum. Hypertens.*, 11(9):577-581, 1997.

Pitas, "Expression of the acetyl low density lipoprotein receptor by rabbit fibroblasts and smooth muscle cells. Upregulation by phorbol esters," *J. Biol. Chem.*, 265:12722-27, 1990.

Pitas, Boyles, Mahley and Bissell, "Uptake of chemically modified low density lipoproteins in vivo is mediated by specific endothelial cells," *J. Cell Biol.*, 100:103-17, 1985.

Pitluk and Ward, *J. Virol.*, 65:6661-70, 1991.

Pober, "Immunobiology of human vascular endothelium," *Immunol. Res.*, 19:225-32, 1999.

Polans, Baehr and Palczewski, "Turned on by $Ca^{2+}$! The physiology and pathology of Ca(2+)-binding proteins in the retina," *Trends Neurosci.*, 19:547-554, 1996.

Ponnazhagan, Erikson, Kearns, Zhou, Nahreini, Wang and Srivastava, "Lack of site-specific integration of the recombinant adeno-associated virus 2 genomes in human cells," *Hum. Gene Ther.*, 8:275-84, 1997.

Ponnazhagan, Mukherjee, Wang, Qing, Kube, Mah, Kurpad, Yoder, Srour and Srivastava, "Adeno-associated virus type 2-mediated transduction in primary human bone marrow-derived $CD34^+$ hematopoietic progenitor cells: donor variation and correlation of transgene expression with cellular differentiation," *J. Virol.*, 71:8262-67, 1997.

Portera-Cailliau, Sung, Nathans and Adler, "Apoptotic photoreceptor cell death in mouse models of retinitis pigmentosa," *PNAS*, 91:974-978, 1994.

Potter et al., "Enhancer-dependent expression of human κ immunoglobulin genes introduced into mouse pre-B lymphocytes by electroporation," *Proc. Natl. Acad. Sci. USA*, 81:7161-65, 1984.

Prasad, Yang, Bleich and Nadler, "Adeno-associated virus vector mediated gene transfer to pancreatic β cells," *Gene Ther.*, 7:1553-61, 2000.

Prokop and Bajpai, "Recombinant DNA Technology I," Conference on Progress in Recombinant DNA Technology Applications, Potosi, Mich., Jun. 3-8, 1990, *Ann. N.Y. Acad. Sci.*, 646:1-383, 1991.

Punglia, Lu, Hsu, Kuroki, Tolentino, Keough, Levy, Levy, Goldberg, D'Amato and Adamis, "Regulation of vascular endothelial growth factor expression by insulin-like growth factor I," *Diabetes*, 46:1619-26, 1997.

Qing, Mah, Hansen, Zhou, Dwarki and Srivastava, "Human fibroblast growth factor receptor 1 is a co-receptor for infection by adeno-associated virus 2," *Nat. Med.*, 5:71-77, 1999.

Qiu and Brown, "A 110-kDa nuclear shuttle protein, nucleolin, specifically binds to adeno-associated virus type 2 (AAV-2) capsid," *Virology*, 257:373-82, 1999.

Qiu, Handa, Kirby and Brown, "The interaction of heparin sulfate and adeno-associated virus 2," *Virology*, 269:137-47, 2000.

Quinlan et al., "The intranuclear location of a herpes simplex virus DNA binding protein is determined by the status of viral DNA replication," *Cell*, 36:857-68, 1984.

Quintanar-Guerrero, Allemann, Doelker, Fessi, "Preparation and characterization of nanocapsules from preformed polymers by a new process based on emulsification-diffusion techinque," *Phamr. Res.*, 15(7):1056-1062, 1998.

Rabinovitch, "An update on cytokines in the pathogenesis of insulin-dependent diabetes mellitus," *Diabetes Metab. Rev.*, 14:129-51, 1998.

Rabinovitch, "Immunoregulatory and cytokine imbalances in the pathogenesis of IDDM: therapeutic intervention by immunostimulation?," *Diabetes*, 44:613-621, 1994.

Rabinovitch, Suarez-Pinzon, Sorensen, Bleackley, Power and Rajotte, "Combined therapy with interleukin-4 and interleukin-10 inhibits autoimmune diabetes recurrence in syngeneic islet-transplanted nonobese diabetic mice. Analysis of cytokine mRNA expression in the graft," *Transplantation*, 60:368-74, 1995.

Rabinowitz and Samulski, "Adeno-associated virus expression systems for gene transfer," *Curr. Opin. Biotechnol.*, 9:470-75, 1998.

Rabinowitz and Samulski, "Building a better vector: the manipulation of AAV virions," *Virology*, 278:301-08, 2000.

Rabinowitz, Rolling, Li, Conrath, Xiao, Xiao and Samulski, "Cross-packaging of a single adeno-associated virus (AAV) type 2 vector genome into multiple AAV serotypes enables transduction with broad specificity," *J. Virol.*, 76:791-801, 2002.

Rabinowitz, Xiao and Samulski, "Insertional mutagenesis of AAV2 capsid and the production of recombinant virus," *Virology*, 265:274-85. 1999.

Ranuncoli, Cautero, Ricordi, Masetti, Molano, Inverardi, Alejandro and Kenyon, "Islet cell transplantation: in vivo and in vitro functional assessment of nonhuman primate pancreatic islets," *Cell Transplant*, 9:409-14, 2000.

Rapoport, Jaramillo, Zipris, Lazarus, Serreze, Leiter, Cyopick, Danska and Delovitch, "Interleukin 4 reverses T cell proliferative unresponsiveness and prevents the onset of diabetes in nonobese diabetic mice," *J. Exp. Med.*, 178: 87-99, 1993.

Rasband and Bright, *Microbeam Anal. Soc. J.*, 4:137-49, 1995.

Ray, Desmet and Gepts, "α-1-Antitrypsin immunoreactivity in islet cells of adult human pancreas," *Cell Tissue Res.*, 185:63-68, 1977.

Rego, Santos and Oliveira, "Oxidative stress, hypoxia, and ischemia-like conditions increase the release of endogenous amino acids by distinct mechanisms in cultured retinal cells,"*J. Neurochem.*, 66:2506-16, 1996.

Reinhold-Hurek and Shub, "Self-splicing introns in tRNA genes of widely divergent bacteria," *Nature*, 357:173-176, 1992.

REMINGTON'S PHARMACEUTICAL SCIENCES, 15th Ed., Mack Publishing Company, 1975.

Rendahl, Leff, Otten, Spratt, Bohl, Roey, Donahue, Cohen, Mandel, Danos and Smyder, "Regulation of gene expression in vivo following transduction by two separate rAAV vectors," *Nature Biotech.* 16:757-62, 1998.

Renneisen et al., "Inhibition of expression of human immunodeficiency virus-1 in vitro by antibody-targeted liposomes containing antisense RNA to the env region," *J. Biol. Chem.*, 265:16337-42, 1990.

Rice and Knipe, "Genetic evidence for two distinct transactivation functions of the herpes simplex virus alpha protein ICP27,"*J. Virol.*, 64:1704-15, 1990.

Richard, Berra, Gothie, Roux and Pouyssegur, "p42/p44 mitogen-activated protein kinases phosphorylate hypoxia-inducible factor 1α (HIF-1α) and enhance the transcriptional activity of HIF-1," *J. Biol. Chem.*, 274:32631-37, 1999.

Ricordi, Lacy, Finke, Olack and Scharp, "Automated method for isolation of human pancreatic islets," *Diabetes*, 37:413-20, 1988.

Ridgeway, "Mammalian expression vectors," *In: Vectors: A survey of molecular cloning vectors and their uses*, Rodriguez and Denhardt (ed.), Stoneham: Butterworth, pp. 467-492, 1988.

Ried, Girod, Leike, Buning and Hallek, "Adeno-associated virus capsids displaying immunoglobulin-binding domains permit antibody-mediated vector retargeting to specific cell surface receptors,"*J. Virol.*, 76:4559-66, 2002.

Rippe et al., "DNA-mediated gene transfer into adult rat hepatocytes in primary culture," *Mol. Cell. Biol.*, 10:689-95, 1990.

Robbins and Evans, "Prospects for treating autoimmune and inflammatory diseases by gene therapy," *Gene Therapy*, 3:187-89, 1996.

Robertson, "Pancreatic islet cell transplantation: likely impact on current therapeutics for Type 1 diabetes mellitus," *Drugs*, 61:2017-20, 2001.

Robinson, Pierce, Rook, Foley, Webb and Smith, "Oligodeoxynucleotides inhibit retinal neovascularization in a murine model of proliferative retinopathy," *Proc. Nat'l Acad. Sci. USA*, 93:4851-56, 1996.

Roizman and Sears, In FIELDS VIROLOGY, Fields et al. (eds.), Lippincott-Raven, Philadelphia, pp. 2231-95, 1996.

Rolling, Nong, Pisvin and Collen, "Adeno-associated virus-mediated gene transfer into rat carotid arteries," *Gene Therapy*, 4:757-761, 1997.

Rolling, Shen, Tabarias, Constable, Kanagasingam, Barry and Rakoczy, "Evaluation of adeno-associated virus-mediated gene transfer into the rat retina by clinical fluorescence photography," *Hum. Gene Ther.*, 10:641-48, 1999.

Rose and Koczot, "Adenovirus-associated virus multiplication. VII. Helper requirement for viral deoxyribonucleic acid and ribonucleic acid synthesis," *J. Virol.*, 10:1-8, 1972.

Rose, Berns, Hoggan, Koczot, "Evidence for a single-stranded adenovirus-associated virus genome: formation of a DNA density hybrid on release of viral DNA," *Proc. Natl. Acad. Sci. USA*, 64(3):863-869, 1969.

Rosen et al., *Nature*, 362:59-62, 1993. Wang et al., "Efficient CFTR expression from AAV vectors packaged with promoters—the second generation," *Gene Ther.*, 6(4):667-675, 1999.

Rosen, Danoff, DePiero and Ziyadeh, *Biochem. Biophys. Res. Commun.*, 207:80-88, 1995.

Rosenberg, "Clinical islet cell transplantation. Are we there yet?," *Int. J. Pancreatol.*, 24:145-68, 1998.

Rossi, Elkins, Zaia, Sullivan, "Ribozymes as anti-HIV-1 therapeutic agents: principles, applications, and problems," *AIDS Res. Hum. Retrovir.*, 8(2):183, 1992.

Rossini, Like, Chick, Appel and Cahill, "Studies of streptozotocin-induced insulitis and diabetes," *Proc. Natl. Acad. Sci. USA*, 74:2485-89, 1977.

Rossman, "The canyon hypothesis. Hiding the host cell receptor attachment site on a viral surface from immune surveillance," *J. Biol. Chem.*, 264:14587-90, 1989.

Ruffing, Heid and Kleinschmidt, "Mutations in the carboxy terminus of adeno-associated virus 2 capsid proteins affect viral infectivity: lack of an RGD integrin-binding motif," *J. Gen. Virol.*, 75:3385-92, 1994.

Ruffing, Zentgraf and Kleinschmidt, "Assembly of viruslike particles by recombinant structural proteins of adeno-associated virus type 2 in insect cells," *J. Virol.*, 66:6922-30, 1992.

Russell et al., "DNA synthesis and topoisomerase inhibitors increase transduction by adeno-associated virus vectors," *Proc. Natl. Acad. Sci. USA*, 92:5719-23, 1995.

Rutledge, Halbert and Russell, "Infectious clones and vectors derived from adeno-associated virus (AAV) serotypes other than AAV type 2," *J. Virol.*, 72:309-19, 1998.

Saito, Park, Skolik, Alfaro, Chaudhry, Barnstable and Liggett, "Experimental preretinal neovascularization by laser-induced venous thrombosis in rats," *Curr. Eye Res.*, 16:26-33, 1997.

Sakimura et al., "Upstream and intron regulatory regions for expression of the rat neuron-specific enolase gene," *Brain Res. Mol. Brain. Res.*, 1:19-28, 1993.

Salceda and Caro, "Hypoxia-inducible factor 1alpha (HIF-1α) protein is rapidly degraded by the ubiquitin-proteasome system under normoxic conditions. Its stabilization by hypoxia depends on redox-induced changes," *J. Biol. Chem.*, 272:22642-47, 1997.

Sallenave and Ryle, "Purification and characterization of elastase-specific inhibitor. Sequence homology with mucus proteinase inhibitor," *Biol. Chem. Hoppe-Seyler*, 372:13-21, 1991.

Salvetti, "Factors influencing recombinant adeno-associated virus production," *Hum. Gene Ther.*, 9:695-706, 1998.

Sambrook et al., MOLECULAR CLONING: A LABORATORY MANUAL, Cold Spring Harbor Laboratory, Cold Spring Harbor, N.Y., 1989.

Samulski and Shenk, "Adenovirus E1B 55-M, polypeptide facilitates timely cytoplasmic accumulation of adeno-associated virus mRNAs," *J. Virol.*, 62:206-10, 1988.

Samulski et al., "A recombinant plasmid from which an infectious adeno-associated virus genome can be excised in vitro and its use to study viral replication," *J. Virol.*, 61:3096-101, 1987.

Samulski, "Adeno-associated virus: integration at a specific chromosomal locus," *Curr. Opin. Genet. Dev.*, 3:74-80, 1993.

Samulski, Berns, Tan, Muzyczka, "Cloning of adeno-associated virus into pBR322: rescue of intact virus from the recombinant plasmid in human cells," *Proc. Natl. Acad. Sci. USA*, 79(6):2077-2080, 1982.

Samulski, Chang and Shenk, "Helper-free stocks of recombinant adeno-associated viruses: normal integration does not require viral gene expression," *J. Virol.*, 63:3822-28, 1989.

Samulski, Srivastava, Berns, Muzyczka, "Rescue of adeno-associated virus from recombinant plasmids: gene correction within the terminal repeats of AAV," *Cell*, 33:135-43, 1983.

Samulski, Zhu, Xiao, Brook, Housman, Epstein and Hunter, "Targeted integration of adeno-associated virus (AAV) into human chromosome 19," *Embo. J.*, 10:3941-50, (published erratum appears in *Embo. J., March;* 11:1228, 1992) 1991.

Sandelain, Qin, Lauzon and Singh, "Prevention of type 1 Type I diabetes in NOD mice by adjuvant immunotherapy," *Diabetes*, 39:583, 1990.

Sandri-Goldin and Mendoza, "A herpesvirus regulatory protein appears to act post-transcriptionally by affecting mRNA processing," *Genes Dev.*, 6:848-63, 1992.

Sanes, Rubenstein and Nicolas, EMBO J., 5:3133-42, 1986.

Sarver, Cantin, Chang, Zaia, Ladne, Stephens, Rossi, "Ribozymes as a potential anti-HIV-1 therapeutic agents," *Science*, 247(4947):1222-1225, 1990.

Saville and Collins, "A site-specific self-cleavage reaction performed by a novel RNA in *Neurospora* mitochondria," *Cell*, 61(4):685-696, 1990.

Saville and Collins, "RNA-mediated ligation of self-cleavage products of a *Neurospora* mitochondrial plasmid transcript," *Proc. Natl. Acad. Sci. USA*, 88(19):8826-8830, 1991.

Sawicki et al., "A composite CMV-IE enhancer/beta-actin promoter is ubiquitously expressed in mouse cutaneous epithelium," *Exp. Cell Res.*, 10:367-369, 1998.

Scanlon, Jiao, Funato, Wang, Tone, Rossi, Kashani-Sabet, "Ribozyme-mediated cleavage of c-fos mRNA reduces gene expression of DNA synthesis enzymes and metallothionein," *Proc. Natl. Acad. Sci. USA*, 88(23): 10591-10595, 1991.

Scaringe, Francklyn, Usman, "Chemical synthesis of biologically active oligoribonucleotides using beta-cyanoethyl protected ribonucleoside phosphoramidites," *Nucl. Acids Res.*, 18(18):5433-5441, 1990.

Scharp, Lacy, Santiago, McCullough, Weide, Boyle, Falqui, Marchetti, Ricordi, Gingerich et al., "Results of our first nine intraportal islet allografts in Type 1 Type I, insulin-dependent diabetic patients," *Transplantation*, 51:76-85, 1991.

Schmidt-Wolf and Schmidt-Wolf, "Cytokines and gene therapy," *Immunology Today*, 16:173-75, 1995.

Sculier et al., "Pilot study of amphotericin B entrapped in sonicated liposomes in cancer patients with fungal infections," *J. Cancer Clin. Oncol.*, 24:527-38, 1988.

Segal, BIOCHEMICAL CALCULATIONS, 2nd Ed., John Wiley & Sons, New York, 1976.

Selden, "Transfection using DEAE-Dextran," in *Current Protocols in Molecular Biology*, Ausubel, et al. (Eds.), John Wiley & Sons: New York, pp. 9.2.1-9.2.6, 1993.

Senaphthy, Trats chin and Carter, "Replication of adeno-associated virus DNA. Complementation of naturally occurring rep$^-$ mutants by a wild-type genome or an ori$^-$ mutant and correction of terminal palindrome deletions," *J. Mol. Biol.*, 179:1-20, 1984.

Serreze, "Autoimmune diabetes results from genetic defects manifest by antigen presenting cells," *FASEB J.*, 7:1092-96, 1993.

Sexl, Mancusi, Baumgartner Parzer, Schutz and Freissmuth, "Stimulation of human umbilical vein endothelial cell proliferation by A2-adenosine and beta 2-adrenoceptors," *Br. J. Pharmacol.*, 114:1577-86, 1995.

Shafron, Simpkins, Jebelli, Day and Meyer, "Reduced MK801 binding in neocortical neurons after AAV-mediated transfections with NMDA-R1 antisense cDNA," *Brain Res.* 784:325-328, 1998.

Shapiro, Lakey, Ryan, Korbutt, Toth, Warnock, Kneteman and Rajotte, "Islet transplantation in seven patients with type 1 diabetes mellitus using a glucocorticoid-free immunosuppressive regimen," *N. Engl. J. Med.*, 343:230-38, 2000.

Sharp, "The current status of alpha-1-antityrpsin, a protease inhibitor, in gastrointestinal disease," *Gastroenterology*, 70:611-21, 1976.

Shaw and Lewin, "Protein-induced folding of a group I intron in cytochrome b pre-mRNA," *J. Biol. Chem.*, 270(37): 21552-62, 1995.

Shaw, Whalen, Drenser, et al., "Ribozymes in the treatment of retinal disease," In: *Vertebrate Phototransduction and the Visual Cycle. Methods in Enzymology* 316 Palczewski, Ed., New York, Academic Press, in press, 2000.

She, Ellis, Wilson, Wasserfall, Marron, Reimsneider, Kent, Hafler, Neuberg, Muir, Strominger and Atkinson, "Heterophile antibodies segregate in families and are associated with protection from type 1 Type I diabetes," *Proc. Natl. Acad. Sci. USA*, 96:8116-19, 1999.

Shehadeh, Clacinaro, Bradley, Bruchlim, Vardi and Lafferty, "Effect of adjuvant therapy on the development of diabetes in mouse and man," *The Lancet*, 343:706, 1994.

Shelburne and Ryan, "The role of Th2 cytokines in mast cell homeostasis," *Immunol. Rev.*, 179:82-93, 2001.

Shepard et al., "A second-site revertant of a defective herpes simplex virus ICP4 protein with restored regulatory activities and impaired DNA-binding properties," *J. Virol.*, 65:787-95, 1991.

Shepard et al., "Separation of primary structural components conferring autoregulation, transactivation, and DNA-binding properties to the herpes simplex virus transcriptional regulatory protein ICP4," *J. Virol.*, 63:3714-28, 1989.

Shi, Arnold and Bartlett, "Insertional mutagenesis of the adeno-associated virus type 2 (AAV2) capsid gene and generation of aav2 vectors targeted to alternative cell-surface receptors," *Hum. Gene Ther.*, 12:1697-1711, 2001.

Shima, Kuroki, Deutsch, Ng, Adamis and D'Amore, "The mouse gene for vascular endothelial growth factor. Genomic structure, definition of the transcriptional unit, and characterization of transcriptional and post-transcriptional regulatory sequences," *J. Biol. Chem.*, 271:3877-83, 1996.

Shimayama, Nishikawa and Taira, "Generality of the NUX rule: kinetic analysis of the results of systematic mutations in the trinucleotide at the cleavage site of hammerhead ribozymes," *Biochem.*, 34:3649-3654, 1995.

Shryock and Belardinelli, "Adenosine and adenosine receptors in the cardiovascular system: biochemistry, physiology, and pharmacology,"*Am. J. Cardiol.*, 79:2-10, 1997.

Sibley and Sutherland, "Pancreas transplantation. An immunohistologic and histopathologic examination of 100 grafts,"*Am. J. Pathol.*, 128:151-70, 1987.

Simmons et al., *J. Histochem.*, 12:169-181, 1989.

Sleigh and Lockett, "SV40 enhancer activation during retinoic-acid-induced differentiation of F9 embryonal carcinoma cells,"*J. EMBO*, 4:3831, 1985.

Smith, Kopchick, Chen, Knapp, Kinose, Daley, Foley, Smith and Schaeffer, "Essential role of growth hormone in ischemia-induced retinal neovascularization," *Science*, 276:1706-09, 1997.

Smith, Korbutt, Suarez-Pinzon, Kao, Rajotte and Elliott, "Interleukin-4 or interleukin-10 expressed from adenovirus-transduced syngeneic islet grafts fails to prevent β cell destruction in diabetic NOD mice," *Transplantation*, 64:1040-49, 1997.

Smith, Shen, Perruzzi, Soker, Kinose, Xu, Robinson, Driver, Bischoff, Zhang, Schaeffer and Senger, "Regulation of vascular endothelial growth factor-dependent retinal neovascularization by insulin-like growth factor-1 receptor," *Nat. Med.*, 5:1390-95, 1999.

Smith, Wesolowski, McLellan, Kostyk, D'Amato, Sullivan and D'Amore, "Oxygen-induced retinopathy in the mouse," *Invest. Ophthalmol. Vis. Sci.*, 35:101-11, 1994.

Snyder, Miao, Meuse, et al., "Correction of hemophilia B in canine and murine models using recombinant adeno-associated viral vectors," *Nat. Med.*, 5:64-70, 1999.

Snyder, Miao, Patijn, Spratt, Danos, Nagy, Gown, Winther, Meuse, Cohen, Thompson and Kay, "Persistent and therapeutic concentrations of human factor IX in mice after hepatic gene transfer of recombinant AAV vectors," *Nat. Genet.*, 16:270-76, 1997b.

Snyder, Sprat, Lagarde, Bohl, Kaspar, Sloan, Cohen and Danos, "Efficient and stable adeno-associated virus-mediated transduction in the skeletal muscle of adult immunocompetent mice," *Hum. Gene Ther.*, 8:1891-900, 1997a.

Socci, Falqui, Davalli, Ricordi, Braghi, Bertuzzi, Maffi, Secchi, Gavazzi, Freschi et al., "Fresh human islet transplantation to replace pancreatic endocrine function in Type 1Type I diabetic patients. Report of six cases," *Acta Diabetol.*, 28:151-57, 1991.

Song, Embury, Laipis, Berns, Crawford and Flotte, "Stable therapeutic serum levels of human alpha-1 antitrypsin (AAT) after portal vein injection of recombinant adeno-associated virus (rAAV) vectors," *Gene Ther.*, 8:1299-306, 2001b2001a.

Song, Laipis, Berns and Flotte, "Effect of DNA-dependent protein kinase on the molecular fate of the rAAV2 genome in skeletal muscle," *Proc. Natl. Acad. Sci. USA*, 98:4084-88, 2001b.

Song, Morgan, Ellis, Poirer, Chesnut, Wang, Brantly, Muzyczka, Byrne, Atkinson and Flotte, "Sustained secretion of human α1-antitrypsin from murine muscle transduced with adeno-associated virus vectors," *Proc. Natl. Acad. Sci. USA*, 95:14384-88, 1998.

Sonksen, Russell-Jones and Jones, "Growth hormone and diabetes mellitus: a review of sixty-three years of medical research and a glimpse into the future?," *Horm. Res.*, 40:68-79, 1993.

Srivastava, Lusby and Berns, "Nucleotide sequence and organization of the adeno-associated virus 2 genome,"*J. Virol.*, 45:555-64, 1983.

Stein and Carrell, "What do dysfunctional serpins tell us about molecular mobility and disease?,"*Nat. Struct. Biol.*, 2:96-113, 1995.

Stein and Stein, "Bovine aortic endothelial cells display macrophage-like properties towards acetylated 125I-labelled low density lipoprotein," *Biochem. Biophys. Acta*, 620:631-35, 1980.

Stelzner, Weil and O'Brien, "Role of cyclic adenosine monophosphate in the induction of endothelial barrier properties," *J. Cell Physiol.*, 139:157-66, 1989.

Stephenson and Gibson, *Antisense Res. Dev.*, 1:261-68, 1991.

Stevens, Lokeh, Ansite, Field, Gores and Sutherland, "Role of nitric oxide in the pathogenesis of early pancreatic islet dysfunction during rat and human intraportal islet transplantation," *Transplant Proc.*, 26:692, 1994.

Stewart, A. F., Richard, III, C. W., Suzow, J., Stephan D., Weremowicz, S., Morton, C. C., Andra, C. N. (1996) *Genomics* 37(1):68-76.

Studier, Rosenberg, Dunn and Dubendorff, "Use of T7 RNA polymerase to direct expression of cloned genes,"*Methods Enzymol.*, 185:60-89, 1990.

Summerford and Samulski, "Membrane-associated heparan sulfate proteoglycan is a receptor for adeno-associated virus type 2 virions," *J. Virol.*, 72:1438-45, 1998.

Summerford, Bartlett and Samulski, "$\alpha_V\beta_5$ integrin: a co-receptor for adeno-associated virus type 2 infection," *Nat. Med.*, 5:78-82, 1999.

Suzuki, Shin, Fjuikura, Matsuzaki and Takata, "Direct gene transfer into rat liver cells by in vivo electroporation," *FEBS Lett.*, 425:436-40, 1998.

Tahara, Mueller, Ricordi, Robbins and Lotze, "Islet cell transplantation facilitated by gene transfer," *Transplant Proc.*, 24:2975-76, 1992.

Taira, Nakagawa, Nishikawa, Furukawa, "Construction of a novel RNA-transcript-trimming plasmid which can be used both in vitro in place of run-off and (G)-free transcriptions and in vivo as multi-sequences transcription vectors," *Nucl. Acids Res.*, 19(19):5125-5130, 1991.

Takagi, King, Ferrara and Aiello, "Hypoxia regulates vascular endothelial growth factor receptor KDR/Flk gene expression through adenosine A2 receptors in retinal capillary endothelial cells," *Invest. Ophthalmol. Vis. Sci.*, 37:1311-21, 1996a.

Takagi, King, Robinson, Ferrara and Aiello, "Adenosine mediates hypoxic induction of vascular endothelial growth factor in retinal pericytes and endothelial cells," *Invest. Ophthalmol. Vis. Sci.*, 37:2165-76, 1996b.

Takahashi, Kalka, Masuda, Chen, Silver, Kearney, Magner, Isner and Asahara, "Ischemia- and cytokine-induced mobilization of bone marrow-derived endothelial progenitor cells for neovascularization," *Nat. Med.*, 5:434-38, 1999.

Takahashi, Sawasaki, Hata, Mukai and Goto, "Spontaneous transformation and immortalization of human endothelial cells," *In Vitro Cell Dev. Biol.*, 26:265-74, 1990.

Takakura, "Drug delivery systems in gene therapy," *Nippon Rinsho*, 56:691-95, 1998. Tamayose et al., "A new strategy for large-scale preparation of high-titer recombinant adeno-associated virus vectors by using packaging cell lines and sulfonated cellulose column chromatography," *Hum. Gene Ther.*, 7:507-13, 1997.

Taomoto, McLeod, Merges and Lutty, "Localization of adenosine A2a receptor in retinal development and oxygen-induced retinopathy," *Invest. Ophthalmol. Vis. Sci.*, 41:230-43, 2000.

Taylor and Rossi, *Antisense Res. Dev.*, 1:173-86, 1991.

Taylor-Robinson and Phillips, "Expression of IL-1 receptor discriminates Th2 from Th1 cloned CD4+ T cells specific for *Plasmodium chabaudi*," *Immunology*, 81:216, 1994.

Thomson and Efstathiou, "Acquisition of the human adeno-associated virus type-2 rep gene by human herpesvirus type-6," *Nature*, 351:78-80, 1991.

Thomson et al., "Human herpesvirus 6 (HHV-6) is a helper virus for adeno-associated virus type 2 (AAV-2) and the AAV-2 rep gene homologue in HHV-6 can mediate AAV-2 DNA replication and regulate gene expression," *Virology*, 204:304-11, 1994.

Tian, Olcott, Hanssen, Zekzer, Middleton and Kaufman, "Infectious Th1 and Th2 autoimmunity in diabetes-prone mice,"*Immunol. Rev.*, 164:119-27, 1998.

Timmers, Newton and Hauswirth, "Synthesis and stability of retinal photorecptor mRNAs are coordinately regulated during bovine fetal development," *Exp. Eye Res.*, 56:251-265, 1993.

Tratschin, Miller and Carter, "Genetic analysis of adeno-associated virus: properties of delection mutants constructed in vitro and evidence for an adeno-associated virus replication function,"*J. Virol.*, 51:611-19, 1984.

Tratschin, West, Sandbank and Carter, "A human parvovirus, adeno-associated virus, as a eucaryotic vector: transient expression and encapsidation of the procaryotic gene for chloramphenicol acetyltransferase,"*Mol. Cell. Biol.*, 4:2072-81, 1984.

Tremblay, Sallenave, Israel-Assayag, Cormier and Gauldie, "Elafin/elastase-specific inhibitor in bronchoalveolar lavage of normal subjects and farmer's lung,"*Am. J. Respir. Crit. Care Med.*, 154:1092-98, 1996.

Trempe and Carter, "Alternate mRNA splicing is required for synthesis of adeno-associated virus VP1 capsid protein,"*J. Virol.*, 62:3356-63, 1988.

Tresnan, Southard, Weichert, Sgro and Parrish, "Analysis of the cell and erythrocyte binding activities of the dimple and canyon regions of the canine parvovirus capsid," *Virol.*, 211:123-32, 1995.

Trudeau, Dutz, Arany, Hill, Fieldus and Finegood, "Neonatal β-cell apoptosis: a trigger for autoimmune diabetes?,"*Diabetes*, 49:1-7, 2000.

Tsao, Chapman, Agbandje, Keller, Smith, Wu, Luo, Smith, Rossman, Compans, et al., "The three-dimensional structure of canine parvovirus and its functional implications," *Science*, 251:1456-64, 1991.

Tsao, Chapman, Wu, Agbandje, Keller and Rossman, "Structure determination of monoclinic canine parvovirus,"*Acta. Crystallogr. B*, 48:75-88, 1992.

Tuder, Karasek and Bensch, "Cyclic adenosine monophosphate levels and the function of skin microvascular endothelial cells,"*J. Cell Physiol.*, 142:272-83, 1990.

Tur-Kaspa et al., "Use of electroporation to introduce biologically active foreign genes into primary rat hepatocytes, "*Mol. Cell. Biol.*, 6:716-18, 1986.

Usman and Cedergren, "Exploiting the chemical synthesis of RNA," *Trends Biochem. Sci.*, 17(9):334, 1992.

Usman et al., *J. Am. Chem. Soc.*, 109:7845-7854, 1987.

Van Cott, Lubon, Russell, Butler, Gwazdauskas, Knight, Drohan, Velander, "Phenotypic and genotypic stability of multiple lines of transgenic pigs expressing recombinant human protein C," *Transgenic Res.*, 6(3):203-212, 1997.

van Ginkel and Hauswirth, *J. Biol. Chem.*, 269:4986-92, 1994.

Vanbever et al., "In vivo noninvasive evaluation of hairless rat skin after high-voltage pulse exposure," *Skin Parmacol. Appl. Skin Physiol.*, 11:23-34, 1998.

Vanbever, Fouchard, Jadoul, De Morre, Preat, Marty, "In vivo noninvasive evaluation of hairless rat skin after high-voltage pulse exposure," *Skin Parmacol. Appl. Skin Physiol.*, 11(1):23-34, 1998.

Varban, Rinninger, Wang, Fairchild-Huntress, Dunmore, Fang, Gosselin, Dixon, Deeds, Acton, Tall and Huszar, "Targeted mutation reveals a central role for SR-BI in hepatic selective uptake of high density lipoprotein cholesterol," *Proc. Natl. Acad. Sci. USA*, 95:4619-24, 1998.

Veldwijk, Topaly, Laufs, Hengge, Wenz, Zeller and Fruehauf, "Development and optimization of a real-time quantitative PCR-based method for the titration of AAV-2 vector stocks,"*Mol. Ther.*, 6:272-78, 2002.

Venkatesan, Davidson and Hutchinson, "Possible role for the glucose-fatty acid cycle in dexamethasone-induced insulin antagonism in rats," *Metabolism*, 36:883-91, 1987.

Ventura, Wang, Ragot, Perricaudet, Saragosti, "Activation of HIV-specific ribozyme activity by self-cleavage," *Nucl. Acids Res.*, 21:3249-3255, 1993.

Vestweber and Blanks, "Mechanisms that regulate the function of the selectins and their ligands," *Physiol. Rev.*, 79:181-213, 1999.

Vincent et al., "Analysis of recombinant adeno-associated virus packaging and requirements for rep and cap gene products,"*J. Virol.* 71:1897-905, 1997a.

Vincent et al., "Preclinical testing of recombinant adenoviral herpes simplex virus-thymidine kinase gene therapy for central nervous system malignancies," *Neurosurgery*, 41:442-51, 1997b.

Vincent et al., "Replication and packaging of HIV envelope genes in a novel adeno-associated virus vector system," *Vaccine*, 90:353-59, 1990.

Virella-Lowell, Song, Morgan and Flotte, "A CMV/β-actin hybrid promoter greatly improves recombinant adeno-associated virus (rAAV) vector expression in the murine lung," *Ped. Pulmonol.*, S19:231, 1999.

von-Weizsacker, Blum and Wands, *Biochem. Biophys. Res. Commun.*, 189:743-48, 1992.

Voyta, Via, Butterfield and Zetter, "Identification and isolation of endothelial cells based on their increased uptake of acetylated-low density lipoprotein," *J. Cell Biol.*, 99:2034-40, 1984.

Wagner, Reynolds, Moran, Moss, Wine, Flotte and Gardner, "Efficient and persistent gene transfer of AAV-CFTR in maxillary sinus," *Lancet*, 351:1702-03, 1998.

Wagner, Zatloukal, Cotten, Kirlappos, Mechtler, Curiel and Bimstiel, "Coupling of adenovirus to transferrin-polylysine/DNA complexes greatly enhances receptor-mediated gene delivery and expression of transfected genes," *Proc. Natl. Acad. Sci. USA*, 89:6099-103, 1992.

Walker, et al., "Strand displacement amplification—an isothermal, in vitro DNA amplification technique," *Nucleic Acids Res.*, 20(7):1691-6, 1992.

Walters, Yi, Keshavjee, Brown, Welsh, Chiorini and Zabner, "Binding of adeno-associated virus type 5 to 2,3-linked sialic acid is required for gene transfer," *J. Biol. Chem.*, 276:20610-16, 2001.

Wang, et al., "NGF gene expression in dividing and non-dividing cells from AAV-derived constructs," *Neurochem Res.*, 23(5):779-86, 1998.

Wang, Hao, Gill and Lafferty, "Autoimmune diabetes in NOD mouse is L3T4 T-lymphocyte dependent," *Diabetes,* 36:535-38, 1987.

Warnock, Kneteman, Ryan, Seelis, Rabinovitch and Rajotte, "Normoglycaemia after transplantation of freshly isolated and cryopreserved pancreatic islets in Type 1 Type I (insulin-dependent) diabetes mellitus,"*Diabetologia,* 34:55-58, 1991.

Watson, "Fluid and electrolyte disorders in cardiovascular patients," *Nurs. Clin. North Am.,* 22:797-803, 1987.

Waugh, Li-Hawkins, Yuksel, Cifra, Amabile, Hilfiker, Geske, Kuo, Thomas, Dake and Woo, "Therapeutic elastase inhibition by α-1-antitrypsin gene transfer limits neointima formation in normal rabbits," *J. Vasc. Interv. Radiol.,* 12:1203-09, 2001.

Weerasinghe, Liem, Asad, Read, Joshi, "Resistance to human immunodeficiency virus type 1 (HIV-1) infection in human CD4+ lymphocyte-derived cell lines conferred by using retroviral vectors expression an HIV-1 RNA-specific ribozyme," *J. Virol.,* 65(10):5531-5534, 1991.

Weger, Wendland, Kleinschmidt and Heilbronn, "The adeno-associated virus type 2 regulatory proteins Rep78 and Rep68 interact with the transcriptional coactivator PC4," *J. Virol.,* 73:260-69, 1999.

Wegmann and Eisenbarth, "It's insulin,"*J. Autoimmun.,* 15:286-91, 2000.

Wei et al., *J. Biol. Chem.,* 258:13506-512, 1993.

Weindler and Heilbronn, "A subset of herpes simplex virus replication genes provides helper functions for productive adeno-associated virus replication," *J. Virol.,* 65:2476-83, 1991.

Weir and Bonner-Weir, "Islet transplantation as a treatment for diabetes," *J. Am. Optom. Assoc.,* 69:727-32, 1998.

Weir, Bonner-Weir and Leahy, "Islet mass and function in diabetes and transplantation," *Diabetes,* 39:401-05, 1990.

Weitzman et al., "Interaction of wild-type and mutant adeno-associated virus (AAV) Rep proteins on AAV hairpin DNA," *J. Virol.,* 70:2440-48, 1996a.

Weitzman et al., "Recruitment of wild-type and recombinant adeno-associated virus into adenovirus replication centers, "*J. Virol.,* 70:1845-54, 1996b.

Weitzman, Kyostio, Kotin and Owens, "Adeno-associated virus (AAV) Rep proteins mediate complex formation between AAV DNA and its integration site in human DNA," *Proc. Natl. Acad. Sci. USA,* 91:5808-12, 1994.

Weller "Genetic analysis of HSV-1 gene required for genome replication," In: *Herpes virus transcription and its regulation,* Wagner (ed.), Boca Raton, Fla.: CRC Press, pp. 105-136, 1991.

Wiedow, Schroder, Gregory, Young and Christophers, "Elafin: an elastase-specific inhibitor of human skin. Purification, characterization, and complete amino acid sequence," *J. Biol. Chem.,* 265:14791-95, 1990.

Wistuba, Kern, Weger, Grimm and Kleinschmidt, "Subcellular compartmentalization of adeno-associated virus type 2 assembly," *J. Virol.,* 71:1341-52, 1997.

Wistuba, Weger, Kern and Kleinschmidt, "Intermediates of adeno-associated virus type 2 assembly: identification of soluble complexes containing Rep and Cap proteins," *J. Virol.,* 69:5311-19, 1995.

Wobus, Hugle-Dorr, Girod, Petersen, Hallek and Kleinschmidt, "Monoclonal antibodies against the adeno-associated virus type 2 (AAV-2) capsid: epitope mapping and identification of capsid domains involved in AAV-2-cell interaction and neutralization of AAV-2 infection," *J. Virol.,* 74:9281-93, 2000.

Wogensen, Huang and Sarvetnick, "Leukocyte extravasation into the pancreatic tissue in transgenic mice expressing interleukin 10 in the islets of Langerhans," *J. Exp. Med.,* 178:175-85, 1993.

Wogensen, Lee and Sarvetnick, "Production of interleukin 10 by islet cells accelerates immune-mediated destruction of β cells in nonobese diabetic mice," *J. Exp. Med.,* 179:1379-84, 1994.

Wong and Janeway, "The role of CD4 vs. CD8 T cells in IDDM,"*J. Autoimmun.,* 13:290-95, 1999.

Wong and Neumann, "Electric field mediated gene transfer," *Biochim. Biophys. Res. Commun.,* 107:584-87, 1982.

Wong et al., "Appearance of β-lactamase activity in animal cells upon liposome mediated gene transfer," *Gene,* 10:87-94, 1980.

Woolf, Melton, Jennings, "Specificity of antisense oligonucleotides in vivo," *Proc. Natl. Acad. Sci. USA,* 89(16): 7305-7309, 1992.

Wu and Dean, "Functional significance of loops in the receptor binding domain of *Bacillus thuringiensis* CryIIIA delta-endotoxin," *J. Mol. Biol.,* 255(4):628-640, 1996.

Wu and Wu, "Evidence for targeted gene delivery to HepG2 hepatoma cells in vitro," *Biochemistry,* 27:887-92, 1988.

Wu and Wu, "Receptor-mediated in vitro gene transfections by a soluble DNA carrier system,"*J. Biol. Chem.,* 262: 4429-32, 1987.

Wu et al., "Identification of herpes simples virus type 1 genes required for origin-dependent DNA synthesis," *J. Virol.,* 62:435, 1988.

Wu, Dent, Jelinek, Wolfman, Weber and Sturgill, "Inhibition of the EGF-activated MAP kinase signaling pathway by adenosine 3',5'-monophosphate," *Science,* 262:1065-69, 1993.

Wu, Xiao, Conlon, Hughes, Agbandje-McKenna, Ferkol, Flotte and Muzyczka, "Mutational analysis of the adeno-associated virus type 2 (AAV2) capsid gene and construction of AAV2 vectors with altered tropism," *J. Virol.,* 74:8635-47, 2000.

Wyble, Hynes, Kuchibhotla, Marcus, Hallahan and Gewertz, "TNF-α and IL-1 upregulate membrane-bound and soluble E-selectin through a common pathway," *J. Surg. Res.,* 73:107-12, 1997.

Xiao et al., "Adeno-associated virus (AAV) vector antisense gene transfer in vivo decreases GABA(A) alpha1 containing receptors and increases inferior collicular seizure sensitivity," *Brain Res.,* 756:76-83, 1997.

Xiao, Berta, Lu, Moscioni, Tazelaar and Wilson, "Adeno-associated virus as a vector for liver-directed gene therapy, "*J. Virol.,* 72:10222-26, 1998.

Xiao, Li and Samulski, "Efficient long-term gene transfer into muscle tissue of immunocompetent mice by adeno-associated virus vector,"*J. Virol.,* 70:8098-108, 1996.

Xiao, Li and Samulski, "Production of high-titer recombinant adeno-associated virus vectors in the absence of helper adenovirus,"*J. Virol.* 72:2224-32, 1998.

Xiao, Li, McCown and Samulski, "Gene transfer by adeno-associated virus vectors into the central nervous system," *Exp. Neurol.,* 144:113-124, 1997.

Xie, Bu, Bhatia, Hare, Somasundaram, Azzi and Chapman, "The atomic structure of adeno-associated virus (AAV-2), a vector for human gene therapy," *Proc. Natl. Acad. Sci. USA,* 99:10405-10, 2002.

Xing and Whitton, *J. Virol.,* 67:1840-47, 1993.

Xu and Gong, "Adaptation of inverse PCR to generate an internal deletion," *Biotechniques,* 26:639-41, 1999.

Xu, Daly, Gao, Flotte, Song, Byrne, Sands and Parker Ponder, CMV-β-actin promoter directs higher expression from an adeno-associated viral vector in the liver than the cytomegalovirus or elongation factor 1α promoter and results in therapeutic levels of human factor X in mice," *Hum. Gene Ther.*, 12:563-73, 2001.

Yan, Lewin and Hauswirth. "Selective degradation of non-sense beta-phosphodiesterase mRNA in the heterozygous rd mouse," *Invest. Ophthalmol. Vis. Sci.*, 39:2529-2536, 1998.

Yan, Zhang, Duan and Engelhardt, "From the cover: trans-splicing vectors expand the utility of adeno-associated virus for gene therapy," *Proc. Natl. Acad. Sci. USA*, 97:6716-21, 2000.

Yang and Kotin, "Glucose-responsive gene delivery in pancreatic Islet cells via recombinant adeno-associated viral vectors," *Pharm. Res.*, 17:1056-61, 2000.

Yang et al., "In vivo and in vitro gene transfer to mammalian somatic cells by particle bombardment," *Proc. Natl. Acad. Sci. USA*, 87:9568-72, 1990.

Yang, Mamounas, Yu, Kennedy, Leaker, Merson, Wong-Staal, Yu and Barber, "Development of novel cell surface CD34-targeted recombinant adenoassociated virus vectors for gene therapy," *Hum. Gene Ther.*, 9:1929-37, 1998.

Yang, Scheff and Schalch, "Effects of streptozotocin-induced diabetes mellitus on growth and hepatic insulin-like growth factor I gene expression in the rat," *Metabolism*, 39:295-301, 1990. Yu, Poeschla, Yamada et al., *Virology*, 206:381-86, 1995.

Yarfitz and Hurley, "Transduction mechanisms of vertebrate and invertebrate photoreceptors,"*J. Biol. Chem.*, 269:14329-14332, 1994.

Yoon, Jun and Santamaria, "Cellular and molecular mechanisms for the initiation and progression of β cell destruction resulting from the collaboration between macrophages and T cells," *Autoimmunity*, 27:109-22, 1998.

Yu, Ojwang, Yamada, Hampel, Rapapport, Looney, Wong-Staal, "A hairpin ribozyme inhibits expression of diverse strains of human immunodeficiency virus type 1," *Proc. Natl. Acad. Sci. USA*, 90:6340-6344, 1993.

Yu, Robles, Abiru, Kaur, Rewers, Kelemen and Eisenbarth, "Early expression of antiinsulin autoantibodies of humans and the NOD mouse: evidence for early determination of subsequent diabetes,"*Proc. Natl. Acad. Sci. USA*, 97:1701-06, 2000.

Zabner, Seiler, Walters, Kotin, Fulgeras, Davidson and Chiorini, "Adeno-associated virus type 5 (AAV5) but not AAV2 binds to the apical surfaces of airway epithelia and facilitates gene transfer,"*J. Virol.*, 74:3852-58, 2000.

Zaidi, Hui, Cheah, You, Husain and Rabinovitch, "Targeted overexpression of elafin protects mice against cardiac dysfunction and mortality following viral myocarditis," *J. Clin. Invest.*, 103:1211-19, 1999.

Zambaux, Bonneaux, Gref, Maincent, Dellacherie, Alonso, Labrude, Vigneron, "Influence of experimental paparmeters on the characteristics of poly(lactic acid) nanoparticles prepared by a double emulsion method," *J. Controlled Release*, 50(1-3):31-40, 1998.

Zhang et al., "Adeno-associated virus transduction of islets with interleukin-4 results in impaired metabolic function in syngeneic marginal islet mass transplantation," *Transplantation*, 74:in press, 2002b.

Zhang et al., "Genetic predisposition to autoimmunity specifically imparts responsiveness to transgenes delivered by recombinant adeno-associated virus," *Mol. Ther.*, 5:S430 (Abstr. 1317), 2002a.

Zhong and Hayward, "Assembly of complete functionally active herpes simplex virus DNA replication compartments and recruitment of associated viral and cellular proteins in transient cotransfection assays," *J. Virol.*, 71:3146-60, 1997.

Zhou and Muzyczka, "In vitro packaging of adeno-associated virus DNA," *J. Virol.*, 72:3241-47, 1998.

Zhou, Cooper, Kang, Ruggieri, Heimfeld, Srivastava and Broxmeyer, "Adeno-associated virus 2-mediated high efficiency gene transfer into immature and mature subsets of hematopoietic progenitor cells in human umbilical cord blood," *J. Exp. Med.*, 179:1867-75, 1994.

Zhou, Giordano, Durbin, McAllister, "Synthesis of functional mRNA in mammalian cells by bacteriophage T3 RNA polymerase,"*Mol. Cell. Biol.*, 10(9):4529-4537, 1990.

Ziady et al., "Chain length of the polylysine in receptor-targeted gene transfer complexes affects duration of reporter gene expression both in vitro and in vivo," *J. Biol. Chem.*, 274:4908-16, 1999.

Ziady, Perales, Ferkol, Gerken, Beegen, Perlmutter and Davis, "Gene transfer into hepatoma cell lines via the serpin enzyme complex receptor," *Am. J. Physiol.*, 273(2 Pt 1):G545-52, 1997.

Zolotukhin, Byrne, Mason, et al., "Recombinant adeno-associated virus purification using novel methods improves infectious titer and yield," *Gene Ther.*, 6:973-985, 1999. Zhou, Giordano, Durbin, McAllister, "Synthesis of functional mRNA in mammalian cells by bacteriophage T3 RNA polymerase," *Mol. Cell. Biol.*, 10(9):4529-4537, 1990.

Zolotukhin, Byrne, Mason, Zolotukhin, Potter, Chesnut, Summerford, Samulski and Muzyczka, "Recombinant adeno-associated virus purification using novel methods improves infectious titer and yield," *Gene Ther.*, 6:973-85, 1999.

Zolotukhin, Potter, Hauswirth, Guy and Muzyczka, "A 'humanized' green fluorescent protein cDNA adapted for high-level expression in mammalian cells," *J. Virol.*, 70:4646-54, 1996.

Zolotukhin, Potter, Zolotukhin, Sakai, Loiler, Fraites, Jr., Chiodo, Phillipsberg, Muzyczka, Hauswirth, Flotte, Byrne and Snyder, "Production and purification of serotype 1, 2, and 5 recombinant adeno-associated viral vectors,"*Methods*, 28:158-67, 2002.

Zolotukhin, Zolotukhin, Byrne, Mason, Zolotukhin, Potter, Chesnut, Summerford, Samulski and Muzyczka, "Recombinant adeno-associated virus purification using novel methods improves infectious titer and yield," *Gene Ther.*, 6:973-985, 1999.

zur Muhlen, Schwarz and Mehnert, "Solid lipid nanoparticles (SLN) for controlled drug delivery—drug release and release mechanism," *Eur. J. Pharm. Biopharm.*, 45:149-155, 1998.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A composition, comprising:
(a) a first expression vector comprising a coding sequence of a first AAV capsid protein under control of an expression control sequence; and
(b) a second expression vector comprising coding sequences for a second AAV capsid protein under control of an expression control sequence and a third AAV capsid protein under control of an expression control sequence; wherein the first and the second expression vectors are not on the same nucleic acid segment and wherein the first, the second, and the third capsid proteins are distinct capsid proteins selected from the group consisting of an AAV2 Vp1 protein, an AAV2 Vp2 protein and an AAV2 Vp3 protein, and further wherein the composition is modified 1) by a mutation in the coding sequence for the Vp2 protein such that the coding sequence for Vp2 does not express a functional AAV Vp2 capsid protein and/or 2) at least one mutation such that binding to HPSG is altered, impaired, or prevented wherein the at least one mutation is an arginine-to-alanine mutation or an arginine-to-lysine mutation at an amino acid residue R487, R585, or R588, wherein binding by the mutated capsid protein.

2. The composition of claim 1, further comprising a second mutation in a capsid protein distinct from the protein with the first mutation.

3. The composition of claim 1, further comprising a second mutation in the AAV capsid protein that comprises the first mutation.

4. The composition of claim 1, further comprising a third distinct expression vector that comprises an expression cassette flanked by AAV2 terminal repeat sequences.

5. The composition of claim 4, wherein the expression cassette comprises a first polynucleotide that comprises a first nucleic acid segment that encodes a therapeutic agent.

6. The composition of claim 5, wherein the therapeutic agent is a peptide, a polypeptide, a protein, a catalytic RNA molecule, a ribozyme, an antisense oligonucleotide, or an antisense polynucleotide.

7. The composition of claim 5, wherein the first polynucleotide further comprises a promoter operably linked to the first nucleic acid segment, wherein the promoter controls the expression of the therapeutic agent.

8. The composition of claim 7, wherein the promoter is a heterologous promoter, a tissue-specific promoter, a constitutive promoter, or an inducible promoter.

9. The composition of claim 8, wherein the promoter is selected from the group consisting of a CMV promoter, a β-actin promoter, an insulin promoter, an enolase promoter, a BDNF promoter, an NGF promoter, an EGF promoter, a growth factor promoter, an axon-specific promoter, a dendrite-specific promoter, a brain-specific promoter, a hippocampal-specific promoter, a kidney-specific promoter, an elafin promoter, a cytokine promoter, an interferon promoter, a growth factor promoter, an α-1 antitrypsin promoter, a brain-specific promoter, a neural cell-specific promoter, a central nervous system cell-specific promoter, a peripheral nervous system cell-specific promoter, an interleukin promoter, a serpin promoter, a hybrid CMV promoter, a hybrid β-actin promoter, an EF1 promoter, a U1a promoter, a U1b promoter, a Tet-inducible promoter and a VP16-LexA promoter.

10. The composition of claim 9, wherein the β-actin promoter is a mammalian β-actin promoter.

11. The composition of claim 5, wherein the first polynucleotide further comprises an enhancer sequence operably linked to the first nucleic acid segment.

12. The composition of claim 11, wherein the enhancer sequence comprises a CMV enhancer, a synthetic enhancer, a liver-specific enhancer, an vascular-specific enhancer, a brain-specific enhancer, a neural cell-specific enhancer, a lung-specific enhancer, a muscle-specific enhancer, a kidney-specific enhancer, a pancreas-specific enhancer, or an islet cell-specific enhancer.

13. The composition of claim 12, wherein the enhancer sequence comprises the CMV enhancer.

14. The composition of claim 5, wherein the first nucleic acid segment further comprises a post-transcriptional regulatory sequence or a polyadenylation signal.

15. The composition of claim 14, wherein the regulatory sequence comprises a woodchuck hepatitis virus post-transcription regulatory element, or the polyadenylation signal comprises a bovine growth hormone gene polyadenylation signal.

16. The composition of claim 5, wherein the therapeutic agent is a protein or a polypeptide selected from the group consisting of an adrenergic agonist, an anti-apoptosis factor, an apoptosis inhibitor, a cytokine receptor, a cytokine, a cytotoxin, an erythropoietic agent, a glutamic acid decarboxylase, a glycoprotein, a growth factor, a growth factor receptor, a hormone, a hormone receptor, an interferon, an interleukin, an interleukin receptor, a kinase, a kinase inhibitor, a nerve growth factor, a netrin, a neuroactive peptide, a neuroactive peptide receptor, a neurogenic factor, a neurogenic factor receptor, a neuropilin, a neurotrophic factor, a neurotrophin, a neurotrophin receptor, an N-methyl-D-aspartate antagonist, a plexin, a protease, a protease inhibitor, a protein decarboxylase, a protein kinase, a protein kinase inhibitor, a proteolytic protein, a proteolytic protein inhibitor, a semaphorin, a semaphorin receptor, a serotonin transport protein, a serotonin uptake inhibitor, a serotonin receptor, a serpin, a serpin receptor, and a tumor suppressor.

17. The composition of claim 16, wherein the polypeptide is selected from the group consisting of BDNF, CNTF, CSF, EGF, FGF, G-SCF, GM-CSF, gonadotropin, IFN, IFG-1, M-CSF, NGF, PDGF, PEDF, TGF, TGF-B2, TNF, VEGF, prolactin, somatotropin, XIAP1, IL-1, IL-2, IL-3, IL-4, IL-5, IL-6, IL-7, IL-8, IL-9, IL-10, IL-10(187A), viral IL-10, IL-11, IL-12, IL-13, IL-14, IL-15, IL-16, IL-17, and IL-18.

18. An infectious recombinant adeno-associated virus virion comprising:

(a) a first expression vector comprising a coding sequence of a first AAV capsid protein under control of an expression control sequence; and (b) a second expression vector comprising a coding sequence of a second AAV capsid protein under control of an expression control sequence and a third AAV capsid protein under control of an expression control sequence; wherein the first and the second expression vectors are not on the same nucleic acid segment and wherein the first, the second, and the third capsid proteins are distinct capsid proteins selected from the group consisting of an AAV2 Vp1 protein, an AAV2 Vp2 protein and an AAV2 Vp3 protein, and further wherein the composition is modified 1) by a mutation in the coding sequence for the Vp2 protein such that the coding sequence for Vp2 does not express a functional AAV Vp2 capsid protein and/or 2) at least one mutation such that binding to HPSG is altered, impaired, or prevented wherein the at least one mutation is an arginine-to-alanine mutation or an arginine-to-lysine mutation at an amino acid residue corresponding to R487, R585, or R588, of an AAV2 capsid protein.

19. The infectious recombinant adeno-associated virus virion of claim 18, wherein the virion is selected from the group consisting of AAV serotype 1, AAV serotype 2, AAV serotype 3, AAV serotype 4, AAV serotype 5, and AAV serotype 6.

20. A plurality of infectious adeno-associated viral particles comprising the virion of claim 18.

21. An isolated mammalian host cell comprising: (a) the composition of claim 1, or (b) the infectious recombinant adeno-associated virus virion of claim 18.

22. The mammalian host cell of claim 21, wherein the mammalian cell is a human, a primate, a murine, a feline, a canine, a porcine, an ovine, a bovine, an equine, an epine, a caprine, or a lupine cell.

23. The mammalian host cell of claim 22, wherein the human cell is a human endothelial cell, a vascular cell, an epithelial cell, a liver cell, a lung cell, a cardiac cell, a pancreatic cell, a renal cell, a muscle cell, a bone cell, a neural cell, or a brain cell.

24. A composition comprising: (a) the infectious recombinant adeno-associated virus virion of claim 18; or the plurality of infectious adeno-associated viral particles of claim 20; and (b) a pharmaceutical excipient, buffer, or diluent.

25. The composition of claim 1 or claim 24, formulated for administration to a human.

26. The composition of claim 1 or claim 24, further comprising a liposome, a lipid, a lipid complex, a microsphere, a microparticle, a nanosphere, or a nanoparticle.

27. A kit comprising:
   (a) (i) the composition of claim 1, (ii) the infectious recombinant adeno-associated virus virion of claim 18, or (iii) the plurality of infectious adeno-associated viral particles of claim 20; and
   (b) instructions for using the kit.

28. An infectious rAAV virion encoded by the vector of claim 18.

* * * * *